（12） United States Patent
Rios et al.

(10) Patent No.: US 11,710,424 B2
(45) Date of Patent: Jul. 25, 2023

(54) SYRINGE DOSE AND POSITION MEASURING APPARATUS

(71) Applicant: Truinject Corp., Irvine, CA (US)

(72) Inventors: Gabrielle A. Rios, Newport Beach, CA (US); Scott Cameron Royston, Austin, TX (US); Matthew Ryan, Aliso Viejo, CA (US); Cody Garrett Schulz, Highland, CA (US); Clark B. Foster, Mission Viejo, CA (US)

(73) Assignee: Truinject Corp., Irvine, CA (US)

( * ) Notice: Subject to any disclaimer, the term of this patent is extended or adjusted under 35 U.S.C. 154(b) by 889 days.

(21) Appl. No.: 16/663,040

(22) Filed: Oct. 24, 2019

(65) Prior Publication Data
US 2020/0202747 A1   Jun. 25, 2020

Related U.S. Application Data

(60) Continuation of application No. 16/296,110, filed on Mar. 7, 2019, now abandoned, which is a division of
(Continued)

(51) Int. Cl.
*G09B 23/28* (2006.01)
*G09B 23/30* (2006.01)
(Continued)

(52) U.S. Cl.
CPC ......... *G09B 23/285* (2013.01); *A61M 5/1456* (2013.01); *A61M 5/1458* (2013.01);
(Continued)

(58) Field of Classification Search
CPC .... G09B 23/285; G09B 23/30; A61M 5/1456; A61M 5/1458; A61M 5/31511;
(Continued)

(56) References Cited

U.S. PATENT DOCUMENTS 3,237,340 A   3/1966 Knott
3,722,108 A   3/1973 Chase
(Continued)

FOREIGN PATENT DOCUMENTS

AU   2011218649 B2   9/2011
AU   2015255197 A1   12/2015
(Continued)

OTHER PUBLICATIONS

"A beginner's guide to accelerometers," Dimension Engineering LLC, accessed Jul. 11, 2018, in 2 pages, https://www.dimensionengineering.com/info/accelerometers.
(Continued)

*Primary Examiner* — James D Ponton
(74) *Attorney, Agent, or Firm* — Knobbe, Martens, Olson & Bear, LLP

(57) ABSTRACT

An injection system can have a Syringe Dose and Position Apparatus (SDPA) mounted to a syringe. The SDPA can have one or more circuit boards. The SDPA can include one or more sensors for determining information about an injection procedure, such as the dose measurement, injection location, and the like. The SDPA can also include a power management board, which can be a separate board than a board mounted with the sensors. The syringe can also include a light source in the needle. Light emitted from the light source can be detected by light detectors inside a training apparatus configured to receive the injection. The syringe can have a power source for powering the sensors and the light source. The SDPA and the power source can be mounted to the syringe flange.

14 Claims, 25 Drawing Sheets

Related U.S. Application Data application No. 15/877,310, filed on Jan. 22, 2018, now Pat. No. 10,269,266.

(60) Provisional application No. 62/552,307, filed on Aug. 30, 2017, provisional application No. 62/449,531, filed on Jan. 23, 2017.

(51) Int. Cl.
*A61M 5/315* (2006.01)
*A61M 5/42* (2006.01)
*A61M 5/46* (2006.01)
*A61M 5/48* (2006.01)
*A61M 5/145* (2006.01)
*A61M 5/31* (2006.01)

(52) U.S. Cl.
CPC ...... *A61M 5/3157* (2013.01); *A61M 5/31511* (2013.01); *A61M 5/31535* (2013.01); *A61M 5/31566* (2013.01); *A61M 5/31576* (2013.01); *A61M 5/427* (2013.01); *A61M 5/46* (2013.01); *A61M 5/48* (2013.01); *G09B 23/30* (2013.01); *A61M 5/31525* (2013.01); *A61M 5/31551* (2013.01); *A61M 2005/3139* (2013.01); *A61M 2205/33* (2013.01); *A61M 2205/3306* (2013.01); *A61M 2205/3317* (2013.01); *A61M 2205/3331* (2013.01); *A61M 2205/3584* (2013.01); *A61M 2205/50* (2013.01); *A61M 2205/609* (2013.01)

(58) Field of Classification Search
CPC .......... A61M 5/31535; A61M 5/31566; A61M 5/3157; A61M 5/31576; A61M 5/427; A61M 5/46; A61M 5/48; A61M 5/31525; A61M 5/31551; A61M 2005/3139; A61M 2205/33; A61M 2205/3306; A61M 2205/3317; A61M 2205/3331; A61M 2205/3584; A61M 2205/50; A61M 2205/609

See application file for complete search history.

(56) References Cited

U.S. PATENT DOCUMENTS

| | | |
|---|---|---|
| 3,941,121 A | 3/1976 | Olinger et al. |
| 4,142,517 A | 3/1979 | Contreras Guerrero de Stavropoulos et al. |
| 4,311,138 A | 1/1982 | Sugarman |
| 4,356,828 A | 11/1982 | Jamshidi |
| 4,410,020 A | 10/1983 | Lorenz |
| 4,439,162 A | 3/1984 | Blaine |
| 4,515,168 A | 5/1985 | Chester et al. |
| 4,566,438 A | 1/1986 | Liese et al. |
| 4,836,632 A | 6/1989 | Bardoorian |
| 4,867,686 A | 9/1989 | Goldstein |
| 4,880,971 A | 11/1989 | Danisch |
| 5,065,236 A | 11/1991 | Diner |
| 5,197,476 A | 3/1993 | Nowacki et al. |
| 5,198,877 A | 3/1993 | Schulz |
| 5,241,184 A | 8/1993 | Menzel |
| 5,249,581 A | 10/1993 | Horbal et al. |
| 5,295,483 A | 3/1994 | Nowacki et al. |
| 5,321,257 A | 6/1994 | Danisch |
| 5,391,081 A | 2/1995 | Lampotang et al. |
| 5,517,997 A | 5/1996 | Fontenot |
| 5,518,407 A | 5/1996 | Greenfield et al. |
| 5,534,704 A | 7/1996 | Robinson et al. |
| 5,622,170 A | 4/1997 | Shulz |
| 5,651,783 A | 7/1997 | Reynard |
| 5,690,618 A | 11/1997 | Smith et al. |
| 5,704,791 A | 1/1998 | Gillio |
| 5,727,948 A | 3/1998 | Jordan |
| 5,766,016 A | 8/1998 | Sinclair et al. |
| 5,817,105 A | 10/1998 | Van Der Brug |
| 5,828,770 A | 10/1998 | Leis et al. |
| 5,890,908 A | 4/1999 | Lampotang et al. |
| 5,899,692 A | 5/1999 | Davis et al. |
| 5,923,417 A | 7/1999 | Leis |
| 5,954,648 A | 9/1999 | Van Der Brug |
| 5,954,701 A | 9/1999 | Matalon |
| 6,010,531 A * | 1/2000 | Donlon ............ A61B 17/00234 623/902 |
| 6,024,576 A | 2/2000 | Bevirt et al. |
| 6,061,644 A | 5/2000 | Leis |
| 6,064,749 A | 5/2000 | Hirota et al. |
| 6,127,672 A | 10/2000 | Danisch |
| 6,172,499 B1 | 1/2001 | Ashe |
| 6,217,558 B1 | 4/2001 | Zadini et al. |
| 6,288,785 B1 | 9/2001 | Frantz et al. |
| 6,353,226 B1 | 3/2002 | Khalil et al. |
| 6,385,482 B1 | 5/2002 | Boksberger et al. |
| 6,428,323 B1 | 8/2002 | Pugh |
| 6,470,302 B1 | 10/2002 | Cunningham et al. |
| 6,485,308 B1 | 11/2002 | Goldstein |
| 6,538,634 B1 | 3/2003 | Chui et al. |
| 6,553,326 B1 | 4/2003 | Kirsch et al. |
| 6,564,087 B1 | 5/2003 | Pitris et al. |
| 6,568,941 B1 | 5/2003 | Goldstein |
| 6,575,757 B1 | 6/2003 | Leight et al. |
| 6,625,563 B2 | 9/2003 | Kirsch et al. |
| 6,687,529 B2 | 2/2004 | Van Vaals |
| 6,702,790 B1 | 3/2004 | Ross et al. |
| 6,769,286 B2 | 8/2004 | Biermann et al. |
| 6,774,624 B2 | 8/2004 | Anderson et al. |
| 6,836,745 B2 | 12/2004 | Seiler et al. |
| 6,857,878 B1 | 2/2005 | Chosack et al. |
| 6,863,536 B1 | 3/2005 | Fisher et al. |
| 7,015,859 B2 | 3/2006 | Anderson |
| 7,115,113 B2 | 10/2006 | Evans et al. |
| 7,137,712 B2 | 11/2006 | Brunner et al. |
| 7,158,754 B2 | 1/2007 | Anderson |
| 7,194,296 B2 | 3/2007 | Frantz et al. |
| 7,204,796 B1 | 4/2007 | Seiler |
| 7,247,149 B2 | 7/2007 | Beyerlein |
| 7,383,728 B2 | 6/2008 | Noble et al. |
| 7,474,776 B2 | 1/2009 | Kaufman et al. |
| 7,500,853 B2 | 3/2009 | Bevirt et al. |
| 7,544,062 B1 | 6/2009 | Hauschild et al. |
| 7,553,159 B1 | 6/2009 | Arnal et al. |
| 7,594,815 B2 | 9/2009 | Toly |
| 7,665,995 B2 | 2/2010 | Toly |
| 7,725,279 B2 | 5/2010 | Luinge et al. |
| 7,761,139 B2 | 7/2010 | Tearney et al. |
| 7,783,441 B2 | 8/2010 | Nieminen et al. |
| 7,857,626 B2 | 12/2010 | Toly |
| 7,912,662 B2 | 3/2011 | Zuhars et al. |
| 7,945,311 B2 | 5/2011 | McCloy et al. |
| 8,007,281 B2 | 8/2011 | Toly |
| 8,040,127 B2 | 10/2011 | Jensen |
| 8,072,606 B2 | 12/2011 | Chau et al. |
| 8,103,883 B2 | 1/2012 | Smith |
| 8,131,342 B2 | 3/2012 | Anderson |
| 8,165,844 B2 | 4/2012 | Luinge et al. |
| 8,203,487 B2 | 6/2012 | Hol et al. |
| 8,208,716 B2 | 6/2012 | Choi et al. |
| 8,226,610 B2 | 7/2012 | Edwards et al. |
| 8,250,921 B2 | 8/2012 | Nasiri et al. |
| 8,257,250 B2 | 9/2012 | Tenger et al. |
| 8,277,411 B2 | 10/2012 | Gellman |
| 8,319,182 B1 | 11/2012 | Brady et al. |
| 8,342,853 B2 | 1/2013 | Cohen |
| 8,351,773 B2 | 1/2013 | Nasiri et al. |
| 8,382,485 B2 | 2/2013 | Bardsley |
| 8,403,888 B2 | 3/2013 | Gaudet |
| 8,408,918 B2 | 4/2013 | Hu et al. |
| 8,409,140 B2 | 4/2013 | Ejlersen et al. |
| 8,437,833 B2 | 5/2013 | Silverstein |
| 8,442,619 B2 | 5/2013 | Li et al. |
| 8,450,997 B2 | 5/2013 | Silverman |
| 8,467,855 B2 | 6/2013 | Yasui |
| 8,469,716 B2 | 6/2013 | Fedotov et al. |

(56) References Cited

U.S. PATENT DOCUMENTS

| | | |
|---|---|---|
| 8,525,990 B2 | 9/2013 | Wilcken |
| 8,535,062 B2 | 9/2013 | Nguyen |
| 8,556,635 B2 | 10/2013 | Toly |
| 8,632,498 B2 | 1/2014 | Rimsa et al. |
| 8,647,124 B2 | 2/2014 | Bardsley et al. |
| 8,655,622 B2 | 2/2014 | Yen et al. |
| 8,684,744 B2 | 4/2014 | Selz et al. |
| 8,689,801 B2 | 4/2014 | Ritchey et al. |
| 8,715,233 B2 | 5/2014 | Brewer et al. |
| 8,764,449 B2 | 7/2014 | Rios et al. |
| 8,818,751 B2 | 8/2014 | Van Acht et al. |
| 8,917,916 B2 | 12/2014 | Martin et al. |
| 8,924,334 B2 | 12/2014 | Lacey et al. |
| 8,945,147 B2 | 2/2015 | Ritchey et al. |
| 8,961,189 B2 | 2/2015 | Rios et al. |
| 8,994,366 B2 | 3/2015 | Ashe |
| 9,017,080 B1 | 4/2015 | Placik |
| 9,024,624 B2 | 5/2015 | Brunner |
| 9,031,314 B2 | 5/2015 | Clausen et al. |
| 9,053,641 B2 | 6/2015 | Samosky |
| 9,123,261 B2 | 9/2015 | Lowe |
| 9,251,721 B2 | 2/2016 | Lampotang et al. |
| 9,275,557 B2 | 3/2016 | Trotta |
| 9,318,032 B2 | 4/2016 | Samosky et al. |
| 9,361,809 B1 | 6/2016 | Caron |
| 9,439,653 B2 | 9/2016 | Avneri et al. |
| 9,443,446 B2 | 9/2016 | Rios et al. |
| 9,456,766 B2 | 10/2016 | Cox et al. |
| 9,460,638 B2 | 10/2016 | Baker et al. |
| 9,486,162 B2 | 11/2016 | Zhuang et al. |
| 9,554,716 B2 | 1/2017 | Burnside et al. |
| 9,595,208 B2 | 3/2017 | Ottensmeyer et al. |
| 9,626,805 B2 | 4/2017 | Lampotang et al. |
| 9,666,102 B2 | 5/2017 | East et al. |
| 9,792,836 B2 | 10/2017 | Rios et al. |
| 9,922,578 B2 | 3/2018 | Foster et al. |
| 10,083,630 B2 | 9/2018 | Samosky et al. |
| 10,173,015 B2 | 1/2019 | Fiedler et al. |
| 10,269,266 B2 | 4/2019 | Rios et al. |
| 10,290,231 B2 | 5/2019 | Rios et al. |
| 10,290,232 B2 | 5/2019 | Rios et al. |
| 10,325,522 B2 | 6/2019 | Samosky et al. |
| 10,398,855 B2 | 9/2019 | McClellan |
| 10,500,340 B2 | 12/2019 | Rios et al. |
| 10,643,497 B2 | 5/2020 | Rios et al. |
| 10,743,942 B2 | 8/2020 | Foster et al. |
| 10,849,688 B2 | 12/2020 | Rios et al. |
| 10,857,306 B2 | 12/2020 | Holmqvist et al. |
| 10,896,627 B2 | 1/2021 | Foster et al. |
| 10,902,746 B2 | 1/2021 | Rios et al. |
| 11,403,964 B2 | 8/2022 | Rios et al. |
| 2001/0037191 A1 | 11/2001 | Furuta et al. |
| 2002/0076681 A1 | 6/2002 | Leight et al. |
| 2002/0168618 A1 | 11/2002 | Anderson et al. |
| 2002/0191000 A1 | 12/2002 | Henn |
| 2003/0031993 A1 | 2/2003 | Pugh |
| 2003/0055380 A1 | 3/2003 | Flaherty |
| 2003/0065278 A1 | 4/2003 | Rubinstenn et al. |
| 2003/0108853 A1 | 6/2003 | Chosack et al. |
| 2003/0114842 A1 | 6/2003 | DiStefano |
| 2003/0164401 A1 | 9/2003 | Andreasson et al. |
| 2003/0220557 A1 | 11/2003 | Cleary et al. |
| 2004/0009459 A1 | 1/2004 | Anderson et al. |
| 2004/0092878 A1 | 5/2004 | Flaherty |
| 2004/0118225 A1 | 6/2004 | Wright et al. |
| 2004/0126746 A1 | 7/2004 | Toly |
| 2004/0175684 A1 | 9/2004 | Kaasa et al. |
| 2004/0234933 A1 | 11/2004 | Dawson et al. |
| 2005/0055241 A1 | 3/2005 | Horstmann |
| 2005/0057243 A1 | 3/2005 | Johnson et al. |
| 2005/0070788 A1 | 3/2005 | Wilson et al. |
| 2005/0084833 A1 | 4/2005 | Lacey et al. |
| 2005/0181342 A1 | 8/2005 | Toly |
| 2005/0203380 A1 | 9/2005 | Sauer et al. |
| 2006/0084050 A1 | 4/2006 | Haluck |
| 2006/0085068 A1 | 4/2006 | Barry |
| 2006/0194180 A1 | 8/2006 | Bevirt et al. |
| 2006/0264745 A1 | 11/2006 | Da Silva |
| 2006/0264967 A1 | 11/2006 | Ferreyro et al. |
| 2007/0003917 A1 | 1/2007 | Kitching et al. |
| 2007/0150247 A1 | 6/2007 | Bodduluri |
| 2007/0179448 A1 | 8/2007 | Lim et al. |
| 2007/0197954 A1 | 8/2007 | Keenan |
| 2007/0219503 A1 | 9/2007 | Loop et al. |
| 2007/0238981 A1 | 10/2007 | Zhu et al. |
| 2008/0038703 A1 | 2/2008 | Segal et al. |
| 2008/0097378 A1 | 4/2008 | Zuckerman |
| 2008/0107305 A1 | 5/2008 | Vanderkooy et al. |
| 2008/0123910 A1 | 5/2008 | Zhu |
| 2008/0138781 A1 | 6/2008 | Pellegrin et al. |
| 2008/0176198 A1 | 7/2008 | Ansari et al. |
| 2008/0177174 A1 | 7/2008 | Crane |
| 2008/0194973 A1 | 8/2008 | Imam |
| 2008/0270175 A1 | 10/2008 | Rodriguez et al. |
| 2009/0036902 A1 | 2/2009 | Dimaio et al. |
| 2009/0043253 A1 | 2/2009 | Podaima |
| 2009/0046140 A1 | 2/2009 | Lashmet et al. |
| 2009/0061404 A1 | 3/2009 | Toly |
| 2009/0074262 A1 | 3/2009 | Kudavelly |
| 2009/0081619 A1 | 3/2009 | Miasnik |
| 2009/0081627 A1 | 3/2009 | Ambrozio |
| 2009/0123896 A1 | 5/2009 | Hu et al. |
| 2009/0142741 A1 | 6/2009 | Ault et al. |
| 2009/0161827 A1 | 6/2009 | Gertner et al. |
| 2009/0208915 A1 | 8/2009 | Pugh |
| 2009/0221908 A1 | 9/2009 | Glossop |
| 2009/0263775 A1 | 10/2009 | Ullrich |
| 2009/0265671 A1 | 10/2009 | Sachs et al. |
| 2009/0275810 A1 | 11/2009 | Ayers et al. |
| 2009/0278791 A1 | 11/2009 | Slycke et al. |
| 2009/0305213 A1 | 12/2009 | Burgkart et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167250 A1 | 7/2010 | Ryan et al. |
| 2010/0167254 A1 | 7/2010 | Nguyen |
| 2010/0179428 A1 | 7/2010 | Pederson et al. |
| 2010/0198141 A1 | 8/2010 | Laitenberger et al. |
| 2010/0273135 A1 | 10/2010 | Cohen |
| 2011/0027767 A1 | 2/2011 | Divinagracia |
| 2011/0046915 A1 | 2/2011 | Hol et al. |
| 2011/0060229 A1 | 3/2011 | Hulvershorn et al. |
| 2011/0071419 A1 | 3/2011 | Liu et al. |
| 2011/0144658 A1 | 6/2011 | Wenderow et al. |
| 2011/0170752 A1 | 7/2011 | Martin et al. |
| 2011/0202012 A1 | 8/2011 | Bartlett |
| 2011/0207102 A1 | 8/2011 | Trotta et al. |
| 2011/0236866 A1 | 9/2011 | Psaltis et al. |
| 2011/0257596 A1 | 10/2011 | Gaudet |
| 2011/0269109 A2 | 11/2011 | Miyazaki |
| 2011/0282188 A1 | 11/2011 | Burnside et al. |
| 2011/0294103 A1 | 12/2011 | Segal et al. |
| 2011/0301500 A1 | 12/2011 | Maguire et al. |
| 2011/0306025 A1 | 12/2011 | Sheehan et al. |
| 2012/0002014 A1 | 1/2012 | Walsh |
| 2012/0015336 A1 | 1/2012 | Mach |
| 2012/0026307 A1 | 2/2012 | Price |
| 2012/0027269 A1 | 2/2012 | Fidaleo et al. |
| 2012/0034587 A1 | 2/2012 | Toly |
| 2012/0045743 A1 | 2/2012 | Okano et al. |
| 2012/0053514 A1 | 3/2012 | Robinson et al. |
| 2012/0082969 A1 | 4/2012 | Schwartz et al. |
| 2012/0130269 A1 | 5/2012 | Rea |
| 2012/0148994 A1 | 6/2012 | Hori et al. |
| 2012/0157800 A1 | 6/2012 | Tschen |
| 2012/0171652 A1 | 7/2012 | Sparks et al. |
| 2012/0183238 A1 | 7/2012 | Savvides et al. |
| 2012/0209243 A1 | 8/2012 | Yan |
| 2012/0214144 A1 | 8/2012 | Trotta et al. |
| 2012/0219937 A1 | 8/2012 | Hughes |
| 2012/0238875 A1 | 9/2012 | Savitsky et al. |

(56) References Cited

U.S. PATENT DOCUMENTS

| | | |
|---|---|---|
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0293632 A1 | 11/2012 | Yukich |
| 2012/0301858 A1 | 11/2012 | Park et al. |
| 2012/0323520 A1 | 12/2012 | Keal |
| 2013/0006178 A1 | 1/2013 | Pinho et al. |
| 2013/0018494 A1 | 1/2013 | Amini |
| 2013/0046489 A1 | 2/2013 | Keal |
| 2013/0100256 A1 | 4/2013 | Kirk et al. |
| 2013/0131503 A1 | 5/2013 | Schneider et al. |
| 2013/0179110 A1 | 7/2013 | Lee |
| 2013/0189658 A1 | 7/2013 | Peters et al. |
| 2013/0189663 A1 | 7/2013 | Tuchschmid et al. |
| 2013/0197845 A1 | 8/2013 | Keal |
| 2013/0198625 A1 | 8/2013 | Anderson |
| 2013/0203032 A1 | 8/2013 | Bardsley |
| 2013/0223673 A1 | 8/2013 | Davis et al. |
| 2013/0236872 A1* | 9/2013 | Laurusonis ......... G09B 23/285 434/262 |
| 2013/0267838 A1 | 10/2013 | Fronk et al. |
| 2013/0296691 A1 | 11/2013 | Ashe |
| 2013/0308827 A1 | 11/2013 | Dillavou et al. |
| 2013/0323700 A1 | 12/2013 | Samosky |
| 2013/0342657 A1 | 12/2013 | Robertson |
| 2014/0017650 A1 | 1/2014 | Romero |
| 2014/0039452 A1 | 2/2014 | Bangera et al. |
| 2014/0071165 A1 | 3/2014 | Tuchschmid et al. |
| 2014/0102167 A1 | 4/2014 | MacNeil et al. |
| 2014/0120505 A1* | 5/2014 | Rios ....................... G09B 23/30 434/219 |
| 2014/0121636 A1 | 5/2014 | Boyden et al. |
| 2014/0121637 A1 | 5/2014 | Boyden et al. |
| 2014/0129200 A1 | 5/2014 | Bronstein et al. |
| 2014/0142422 A1 | 5/2014 | Manzke et al. |
| 2014/0162232 A1 | 6/2014 | Yang et al. |
| 2014/0240314 A1 | 8/2014 | Fukazawa et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2014/0322683 A1 | 10/2014 | Baym et al. |
| 2014/0349263 A1 | 11/2014 | Shabat et al. |
| 2014/0349266 A1 | 11/2014 | Choi |
| 2014/0363801 A1 | 12/2014 | Samosky et al. |
| 2015/0031987 A1 | 1/2015 | Pameijer et al. |
| 2015/0049081 A1 | 2/2015 | Coffey et al. |
| 2015/0079545 A1 | 3/2015 | Kurtz |
| 2015/0079565 A1 | 3/2015 | Miller et al. |
| 2015/0080710 A1 | 3/2015 | Henkel et al. |
| 2015/0086955 A1 | 3/2015 | Poniatowski et al. |
| 2015/0182706 A1 | 7/2015 | Wurmbauer et al. |
| 2015/0206456 A1 | 7/2015 | Foster et al. |
| 2015/0262512 A1 | 9/2015 | Rios et al. |
| 2015/0314105 A1* | 11/2015 | Gasparyan ......... A61M 25/0693 604/117 |
| 2015/0352294 A1 | 12/2015 | O'Mahoney et al. |
| 2015/0359721 A1 | 12/2015 | Hagel et al. |
| 2015/0379899 A1 | 12/2015 | Baker et al. |
| 2015/0379900 A1 | 12/2015 | Samosky et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2016/0193428 A1 | 7/2016 | Perthu |
| 2016/0213856 A1* | 7/2016 | Despa ................... A61M 5/3146 |
| 2016/0293058 A1 | 10/2016 | Gaillot et al. |
| 2016/0324580 A1 | 11/2016 | Esterberg |
| 2016/0374902 A1 | 12/2016 | Govindasamy et al. |
| 2017/0053563 A1 | 2/2017 | Holloway |
| 2017/0178540 A1 | 6/2017 | Rios et al. |
| 2017/0186339 A1 | 6/2017 | Rios et al. |
| 2017/0245943 A1 | 8/2017 | Foster et al. |
| 2017/0252108 A1 | 9/2017 | Rios et al. |
| 2017/0254636 A1 | 9/2017 | Foster et al. |
| 2017/0316720 A1 | 11/2017 | Singh et al. |
| 2018/0012516 A1 | 1/2018 | Rios et al. |
| 2018/0068075 A1 | 3/2018 | Shiwaku |
| 2018/0197441 A1 | 7/2018 | Rios et al. |
| 2018/0225991 A1 | 8/2018 | Pedroso et al. |
| 2018/0240365 A1 | 8/2018 | Foster et al. |
| 2018/0261125 A1 | 9/2018 | Rios et al. |
| 2018/0261126 A1 | 9/2018 | Rios et al. |
| 2018/0271581 A1 | 9/2018 | OuYang et al. |
| 2018/0333543 A1 | 11/2018 | Diaz et al. |
| 2018/0338806 A1 | 11/2018 | Grubbs |
| 2019/0130792 A1 | 5/2019 | Rios et al. |
| 2020/0206424 A1 | 7/2020 | Rios et al. |
| 2020/0226951 A1 | 7/2020 | Rios et al. |
| 2021/0174706 A1 | 6/2021 | Rios et al. |
| 2021/0177518 A1 | 6/2021 | Rios et al. |
| 2021/0213205 A1 | 7/2021 | Karlsson et al. |
| 2022/0309954 A1 | 9/2022 | Rios et al. |
| 2023/0009855 A1 | 1/2023 | Rios et al. |

FOREIGN PATENT DOCUMENTS

| | | |
|---|---|---|
| CA | 2865236 A1 | 9/2013 |
| CN | 2751386 Y | 1/2006 |
| CN | 201213049 Y | 3/2009 |
| CN | 201359805 Y | 12/2009 |
| CN | 201465399 U | 5/2010 |
| CN | 101908294 A | 12/2010 |
| CN | 202159452 U | 3/2012 |
| CN | 102708745 A | 10/2012 |
| CN | 102737533 A | 10/2012 |
| CN | 104703641 A | 6/2015 |
| CN | 105118350 A | 12/2015 |
| CN | 205541594 U | 8/2016 |
| CN | 106710413 A | 5/2017 |
| CN | 107067856 A | 8/2017 |
| DE | 102004046003 A1 | 3/2006 |
| DE | 202005021286 U1 | 9/2007 |
| EP | 0316763 A1 | 5/1989 |
| EP | 1504713 A1 | 2/2005 |
| EP | 1723977 A1 | 11/2006 |
| EP | 1884211 A2 | 2/2008 |
| EP | 2425416 B1 | 3/2015 |
| EP | 2538398 B1 | 8/2015 |
| EP | 2756857 B1 | 5/2016 |
| GB | 2288686 B | 7/1997 |
| GB | 2309644 A | 8/1997 |
| GB | 2 309 644 B | 5/2000 |
| GB | 2508510 | 6/2014 |
| IN | 201202900 P1 | 11/2013 |
| JP | H10161522 A | 6/1998 |
| JP | H10260627 A | 9/1998 |
| JP | 2004-348095 A | 12/2004 |
| JP | 2006-189525 A | 7/2006 |
| JP | 2008-83624 A | 4/2008 |
| JP | 2011-113056 A | 6/2011 |
| JP | 2013-037088 A | 2/2013 |
| JP | 52-21420 | 6/2013 |
| JP | 2013-250453 A | 12/2013 |
| JP | 2014-153482 A | 8/2014 |
| KR | 2012009379 A | 2/2012 |
| KR | 20140047943 A | 4/2014 |
| KR | 10-1397522 B1 | 5/2014 |
| TW | 201207785 A | 2/2012 |
| WO | WO 96/16389 | 5/1996 |
| WO | WO 00/53115 | 9/2000 |
| WO | WO 02/083003 | 10/2002 |
| WO | WO 2005/083653 | 9/2005 |
| WO | WO 2005/089835 | 9/2005 |
| WO | WO 2007/109540 | 9/2007 |
| WO | WO 2008/005315 A2 | 1/2008 |
| WO | WO 2008/122006 A1 | 10/2008 |
| WO | WO 2009/023247 A1 | 2/2009 |
| WO | WO 2009/049282 | 4/2009 |
| WO | WO 2009/094646 | 7/2009 |
| WO | WO 2009/141769 | 11/2009 |
| WO | WO 2011/043645 | 4/2011 |
| WO | WO 2011/127379 | 10/2011 |
| WO | WO 2011/136778 | 11/2011 |

(56) References Cited

FOREIGN PATENT DOCUMENTS

| WO | WO 2012/075166 | 6/2012 |
| WO | WO 2012/088471 A1 | 6/2012 |
| WO | WO 2012/101286 | 8/2012 |
| WO | WO 2012/106706 | 8/2012 |
| WO | WO 2012/155056 | 11/2012 |
| WO | WO 2013/025639 | 2/2013 |
| WO | WO 2013/064804 | 5/2013 |
| WO | WO 2014/035659 | 3/2014 |
| WO | WO 2014/070799 | 5/2014 |
| WO | WO 2014/100658 | 6/2014 |
| WO | WO 2015/109251 | 7/2015 |
| WO | WO 2015/110327 A1 | 7/2015 |
| WO | WO 2015/136564 | 9/2015 |
| WO | WO 2015/138608 | 9/2015 |
| WO | WO 2015/171778 | 11/2015 |
| WO | WO 2016/089706 | 6/2016 |
| WO | WO 2016/123144 A2 | 8/2016 |
| WO | WO 2016/162298 | 10/2016 |
| WO | WO 2016/191127 | 12/2016 |
| WO | WO 2017/048929 A1 | 3/2017 |
| WO | WO 2017/048931 A1 | 3/2017 |
| WO | WO 2017/050781 A1 | 3/2017 |
| WO | WO 2017/060017 A1 | 4/2017 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |
| WO | WO 2017/153077 | 9/2017 |
| WO | WO 2018/136901 | 7/2018 |

OTHER PUBLICATIONS

"Accelerometer: Introduction to Acceleration Measurement," Omega Engineering, Sep. 17, 2015, 3 pages, https://www.omega.com/prodinfo/accelerometers.html.

Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.

Andraos et al., "Sensing your Orientation" Address 2007, 7 pp.

Arms, S.W., "A Vision for Future Wireless Sensing Systems," 44 pp., 2003.

"B-Smart disposable manometer for measuring peripheral nerve block injection pressures", Bbraun USA, 2016, in 4 pages.

Bao, et al., "A Novel Map-Based Dead-Reckoning Algorithm for Indoor Localization", J. Sens. Actuator Networks, 2014, 3, 44-63; doi:10.3390/jsan3010044, 20 pp., Jan. 3, 2014.

Benbasat et al., "An Inertial Measurement Framework for Gesture Recognition and Applications," I. Wachsmuth and T. Sowa (Eds.): GW 2001, Springer-Verlag Berlin Heidelberg, 12 pp., 2002.

Bergamini et al., "Estimating Orientation Using Magnetic and Inertial Sensors and Different Sensor Fusion Approaches: Accuracy Assessment in Manual and Locomotion Tasks", Oct. 2014, 18625-18649.

Brunet et al., "Uncalibrated Stereo Vision," A CS 766 Project, University of Wisconsin-Madison, 6 pp, Fall 2004, http://pages.cs.wisc.edu/~chaol/cs766/.

Brunet et al., "Uncalibrated Stereo Vision," A CS 766 Project, University of Wisconsin-Madison, 13 pp, Fall 2004, http://pages.cs.wisc.edu/~chaol/cs766/.

Correa et al., "Virtual Reality Simulator for Dental Anesthesia Training in the Inferior Alveolar Nerve Block," Journal of Applied Oral Science, vol. 25, No. 4, Jul./Aug. 2017, pp. 357-366.

Desjardins, et al. "Epidural needle with embedded optical fibers for spectroscopic differentiation of tissue: ex vivo feasibility study", Biomedical Optics Express, vol. 2(6): pp. 1-10. Jun. 2011.

"EPGL Medical Invents Smart Epidural Needle, Nerve Ablation And Trigger Point Treatment Devices: New Smart Medical Devices Will Give Physicians Advanced Situational Awareness During Critical Procedures," EPGL Medical, dated Aug. 12, 2013, in 3 pages. Retrieved from http://www.prnewswire.com/news-releases/epgl-medical-invents-smart-epidural-needle-nerve-ablation-and-trigger-point-treatment-devices-219344621.html#.

"The EpiAccess System: Access with Confidence", EpiEP Epicardial Solutions, dated 2015, in 2 pages.

Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.

Garg et al., "Radial Artery cannulation—Prevention of pain and Techniques of cannulation: review of literature," The Internet Journal of Anesthesiology, vol. 19, No. 1, 2008, in 6 pages.

Grenet et al., "spaceCoder: a Nanometric 3D Position Sensing Device," CSEM Scientific & Technical Report, 1 page, 2011.

Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.

Inition. Virtual Botox: Haptic App Simulated Injecting The Real Thing. Retrieved from http://inition.co.uk/case-study/virtual-botox-haptic-app-simulates-injecting-real-thing.

International Search Report and Written Opinion for Appl. No. PCT/US2018/014748, dated Jun. 13, 2018, 22 pages.

Jafarzadeh et al., "Design and construction of an automatic syringe injection pump," Pacific Science Review A: Natural Science and Engineering 18, 2016, in 6 pages.

Kalvøy, H., et al., "Detection of intraneural needle-placement with multiple frequency bioimpedance monitoring: a novel method", Journal of Clinical Monitoring and Computing, Apr. 2016, 30(2):185-192.

Kettenbach et al., "A robotic needle-positioning and guidance system for CT-guided puncture: Ex vivo results," Minimally Invasive Therapy and Allied Technologies, vol. 23, 2014, in 8 pages.

Ladjal, et al., "Interactive Cell Injection Simulation Based on 3D Biomechanical Tensegrity Model," 2008 IEEE/RSJ International Conference on Intelligent Robots and Systems, in 9 pages.

Lee et al., "An Intravenous Injection Simulator Using Augmented Reality for Veterinary Education and its Evaluation," Proceedings of the 11th ACM SIGGRAPH International Conference on Virtual-Reality Continuum and its Applications in Industry, Dec. 2-4, 2012, in 4 pages.

Madgwick, Sebastian O.H., "An efficient orientation filter for inertial and inertial/magnetic sensor arrays," 32 pp., Apr. 30, 2010.

Microsoft, "Integrating Motion and Orientation Sensors," 85 pp., Jun. 10, 2013.

Miller, Nathan L., Low-Power, Miniature Inertial Navigation System with Embedded GPS and Extended Kalman Filter, MicroStrain, Inc., 12 pp., 2012.

MPU-9150 9-Axis Evaluation Board User Guide, Revision 1.0, 15 pp., May 11, 2011, http//www.invensense.com.

MPU-9150, Register Map and Descriptions, Revision 4.2, 52 pp., Sep. 18, 2013, http//www.invensense.com.

MPU-9150, Product Specification, Revision 4.3, 50 pp., Sep. 18, 2013, http//www.invensense.com.

Poyade et al., "Development of a Haptic Training Simulation for the Administration of Dental Anesthesia Based Upon Accurate Anatomical Data," Conference and Exhibition of the European Association of Virtual and Augmented Reality, 2014, in 5 pages.

PST Iris Tracker, Plug and Play, 3D optical motion tracking specifications, 1 p., Dec. 4, 2014, www.pstech.com.

PST Iris Tracker, Instruction Manual, 3D optical motion tracking specifications, 42 pp., Jul. 27, 2012, www.pstech.com.

Quio, "Smartinjector," available at https://web.archive.org/web/20161017192142/http://www.quio.com/smartinjector, Applicant believes to be available as early as Oct. 17, 2016, in 3 pages.

State Electronics, "Sensofoil Membrane Potentiometer," Product Information and Technical Specifications, in 6 pages.

Struik, Pieter, "Ultra Low-Power 9D Fusion Implementation: A Case Study," Synopsis, Inc., 7 pp., Jun. 2014.

Sutherland, et al. "An Augmented Reality Haptic Training Simulator for Spinal Needle Procedures," IEEE, 2011.

Truinject Corp., "Smart Injection Platform," http://truinject.com/technology/, printed Jan. 13, 2018, in 3 pages.

(56) References Cited

OTHER PUBLICATIONS

Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.

Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.

"About the Journal", *J. Dental Educ., AM. Dental Educ. Ass'n,* 2019, http://www.jdentaled.org/content/about-us (last visited Oct. 9, 2019).

Begg et al., "Computational Intelligence for Movement Sciences: Neural Networks and Other Emerging Techniques", Idea Group Inc (IGI), 2006.

Comsa et al., "Bioluminescene imaging of point sources implants in small animals post mortem: evaluation of a method for estimating source strength and depth", Phys. Med. Biol., Aug. 2007, vol. 52, No. 17, pp. 5415-5428.

Hotraphinyo et al., "Precision measurement for microsurgical instrument evaluation", Conference Proceedings of the 23rd Annual International Conference of the IEEE Engineering in Medicine and Biology Societyl, 2001, vol. 4, pp. 3454-3457.

International Preliminary Report on Patentability for Appl. No. PCT/US2018/014748, dated Aug. 1, 2019, 13 pages.

Krupa et al., "Autonomous 3-D positioning of surgical instruments in robotized laparoscopic surgery using visual servoing", IEEE Trans. Robotics and Automation, 2003, vol. 19, pp. 842-853.

Lee et al., "Augmented reality intravenous injection simulator based 3D medical imaging for veterinary medicine," The Veterinary Journal, 2013, vol. 196, No. 2, pp. 197-202.

Liu et al. "Robust Real-Time Localization of Surgical Instruments in the Eye Surgery Stimulator (EyeSi)", *Signal and Image Processing,* 2002.

Merril et al., "The Ophthalmic Retrobulbar Injection Simulator (ORIS): An Application of Virtual Reality to Medical Education", Proc. Ann. Symp. Comput. Med. Care, 1992, pp. 702-706.

Mukherjee et al., "A Hall Effect Sensor Based Syringe Injection Rate Detector", IEEE 2012 Sixth Int'l Conf. on Sensing Technol. (ICST), Dec. 18-21, 2012.

Petition for Inter Partes Review of U.S. Pat. No. 9,792,836, Pursuant to 35 U.S.C. §§311-19, 37 C.F.R. § 42.100 ET SEQ., IPR2020-00042, dated Oct. 11, 2019.

Patterson et al., "Absorption spectroscopy in tissue-simulating materials: a theoretical and experimental study of photon paths", Appl. Optics, Jan. 1995, vol. 34, No. 1, pp. 22-30.

Van Sickle et al., "Construct validation of the ProMIS simulator using novel laparoscopic suturing task", Surg Endosc, Sep. 2005, vol. 19, No. 9, pp. 1227-1231.

Wierinck et al., "Expert Performance on a Virtual Reality Simulation System", *71 J. Dental Educ.,* Jun. 2007, pp. 759-766.

Wik et al., "Intubation with laryngoscope versus transillumination performed by paramedic students on mainkins and cadavers", *Resuscitation,* Jan. 1997, vol. 33, No. 3, pp. 215-218.

3D Systems,"ANGIO Mentor Clinical Validations, The Role of Simulation in Boosting the learning Curve in EVAR Procedures," Journal of Surgical Education, Mar.-Apr. 2018, 75(2), pp. 1-2, accessed on Feb. 6, 2020, https://simbionix.com/simulators/clinical-validations/angio-mentor-clinical-validations/ (listing clinical validations completed on ANGIO Mentor from 2007 through 2018).

3D Systems, "Angio Mentor™," Product Brochure/Overview. 2015, 6 pp.

Ainsworth et al., "Simulation Model for Transcervical Laryngeal Injection Providing Real-time Feedback," Annals of Otology, Rhinology & Laryngology, 2014, col. 123 (12), pp. 881-886.

Association of American Medical Colleges, Medical Simulation in Medical Education: Results of an AAMC Survey (Sep. 2011) ("AAMC Survey"), in 48 pages.

"A Virtual Reality Based Joint Injection Simulator Phase III", https://www.sbir.gov/. Retreived Mar. 5, 2021, in 2 pages.

Banivaheb, Niloofar, "Comparing Measured and Theoretical Target Registration Error of an Optical Tracking System," Feb. 2015, Toronto, Ontario, 128 pp.

Berkelman et al., "Co-Located 3D Graphic and Haptic Display using Electromagnetic Levitation", The Institute of Electrical and Electronics Engineers, 2012 in 6 pages.

Blue Telescope, DAISEY Injector Simulator, Available athttps://www.bluetelescope.com/work/ipsen-injection-simulator. Blue Telescope Laboratories 2020, site visited Aug. 24, 2020.

Blum et al., "A Review of Computer-Based Simulators for Ultrasound Training," Society for Simulation in Healthcare, Apr. 2013, vol. 8, pp. 98-108.

Botden et al., "Suturing training in Augmented Reality: gaining proficiency in suturing skills faster," Surg Endosc, 2009, vol. 23, pp. 2131-2137.

Botden et al., "Augmented versus Virtual Reality Laparoscopic Simulation: What Is the Difference?," World J. Surgery, 31, 2007, 10 pp.

Botden et al., "Face validity study of the ProMIS Augmented Reality laparoscopic suturing simulator," Surgical Technology International, Feb. 2008, 17, 16 pp.

Botden et al., "What is going on in augmented reality simulation in laparoscopic surgery," Surgical Endoscopy 23, 2009, 1693-1700.

Bova et al.,"Mixed-Reality Simulation for Neurosurgical Procedures," Neurosurgery, Oct. 2013, vol. 73, No. 4, pp. S138-S145.

Brennan et al., "Classification of diffuse light emission profiles for distinguishing skin layer penetration of a needle-free jet injection," Biomedial Optics Express, Oct. 1, 2019, vol. 10, No. 10, pp. 5081-5092.

Brennan et al., "Light source depth estimation in porcine skin using spatially resolved diffuse imaging," *2016 38th Annual International Conference of the IEEE Engineering in Medicine and Biology Society* (EMBC), Orlando, FL, 2016, pp. 5917-5920.

Brett, et al., "Simulation of resistance forces acting on surgical needles," Proceedings of the Instiutional of Mechanical Engineers Part H Journal of Engineering in Medicine, Feb. 1997, vol. 211 Part H, pp. 335-347.

Buchanan, Judith Ann, "Use of Simulation Technology in Dental Education," Journal of Dental Education, 2001, vol. 65, No. 11, 1225-1231.

CAE Healthcare, "CAE ProMIS Laparoscopic Simulator," Product Brochure/Overview, 2012, 2 pp.

Capsulorhexis forceps only technique rehearsed on EYESi before OR (Feb. 10, 2010), https://www.youtube.com/watch?v=ySMI1Vq6Ajw.

Chui et al., "Haptics in computer-mediated simulation: Training in vertebroplasty," Simulation & Gaming, Dec. 2006, vol. 37, No. 4, pp. 438-451.

J. Clark et al., A quantitative scale to define endoscopic torque control during natural orifice surgery, 22 Minimally Invasive Therapy & Allied Technologies 17-25 (2013).

Coles et al., "Modification of Commercial Force Feedback Hardware for Needle Insertion Simulation", Studies in Health Technology and Informatics, 2011 in 1 page.

Coquoz et al., "Determination of depth of in vivo bioluminescent signals using spectral imaging techniques," Conference Proceedings of SPIE, 2003, vol. 4967, pp. 37-45, San Jose, CA.

Craig, Alan B., "Augmented Reality Hardware," Understanding Augmented Reality Chapters, 2013, Elsevier Inc., pp. 69-124.

Cumin et al.,"Simulators for use in anaesthesia," Anaesthesia, 2007, vol. 62, pp. 151-162.

Dang et al., "Development and Evaluation of an Epidural Injection Simulator with Force Feedback for Medical Training", Studies in Health Technology and Informatics, 2001, vol. 81., pp. 97-102.

A. D'Angelo et al., Use of decision-based simulations to assess resident readiness for operative independence, 209 Am J Surg. 132-39 (2015).

V. Datta et al., The relationship between motion analysis and surgical technical assessments, 184(1) Am J SURG.70-73 (2002).

Datta et al., "The use of electromagnatic motion tracking analysis to objectively measure open surgical skill in the laboratory-based model". vol. 193, No. 5, Nov. 2001, pp. 479-485.

(56) References Cited

OTHER PUBLICATIONS

Davenar123, DentSim (Mar. 18, 2008), https://www.youtube.com/watch?v=qkzXUHay1W0.
Decision Denying Institution of Inter Parties Review for IPRP2020-00042, U.S. Pat. No. 9,792,836, dated Apr. 14, 2020, in 20 pages.
Defendant SHDS, INC.'s(F/K/A Nestle Skin Health, Inc.) Second Supplemental Disclosure of Invalidity Contentions, Case No. 1:19-cv-00592-LPS-JLH, *Truinject Corp., v. Galderma, S.A., Galderma Laboratories, L.P., Nestle Skin Health, Inc.*, dated Mar. 5, 2021, in 6 pages.
Defendant SHDS, INC.'s(F/K/A Nestle Skin Health, Inc.) Final Invalidity Contentions, Case No. 1:19-cv-00592-LPS-JLH, *Truinject Corp., v. Galderma, S.A., Galderma Laboratories, L.P., Nestle Skin Health, Inc.*, dated Jun. 18, 2021, in 54 pages.
DentSim Educators, DentSim Classroom Introduction (Aug. 8, 2013), https://vimeo.com/79938695.
DentSimLab, Aha Moments—Dentsim Students explain how their dental skills are improving (Nov. 13, 2013), https://www.youtube.com/watch?v=02NgPmhg55Q.
Dine et al., "Improving cardiopulmonary resuscitation quality and resuscitation training by combining audiovisual feedback and debriefing," Crit Care Med, 2008 vol. 36, No. 10, pp. 2817-2822.
A. Dosis et al., Synchronized Video and Motion Analysis for the Assessment of Procedures in the Operating Theater, 140 Arch Surg. 293-99 (2005).
EPED Taiwan, EPED—Computerized Dental Simulator (CDS-100) (Jun. 9, 2014), https://www.youtube.com/watch?v=m8UXaV2ZSXQ.
Färber et al., "Needle Bending in a VR-Puncture Training System Using a 6DOF Haptic Device", Studies in Health Technology and Informatics, 2009, vol. 142, in 3 pages.
Ford et al.,"Impact of simulation-based learning on mediation error rates in critically ill patients," Intensive Care Med, 2010, vol. 36, pp. 1526-1531.
Franz et al., "Electromagnetic Tracking in Medicine—A Review of Technology, Validation, and Applications," IEEE, Transactions on Medical Imaging, Aug. 2014, vol. 33, No. 8, pp. 1702-1725.
Garrett et al., "High-Fidelity Patient Simulation: Considerations for Effective Learning," Teaching with Technoloyg: High-Fidelity Simulation, 2010, vol. 31, No. 5, pp. 309-313.
Gobbetti et al., "Catheter Insertion Simulation with co-registered Direct Volume Rendering and Haptic Feedback", Studies in Health Technology and Informatics, vol. 70, 2000 in 3 pages.
Gottlieb et al., "Faculty Impressions of Dental Students' Performance With and Without Virtual Reality Simulation," Journal of Dental Education, 2011, vol. 75, No. 11, pp. 1443-1451.
Gottlieb et al., "Simulation in Dentistry and Oral Health," The Comprehensive Textbook of Healthcare Simulation Chapter 21, Apr. 2013, pp. 329-340.
Hoffman et al., "Arytenoid Repositioning Device," Annals of Otology, Rhinology & Laryngology, 2014, vol. 123 (3); pp. 195-205.
Hoffman et al., "Transillumination for Needle Localization in the Larynx," The Laryngoscope, 2015, vol. 125, pp. 2341-2348.
Huang et al., "CatAR: A Novel Stereoscopic Augmented Reality Cataract Surgery Training System with Dexterous Instrument Tracking Technology," CHI' 18: Proceedings of the 2018 CHI Conference on Human Factors in Computing Systems, Apr. 21-26, 2018, pp. 1-12, ACM, Montréal, Canada.
IDA Design Awards—Winners, DAISEY Injection Simulator, available at https://idesignawards.com/winners/zoom.php?eid=9-11737-16&count=0&mode=, Available as early as Sep. 7, 2016.
Image Navigation, DentSim by Image Navigation—Augmented Reality Dental Simulation, Nov. 2014, 5 pp., available at https://image-navigation.com/wp-content/uploads/2014/11/DentSim-V5-2-Pager.pdf.
Image Navigation, DentSim Computerized Dental Training Simulator, Product Brochure, Jul. 2014, available at https://image-navigation.com/wp-content/uploads/2014/07/DentsimBrochure.pdf.
"Immersion Medical Joins with PICC Excellence to Promote Training Products for Peripherally Inserted Central Catheter Procedure", Immersion Corporation, Business Wire 2006. Dated Jan. 9, 2006, in 3 pages.
"Immersion Medical Upgrades CathSim AccuTouch", Med Device Online, dated Jan. 12, 2005 in 1 page.
Invensense, Inc., "MPU-9150 EV Board User Guide," May 11, 2011, pp. 1-15.
Invensense, Inc., "MPU-9150 Product Specification Revision 4.3," Sep. 18, 2013, pp. 1-50.
Invensense, Inc., "MPU-9150 Register Map and Descriptions Revision 4.2," Sep. 18, 2013, pp. 1-52.
Jasinevicius et al., "An Evaluation of Two Dental Simulation Systems: Virtual Reality versus Contemporary Non-Computer-Assisted," Journal of Dental Education, 2004, vol. 68, No. 11, 1151-1162.
Judgment and Final Written Decision Determing All Challenged Claims Unpatentable, U.S. Pat. No. 10,290,231B2, IPR2020-00935.
Judgment and Final Written Decision Determing All Challenged Claims Unpatentable, U.S. Pat. No. 10,290,232B2, IPR2020-00937.
Kandani et al., "Development in blood vessel searching system for HMS," SPIE, Infrared Systems and Photoelectronic Tehcnology III, 2008, vol. 7065, pp. 1-10.
Khosravi, Sara, "Camera-Based Estimation of Needle Pose for Ultrasound Percutaneous Procedures," University of British Columbia, 2008, pp. ii-83.
Kumar et al., "Virtual Instrumentation System With Real-Time Visual Feedback and Needle Position Warning Suitable for Ophthalmic Anesthesia Training," IEEE: Transactions on Instrumentation and Measurement, May 2018, vol. 67, No. 5, pp. 1111-1123.
Lacey et al., "Mixed-Reality Simulation of Minimally Invasive Surgeries," IEEE Computer Society, 2007, pp. 76-87.
Laerdal, "Virtual I.V.—Directions for Use", www.laerdal.com, dated Sep. 3, 2010, in 103 pages.
Laerdal, "Virtual I.V. Sell Sheet", www.laerdal.com, dated Mar. 26, 2013, in 2 pages.
Laerdal, "Virtual I.V. Simulator (Discontinued)", www.laerdal.com, in 5 pages. Retrieved Jul. 23, 2021.
Laerdal, "Virtual Phlebotomy—Directions for Use," Self-directed Phlebotomy learning, Aug. 4, 2020, pp. 1-100.
Laerdal Medical, http://www.laerdal.com/us/nav/203/Venous-Arterial-Access, printed Mar. 8, 2019 in 3 pgs.
Lampotang et al.,"A Subset of Mixed Simulations: Augmented Physical Simulations with Virtual Underlays," Interservice/Idnustry Training, Simualtion, and Education Conference (I/ITSEC), 2012, pp. 1-11.
Lance Baily, Polhemus Delivers World Class Motion Tracking Technology to Medical Simulation Industry,healthysimulation.com,(May 2, 2016),https://www.healthysimulation.com/8621/polhemus-deliversworld-class-motion-tracking-technology-to-medical-simulationindustry/.
Lampotang et al., "Mixed Reality Simulation for Training Reservists and Military Medical Personnel in Subclavian Central Venous Access," Informational Poster, Ufhealth, Center for Safety, Simulation and Advanced Learning Technologies, 2015, 1 pp. available at https://simulation.health.ufl.edu/files/2018/12/Dept_CoR_2015-Mixed_Reality_Simulation_for_Training.pdf.
S. Laufer et al., Sensor Technology in Assessments of Clinical Skill, 372 N Engl Jmed 784-86 (2015).
"Learning by Feel: ToLTech and Allergan Simulator", 3D Systems, dated May 8, 2012, in 93 pages.
Lee et al., "A Phantom Study on the Propagation of NIR Rays under the Skin for Designing a Novel Vein-Visualizing Device," ICCAS, Oct. 20-23, 2013, pp. 821-823.
Lee et al., "Evaluation of the Mediseus® Epidural Simulator", Anaesthesia and Intensive Care (2012), vol. 40, No. 2, pp. 311-318.
Lee et al., "The utility of endovascular simulation to improve technical performance and stimulate continued interest of preclinical medical students in vascular surgery," Journal of Surgical Education, 2009 APDS Spring Meeting, vol. 66, No. 6, 367-373.

(56) References Cited

OTHER PUBLICATIONS

Lee et al., "Virtual Reality Ophthalmic Surgical Simulation as a Feasible Training and Assessment Tool: Results of a Multicentre Study," Canada Journal of Ophthalmology, Feb. 2011 vol. 46, No. 1, 56-60.
Lemole et al., "Virtual Reality in Neurosurgical Education: Part-Task Ventriculostomy Simulation with Dynamic Visual and Haptic Feedback," Neurosurgery, Jul. 2007, vol. 61, No. 1, pp. 142-149.
Lendvay et al., "The Biomechanics of Percutaneous Needle Insertion", Studies in Health Technology and Informatics, Jan. 2008 in 2 pages.
Leopaldi et al., "The dynamic cardiac biosimulator: A method fortraining physicians in beating-heart mitral valve repair procedures," The Journal of Thoracic and Cardiovascular Surgery, 2018, vol. 155, No. 1, pp. 147-155.
Lim et al., "Simulation-Based Military Regional Anesthesia Training System", US Army Medical Research and Materiel Command Fort Detrick MD, Telemedicine and Advanced Technology Research Center, 2008, in 8 pages.
Lim, M.W. et al., "Use of three-dimensional animation for regional anaesthesia teaching: application to interscalene brachial plexus blockade," British Journal of Anaesthesia, Advance Access, 2004, vol. 94, pp. 372-377.
Liu et al. "Study on an Experimental AC Electromagnetic Tracking System" Proceedings of the 5th World Congress on Intelligent Control and Automation, Jun. 15-19, 2001. pp. 3692-3695.
Luboz et al., "ImaGiNe Seidinger: First simulator for Seidinger technique and angiography training", Computer Methods and Programs in Biomedicine, vol. 111, No. 2, Aug. 2013 pp. 419-434.
Mastmeyer et al., "Direct Haptic vol. Rendering in Lumbar Puncture Simulation", Studies in Health Technology and Informatics, vol. 173, No. 280, 2012 in 8 pages.
Mastmeyer et al., "Real-Time Ultrasound Simulation for Training of US-Guided Needle Insertin in Breathing Virtual Patients", Studies in Health Technology and Informatics, Jan. 2016 in 9 pages.
Medgadget Editors, "EYESI Surgical Simulator," Medgadget, Aug. 28, 2006,4 pp., printed on Feb. 7, 2020, https://www.medgadget.com/2006/08/eyes_i_surgical.html.
Medgadget Editors, "ToLTech Cystoscopy Simulator Helps Practice BOTOX Injections", Medgadget, May 14, 2012, in 2 pages. Printed on Feb. 6, 2020, http://www.medgadget.com/2012/05/toltech-cystoscopy-simulator-helps-practice-botox-injections.html.
Merlone1, Eyesi_Cataract_2011 (Sep. 9, 2011), https://www.youtube.com/watch?v=XTulabWmEvk.
Mnemonic, Ipsen Injection Simulators, available at http://mnemonic.studio/project/ispen-injection-simulators. Copyright 2019, Website viewed on Aug. 24, 2020.
Mnemonic, Injection Simulator (Oct. 20, 2017), https://vimeo.com/239061418.
Mukherjee et al., "An Ophthalmic Anesthesia Training System Using Integrated Capacitive and Hall Effect Sensors," IEEE, Transactions on Instrumentation and Measurement, Jan. 2014, vol. 63, No. 5, 11 pp.
Nelson, Douglas A. Jr., "A Modular and Extensible Architecture Integrating Sensors, Dynamic Displays of Anatomy and Physiology, and Automated Instruction for Innovations in Clinical Education" Doctoral Dissertation, Univ. of Pitt., 2017, 260 pp.
Nelson et al., "The Tool Positioning Tutor: A Target-Pose Tracking and Display System for Learning Correct Placement of a Medical Device," *Medicine Meets Virtual Reality 18*, IOS Press, 2011, 5 pp.
Ottensmeyer et al., "Ocular and Craniofacial Trauma Treatment Training System: Overview & Eyelid Laceration Module," workshop Proceedings of the 8th International Conference on Intelligent Environments, IOS Press, 2012, 13 pp.
Ozturk wt al., "Complications Following Injection of Soft-Tissue Fillers," Aesthetic Surgery Journal, from the American Society for Aesthetic Plastic Surgery, Inc. Reprints and permissions, http://www.sagepub.com/journalsPermissions.nav, Aug. 2013, pp. 862-877.

K. Perrone et al., Translating motion tracking data into resident feedback: An opportunity for streamlined video coaching, 209 Am J Surg. 552-56 (2015).
Petition for Inter Partes Review of U.S. Pat. No. 9,792,836, Pursuant to 35 U.S.C. §§ 311-19, 37 C.F.R. § 42.100 ET SEQ., IPR2020-00042, dated Oct. 17, 2017.
C. Pugh et al., A Retrospective Review of TATRC Funding for Medical Modeling and Simulation Technologies, 6 Simulation in Healthcare, 218-25 (2011).
Petition for Inter Partes Review of U.S. Pat. No. 10,290,232, Pursuant to 35 U.S.C. §§ 311-19, 37 C.F.R. § 42.100 ET SEQ., IPR2020-00937 dated May 14, 2019.
Petition for Inter Partes Review of U.S. Pat. No. 10,290,231, Pursuant to 35 U.S.C. §§ 311-19, 37 C.F.R. § 42.100 ET SEQ., IPR2020-00935 dated May 14, 2019.
Pitt Innovates, BodyExplorer™ (Sep. 24, 2014), https://www.youtube.com/watch?v=T6G2OWJm5hs.
Pitt Innovates, Pitt Student Innovator Award, Pitt Intellectual Property 2017, Douglas A Nelson Jr. (Nov. 28, 2017), https://www.youtube.com/watch?v=0_CVBgWtCLo.
Rahman et al., "Tracking Manikin Tracheal Intubation Using Motion Analysis," Pediatric Emergency Care, Aug. 2011, vol. 27, No. 8, pp. 701-705.
Robinson et al., "A Mixed-Reality Part-Task Trainer for Subclavian Venous Access," Journal of the Society for Simulation in Healthcare, Feb. 2014, vol. 9, No. 1, pp. 56-64.
Salem et al., "Clinical Skills Laboratories "CSLs" Manual 1432-2011," Jan. 2011, pp. 0-88.
Samosky et al., "BodyWindows: Enhancing a Mannequin with Projective Augmented Reality for Exploring Anatomy, Physiology and Medical Procedures," Medicine Meets Virtual Reality 19, 2012, 433, J.D. Westwood et al. eds., IOS Press, pp. 433-439.
Samosky et al., "Enhancing Medical Device Training with Hybrid Physical-Virtual Simulators: Smart Peripherals for Virtual Devices," Medicine Meets Virtual Reality 20, Jan. 2013, J.D. Westwood et al. eds., IOS Press 377, pp. 377-379.
Samosky, Joseph, "View from the Top: Simulation Director Envisions Greater Use For Training Tool," Biomedical Instrumentation & Technology, 2012, pp. 283-288.
Samosky et al.,"Toward a Comprehensive Hybrid Physical-Virtual Reality Simulator of Peripheral Anesthesia with Ultrasound and Neurostimulator Guidance," Medicine Virtual Reality 18, IOS Press, 2011, pp. 552-554.
Satava, "Accomplishments and Challenges of Surgical Simulation", Dawning of the next-generation surgical education, Surgical Endoscopy Ultrasound and Interventional Techniques, Online publication, Feb. 6, 2001, in 10 pages.
Schneider, Chad Michael, "Systems for Robotic Needle Insertion and Tool-Tissue Interaction Modeling," Research Gate, 2004, pp. 1-74, Baltimore, Maryland.
Sclaverano et al. "BioSym : a simulator for enhanced learning of ultrasound-guided prostate biopsy", Studies in Health Technology and Informatics, 2009 in 6 pages.
S. Shaharan et al., Motion Tracking System in Surgical Training, 2017 INTECHOPEN 3-23 (2017), available at http://dx.doi.org/10.5772/intechopen.68850.
Shen et al., "Virtual trainer for intra-destrusor injection of botulinum toxin to treat urinary incontinence", Studies in Health Technology and Informatics, vol. 173, 2012 in 4 pages.
J. Šilar et al., Development of In-Browser Simulators for Medical Education: Introduction of a Novel Software Toolchain, 21 J Med Internet Res. e14160 (published online Jul. 3, 2019).
Simbionix, Valencia College's CVT program uses Simbionix ANGIO Mentor simulators, Feb. 26, 2013, https://www.youtube.com/watch?v=oAE0fWzXMjw.
SimEx, "Dental Augmented Reality Simulator," EPED, 3 pp. https://www.epedmed.com/simex. Available as early as 2019.
Spiteri et al., "Phacoemulsification Skills Training and Assessment," The British Journal of Ophthalmology 2010, Aug. 2009, 20 pp.
Stunt et al., "Validation of ArthroS virtual reality simulator for arthroscopic skills," Knee Surgery Sports Traum. Arthroscopy 23, Jun. 11, 2014, 8 pp.

(56) References Cited

OTHER PUBLICATIONS

Sultan et al.,"A Novel Phantom for Teaching and Learning Ultrasound-guided Needle Manipulation," Journal of Medical Ultrasound, Elsevier Taiwan LLC, Jul. 2013, vol. 21, pp. 152-155.
Suzuki et al., "Simulation of Endovascular Neurointervention Using Silicone Models: Imaging and Manipulation," Neurol Med Chir (Tokyo), 2005, vol. 45, pp. 567-573.
The Simulation Group, Internet Archive Wayback webpage capture of http://www.medicalsim.org/virgil.htm, apparently available Apr. 10, 2013, site visited Aug. 25, 2020.
The Simulation Group, VIRGIL™ Videos (2002), http://www.medicalsim.org/virgil_vid.htm; http://www.medicalsim.org/virgil/virgil%20expert.mpg.
Ting et al., "A New Technique to Assist Epidural Needle Placement: Fiberoptic-guided Insertion Using Two Wavelengths," Anesthesiology, 2010, vol. 112, pp. 1128-1135.
Touch of Life Technologies, "ToLTech Cystoscopy Simulator Helps Practice BOTOX Injections," https://www.medgadget.com/2012/05/toltech-cystoscopy-simulator-helps-practice-botox-injections.html, May 2012, printed on Feb. 6, 2020 in 2 pgs.
Touch of Life Technologies, "Touch of Life Technologies' new cystoscopy and bladder injection simulator offers urologists training on use of BOTOX®," https://www.urotoday.com/recent-abstracts/pelvic-health-reconstruction/urinary-incontinence/50289-touch-of-life-technologies-new-cystoscopy-and-bladder-injection-simulator-offers-urologists-training-on-use-of-botox-onabotulinumtoxina-as-treatment-for-urinary-incontinence-in-adults-with-neurological-conditions.html, May 2012, printed on Feb. 6, 2020 in 2 pgs.
Ufcssalt, "Video of mixed simulation for placement of CVL needle"—(Patent Pending), Dec. 5, 2011, https://www.youtube.com/watch?v=0ITIFbiiwRs.
UFhealth, "UF developing mixed-reality simulators fortraining in treatment of injured soldiers," Aug. 20, 2014, https://www.youtube.com/watch?v=sMxH1Iprc10& feature=emb_title.
Ungi et al., "Perk Tutor: An Open-Source Training Platform for Ultrasound-Guided Needle Insertions," IEEE Transactions on Biomedical Engineering, Dec. 2012, vol. 59, No. 12, pp. 3475-3481.
Univervisty of Pittsburgh Innovation Institute, "BodyExplorer: An Automated Augmented Reality Simulator for Medical Training and Competency Assessment," Mar. 2016, 2 pp.
Univervisty of Pittsburgh Innovation Institute, "BodyExplorer: Enhancing a Mannequin Medical Simulator with Sensing. Tangible Interaction and Projective Augmented Reality for Exploring Dynamic Anatomy, Physiology and Clinical Procedures," 2012, pp. 1-3.
Vaughan et al., "A review of virtual reality based training simulators for orthopedic surgery," Journal Engineering and Physics, 2016, vol. 38, Elsevier Ltd., pp. 59-71.
Vidal et al., "Developing An Immersive Ultrasound Guided Needle Puncture Simulator", Studies in Health Technology and Informatics, 2009, pp. 398-400.
Virgil™, the Simulation Group/Cimit, "Medical Simulation Chest Trauma Training System," 2002, 6 pp. http://www.medicalsim.org/virgil.htm.
VirtaMed ArthroS™, "Virtual reality arthroscopy for knee, shoulder, hip, ankle & FAST basic skills," Fact Sheet/Brochure Jul. 13, 2011.
VirtaMed ArthroS™ Module Descriptions. 2019.
VirtaMed, ArthroS—The 2012 Arthroscopic Simulator for Knee Arthroscopy, Feb. 1, 2012, https://www.youtube.com/watch?v=Y6w3AGfAqKA.
VirtaMed, Arthroscopy Training Simulator ArthroS Now With Shoulder Module!, Mar. 13, 2013, https://www.youtube.com/watch?v=kPuAm0MIYg0.
VirtaMed, Arthroscopy Training 2013: VirtaMed ArthroS Shoulder Simulator, Sep. 24, 2013, https://www.youtube.com/watch?v=WdCtPYr0wK0.
VirtaMed News, "VirtaMed ArthroS—Virtual reality training for knee arthroscopy," VirtaMed, Jul. 13, 2011, 2 pp. accessed on Feb. 6, 2020,https://www.virtamed.com/en/news/virtamed-arthros-virtual-reality-training-knee-arthroscopy/.
VirtaMed, VirtaMed ArthroS™—diagnostic and therapeutic arthroscopy in both the knee and shoulder (Apr. 15, 2014), https://www.youtube.com/watch?v=gtkISWnOzRc.
Virtual I.V.® Simulator—1. Introduction. YouTube, uploaded by Laerdal Medical AS, Jan. 19, 2011, www.youtube.com/watch?v=H9Qd6N9vG_A, viewed on Jul. 27, 2021.
Virtual I.V.® Simulator—2. System Overview. YouTube, uploaded by Laerdal Medical AS, Jan. 19, 2011, www.youtube.com/watch?v=I01UFNFU3cU, viewed on Jul. 28, 2021.
Virtual I.V.® Simulator—3. Training overview. YouTube, uploaded by Laerdal Medical AS, Jan. 19, 2011, www.youtube.com/watch?v=5Ut6YkDaNWI, viewed on Jul. 27, 2021.
VRmagic,"eyesi by VRmagic Surgical Simulator," Product Brochure, 2015, available at https://pdf.medicalexpo.com/pdf/vrmagic/eyesi-surgical-product-brochure/112458-159450.html.
Walsh et al., "Use of Simulated Learning Environments in Dentistry and Oral Health Curricula," SLE in Dentistry and Oral Health: Final Report, 2010, Health Workforce Australia, pp. 1-112.
Wandell et al., "Using a Virtual Reality Simulator in Phlebotomy Training", LabMedicine, ( Aug. 2010) vol. 41, No. 8, in 4 pages.
Welk et al., "DentSim—A Future Teaching Option for Dentists," 7 International Journal of Computerized Dentistry, 2004, 9 pp.
Wiles, Andrew et al., "Accuracy assessment and interpretation for optical tracking systems," SPIE, Medical Imaging: Visualization, Image-Guided Procedures and Display, 2004, vol. 5367, pp. 1-12.
Wolpert et al., "ENISS: An Epidural Needle Insertion Simulation System", Institute of Electrical and Electronics Engineers Inc., 2007 pp. 271-272.
Yeo et al., "The Effect of Augmented Reality Training on Percutaneous Needle Placement in Spinal Facet Joint Injections," IEEE, Transactions on Biomedical Engineering, Jul. 2011, vol. 58, No. 7, 8 pp.
Yu et al., "Development of an In Vitro Tracking System with Poly (vinyl alcohol) Hydrogel for Catheter Motion," Journal of Biomedical Science and Engineering, 2010, vol. 5, No. 1, 11-17.
Examination Report in corresponding European Patent Application No. 18704120.7, dated Apr. 7, 2021, in 4 pages.

\* cited by examiner

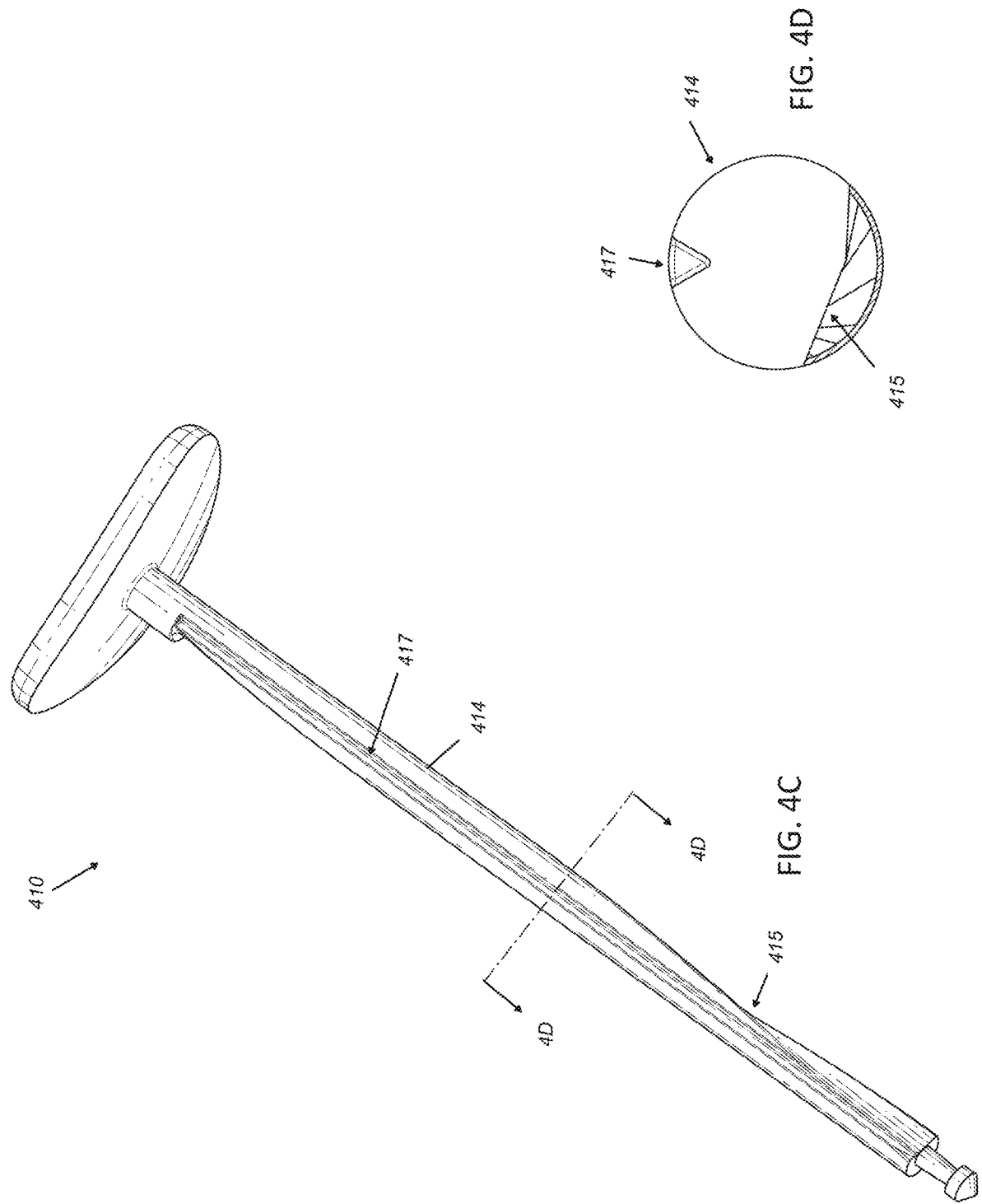

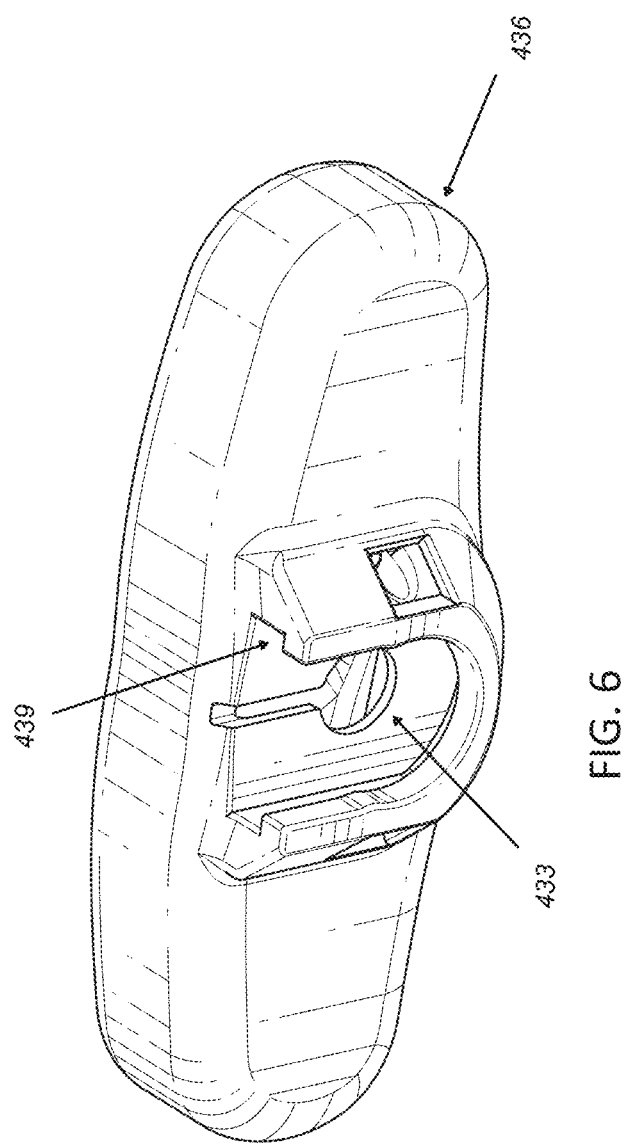

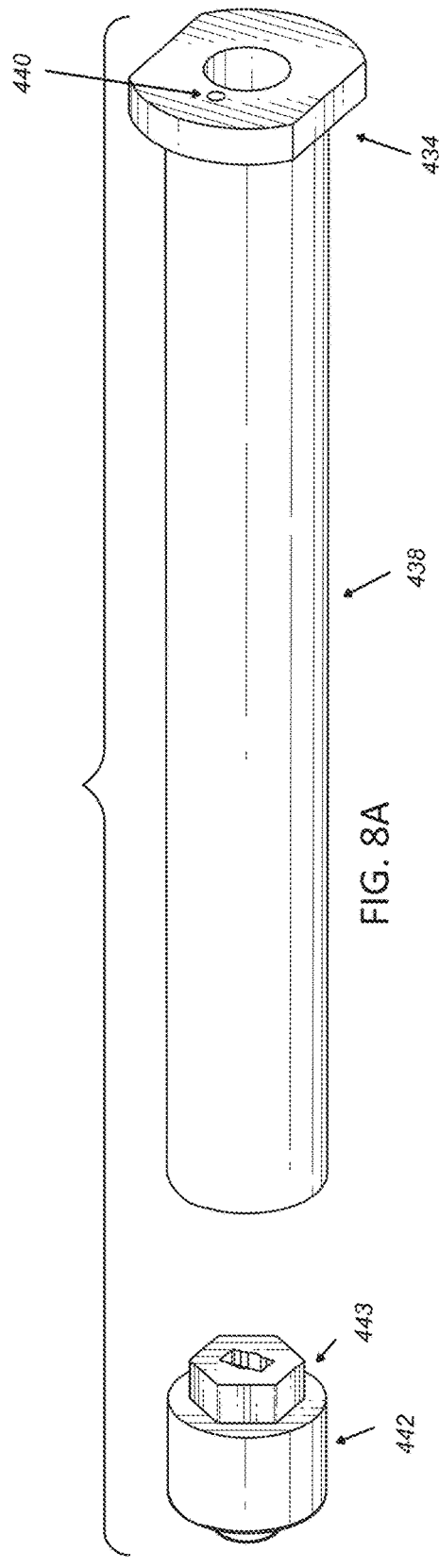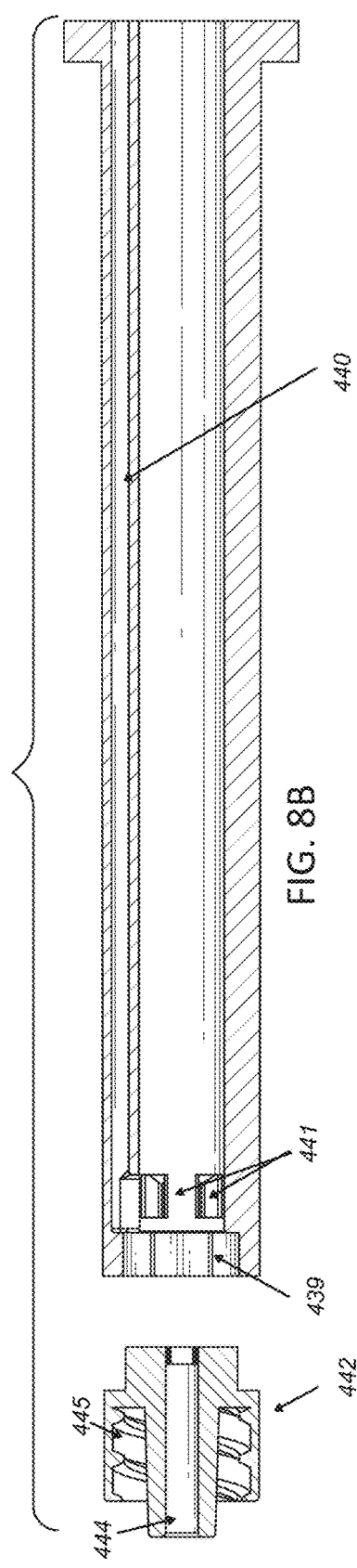

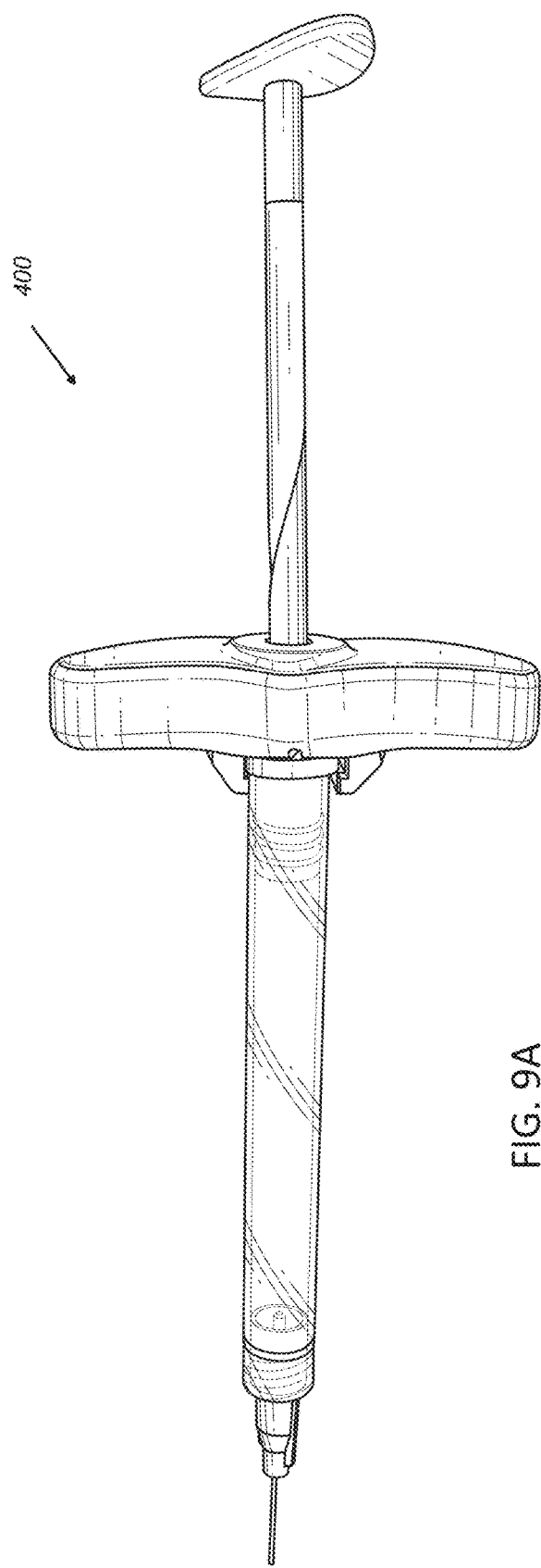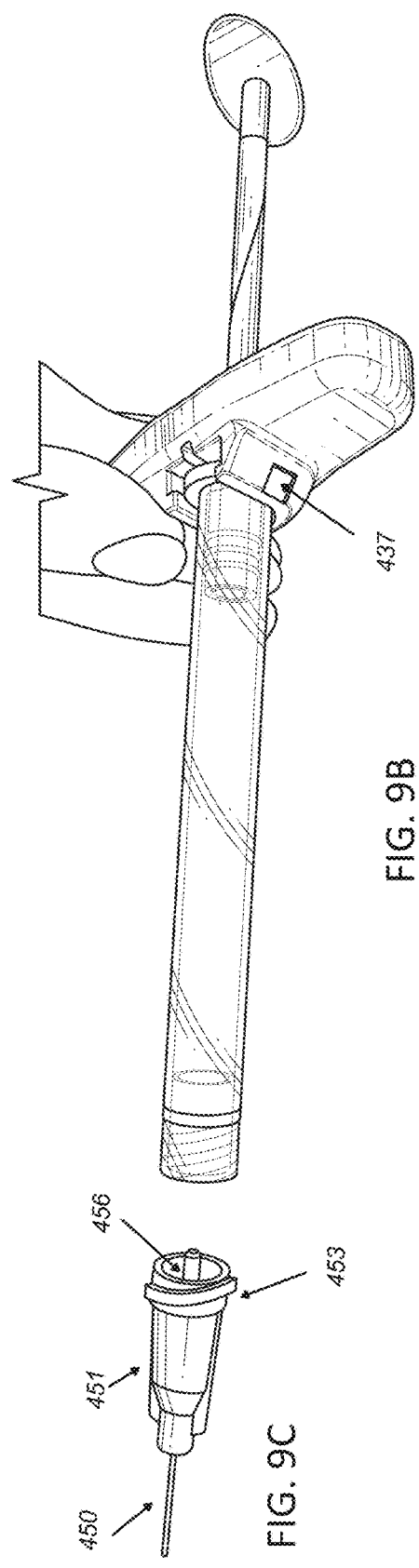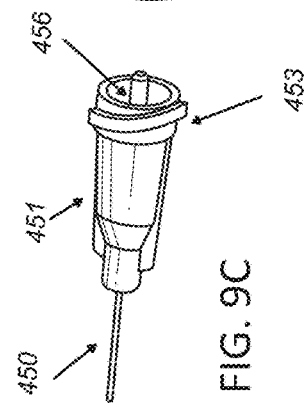
FIG. 9A
FIG. 9B
FIG. 9C

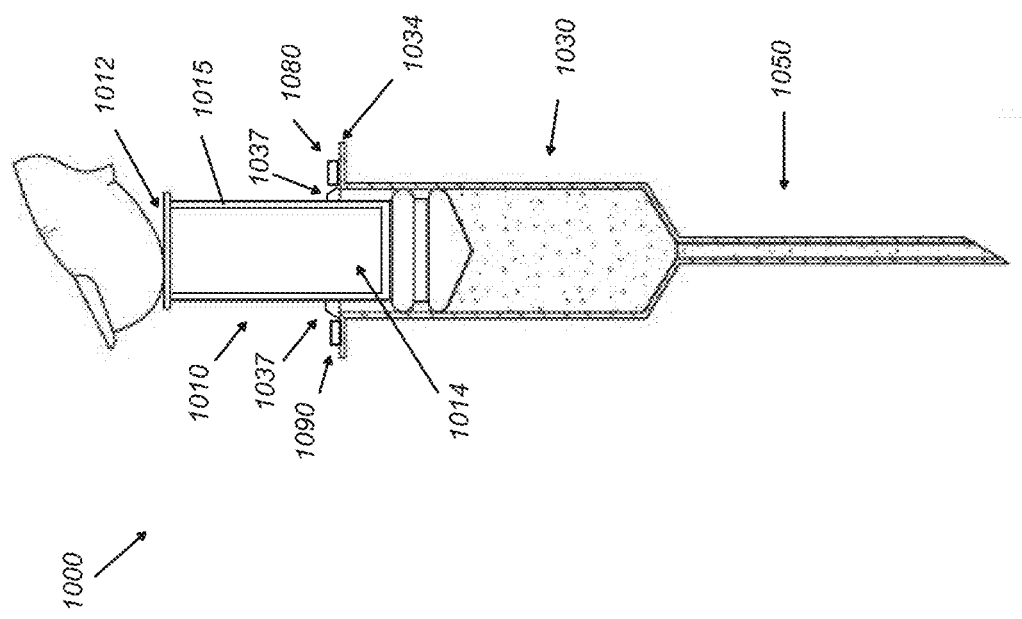

SYRINGE DOSE AND POSITION MEASURING APPARATUS

INCORPORATION BY REFERENCE TO ANY PRIORITY APPLICATIONS

This application is a continuation of U.S. patent application Ser. No. 16/296,110, filed Mar. 7, 2019, entitled "SYRINGE DOSE AND POSITION MEASURING APPARATUS," which is a division of U.S. patent application Ser. No. 15/877,310, filed Jan. 22, 2018, entitled "SYRINGE DOSE AND POSITION MEASURING APPARATUS," now U.S. Pat. No. 10,269,266, which claims benefit of U.S. Provisional Patent Application No. 62/449531, filed Jan. 23, 2017, and entitled "SYRINGE DOSE AND POSITION MEASURING APPARATUS," and U.S. Provisional Patent Application No. 62/552307, filed Aug. 30, 2017, and entitled "SYSTEMS AND METHODS OF INJECTION TRAINING," the entire disclosure of each of which is hereby incorporated by reference and made part of this specification.

Any and all applications for which a foreign or domestic priority claim is identified in the Application Data Sheet as filed with the present application are hereby incorporated by reference in their entirety under 37 CFR 1.57.

FIELD

The present disclosure generally relates to the field of injectable medication, in particular, to cosmetic and therapeutic injection and/or injection training devices and systems.

BACKGROUND

A variety of medical injection procedures are often performed in prophylactic, curative, therapeutic, or cosmetic treatments. Injections may be administered in various locations on the body, such as under the conjunctiva, into arteries, bone marrow, the spine, the sternum, the pleural space of the chest region, the peritoneal cavity, joint spaces, and internal organs. Injections can also be helpful in administering medication directly into anatomic locations that are generating pain. These injections may be administered intravenously (through the vein), intramuscularly (into the muscle), intradermally (beneath the skin), subcutaneously (into the fatty layer of skin), or by way of intraperitoneal injections (into the body cavity). Injections can be performed on humans as well as animals. The methods of administering injections typically vary for different procedures and may depend on the substance being injected, the needle size, or the area of injection.

Injections are not limited to treating medical conditions, such as cancer and dental treatment, but may be expanded to treating aesthetic imperfections, restorative cosmetic procedures, procedures for treating migraine, depression, lung aspirations, epidurals, orthopedic procedures, self-administered injections, in vitro procedures, or other therapeutic procedures. Many of these procedures are performed through injections of various products into different parts of the body. The aesthetic and therapeutic injection industry includes two main categories of injectable products: neuromodulators and dermal fillers. The neuromodulator industry commonly utilizes nerve-inhibiting products such as Botox®, Dysport®, and Xeomin®, among others. The dermal filler industry utilizes products administered by providers to patients for orthopedic, cosmetic and therapeutic applications, such as, for example, Juvederm®, Restylane®, Belotero®, Sculptra®, Artefill®, Voluma®, Kybella®, Durolane®, and others. The providers or injectors may include plastic surgeons, facial plastic surgeons, oculoplastic surgeons, dermatologists, orthopedist, primary care givers, psychologist/psychiatrist, nurse practitioners, dentists, and nurses, among others.

SUMMARY

The current state of the art utilizes a syringe with a cylindrical body and a plunger that moves within the body. The body has a discharge end that can attach to a needle or IV for delivery of medication. The dose of medication delivered is determined by viewing the plunger travel in relation to graduations visible on the clear wall of syringe body.

The present disclosure provides an improved syringe system for training, tracking, monitoring and providing feedback to a user. Some or all aspects of the injection systems and methods of the present disclosure can be used for both injection training and medication delivery injections in live patients.

The present disclosure can include an injection syringe of the injection system having a Syringe Dose and Position Apparatus (SDPA). The SDPA can have one or more printed circuit boards. The SDPA can be mounted to a syringe flange or be configured to be moved elsewhere on the syringe. The SDPA can have a controller, such as a microprocessor, and one or more sensors, such as plunger motion sensor, inertial navigation system (INS). The SDPA can include or be connected to a power source.

The SDPA can improve the knowledge of medication delivered. The knowledge can include, for example, the time of delivery, type of medication, the amount of medication delivered, the location of delivery, and/or the identity of the user to validate that the user purchased the medication product from a manufacturer with regulatory approval, such as with FDA approval in the US, with CE marks, or the regulatory bodies in other countries.

The SDPA can have a plunger motion sensor for measuring plunger travel that does not rely on viewing graduation. The plunger travel measurements can be made using various sensors, for example, a rotary potentiometer, a linear resistance potentiometer, a magnetometer, or the like. The sensor for plunger travel measurements can be at least partially located on the SDPA. The plunger travel measurements described herein are advantageous over relying on viewing graduations on the syringe body, which can be subjective and/or less accurate. The sensor-based plunger travel measurements can also be collected and recorded, which can include not only the dose, but also time of delivery, type of medication, location of delivery, identity of the user, authenticity of the product (for example, that the product is not imported) among other types of information.

Sensor-based injection systems and methods of the present disclosure can collect, process, analyze, and display other measured information associated with the delivery of an injection, including but not limited to measurements of a syringe's position and orientation in the three-dimensional space. The measured information can be obtained and processed to provide performance metrics of an injection procedure. The position and orientation measurement can be performed by an accelerometer, a gyroscope, a magnetometer, or a combination thereof.

The power source can supply power for the sensors, processors, communication components. The power source also optionally power a fiber optic embedded within the needle tip. Light emitted from the needle tip can be detected by one or more cameras inside an injection training anatomical model to also provide position and/or orientation information about the needle tip. One or more cameras external to the training model or live patient can also be used to track the location of the syringe.

The SDPA can also include one or more wireless communication components, such as Bluetooth, radiofrequency antenna, and the like. The collected injection information can be transmitted to a remote receiver. The collected injection information can also be combined with a digital model of a training apparatus to deliver a computer-generated, graphical depiction of the training procedure, enabling visualization of the injection from perspectives unavailable in the physical world. The performance metrics can be available at the time of the injection to guide the injector. The injection procedure, as reflected in the measured sensor-based data, can also be reviewed and analyzed at times after, and in locations different than, the time and location of the training injection. Additionally, injection data associated with multiple injections can be recorded, aggregated and analyzed for, among other things, trends in performance.

A flange of the present disclosure can be configured for use on an injection syringe. The flange can comprise a flange housing, wherein the flange housing includes an internal compartment; and at least one circuit board mounted within the internal compartment, wherein the at least one circuit board comprises one or more sensors, the one or more sensors configured to measure injection information about an injection procedure performed using the injection system. The flange can further comprise a flange base and a flange cover, wherein the flange base and flange cover are configured to be assembled to form the internal compartment. The flange base can be an integral part of a syringe body, the flange cover comprising one or more slots configured to slidably accommodate the flange base. The flange can be configured to be clipped onto a flange portion of the syringe. The flange base can comprise a slot on a distal surface, the slot configured to slidably accommodate the flange portion of the syringe. The flange can comprise an opening sized to accommodate a plunger of the syringe. The at least one circuit board can comprise a plunger travel sensor, a force sensor, a pressure sensor, a magnetic sensor, and/or a medication code reader. The at least one circuit board can comprise a first circuit board and a second circuit board. The first and second circuit boards can be stacked.

An injection system of the present disclosure can comprise a syringe having a syringe body and a plunger, the plunger configured to move relative to the syringe body, the syringe body configured to be coupled to a needle; the syringe body comprising a body portion having a proximal end and a distal end, a flange disposed at or near the proximal end, and a needle coupling portion disposed at or near the distal end; at least one circuit board mounted to the syringe body; and one or more sensors mounted to the syringe body and/or plunger and configured to measure injection information about an injection procedure performed using the injection system. The injection information can comprise one or more of: time of injection; type of medication; authenticity of medication; injection dose; identity of user of the system; and/or location of injection. The system can be configured for providing injection to a live patient and/or a training apparatus. The training apparatus can comprise an anatomical model. The one or more sensors can comprise one or more of: a position sensor, a potentiometer, an optical sensor, a force sensor, a pressure sensor, a magnetic sensor, and/or a medication code reader. At least one of the one or more sensors can be mounted on the at least one circuit board. The at least one circuit board can further comprise one or more controller. The at least one circuit board can be releasably attached to the syringe. The system can further comprise a housing for the at least one circuit board. The housing can be mounted to the flange of the syringe body. The housing can be clipped onto the flange. The at least one circuit board can comprise an opening configured to slidably accommodate the plunger. The system can further comprise a power source, wherein the at least one circuit board can be configured to be in electrical contact with the power source. The power source can be located within the housing. The at least one circuit board can comprise a first circuit board and a second circuit board. The first and second circuit boards can be at least partially stacked. The first circuit board can comprise at least one of the one or more sensors. The second circuit board can comprise a power management board. The first and second circuit boards can be mounted substantially to one side of the flange, and the power source can be mounted to a diametrically opposite side of the flange. The at least one circuit board can comprise a rotary sensor configured for measuring a plunger travel. A shaft of the plunger can comprise a helical groove such that a transverse cross-section of the shaft can be substantially D-shaped. The rotary sensor can be keyed to the D-shaped shaft such that a linear movement of the shaft relative to the syringe body causes rotation of the rotary sensor. The shaft can further comprise a channel substantially parallel to a longitudinal axis of the shaft. The rotary sensor can comprise a protrusion configured to engage the channel so as to prevent rotation of the rotary sensor upon rotation of the plunger without linear moving the plunger. The at least one circuit board can comprise two electrical contacts configured to measuring a plunger travel. The two electrical contacts can be biased radially inwardly. A shaft of the plunger can comprise a resistance strip, the two electrical contacts configured to be in contact with the resistance strip during linear movement of the plunger. The plunger travel measurement can be based at least in part on resistance changes measured between the two electrical contacts. The at least one circuit board can comprise a magnetic field sensor configured to measure changes in a magnetic field of a magnet located on the plunger, the plunger travel measurement based at least in part on the changes in the magnetic field. The dose measurement can be calculated as a product of the plunger travel and an internal cross-section area of the syringe body. The system can further comprise a light source at or near the distal end of the needle coupling portion of the syringe. The light source can comprise an LED. The light source can be powered by the power source. The syringe can comprise a wire lumen through a syringe wall, the wire lumen configured to accommodate an electrical connector connecting the power source and the light source. The system can further comprise a fiber optic extending between the light source and a tip of the needle. The fiber optic can be fused to a lumen of the needle. The fiber optic can comprise a diffuser layer at or near the tip of the needle. Light emitted from the needle tip can be configured to be detected by one or more light detectors located within a cavity of the training apparatus. The injection system can be configured to determine a three-dimensional position of the needle based at least in part on the light detected by the one or more light detectors. The injection system can be configured to determine a three-dimensional position and/or orientation of the syringe based at least in part on fusing data from the one or more light detectors and the position sensor. The system can further comprise a charging base, wherein the power source can be rechargeable by docking the syringe body onto the charging base. The syringe can comprise one or more electrical pads connected to the at least one circuit board. The charging base can comprise one or more electrical connectors, the electrical connectors configured to make contact with the electrical pads when the syringe body can be docked onto the charging base. The one or more electrical connectors can comprise pogo pins. The plunger can comprise a biometric sensor, the biometric sensor configured to detect identity of a person performing the injection. The biometric sensor can comprise a fingerprint sensor located on a thumb portion of the plunger. The at least one circuit board can comprise wireless communication connectors. The wireless communication connectors can comprise Bluetooth Low Energy. The system can further comprise a remote wireless receiver configured to receive data transmitted from the at least one circuit board. The system can further comprise a remote server configured to receive, analyze, and/or store data received by the remote wireless receiver. The system can further comprise a plunger stopper configured to apply a resistance to the plunger movement. The stopper can comprise a gear positioned at or near a path of the plunger movement. The stopper can be configured stop the plunger from moving when the system detects a predetermined dose has been delivered. The resistance can also be configured to simulate viscosity of the mediation.

An injection system of the present disclosure can comprise a syringe having a syringe body and a plunger, the plunger configured to move relative to the syringe body, the syringe body configured to be coupled to a needle; the syringe body comprising a body portion having a proximal end and a distal end, and a needle coupling portion disposed at or near the distal end; a flange disposed at or near the proximal end of the syringe body, the flange comprising an internal compartment; and at least one circuit board disposed within the internal compartment, wherein the at least one circuit board can comprise one or more sensors, the one or more sensors configured to measure injection information about an injection procedure performed using the injection system. The injection information can comprise one or more of time of injection; type of medication; authenticity of medication; injection dose; identity of user of the system; and/or location of injection. The system can be configured for providing injection to a live patient and/or a training apparatus. The training apparatus can comprise an anatomical model. The one or more sensors can comprise one or more of: a position sensor, a potentiometer, an optical sensor, a force sensor, a pressure sensor, a magnetic sensor, and/or a medication code reader. At least one of the one or more sensors can be mounted on the at least one circuit board. The system can further comprise a housing for the at least one circuit board. The housing can be releasably attached to the flange of the syringe body.

An injection system of the present disclosure can comprise a syringe having a syringe body and a plunger, the plunger configured to move relative to the syringe body, the syringe body configured to be coupled to a needle; and the syringe body comprising a body portion having a proximal end and a distal end, a flange disposed at or near the proximal end, and a needle coupling portion disposed at or near the distal end; wherein the flange can comprise a medication code containing information about a medication contained in the syringe body, and wherein the flange can be configured to mate with at least one circuit board, the circuit board comprising a medication code reader configured to obtain information from the medication code. The system can further comprise the at least one circuit board, wherein the at least one circuit board can comprise one or more additional sensors, the one or more additional sensors configured to measure injection information about an injection procedure performed using the injection system. The system can further comprise a housing for the at least one circuit board. The housing can be releasably attached to the flange of the syringe body.

An injection system of the present disclosure can comprise a syringe having a syringe body and a plunger, the syringe body configured to be coupled to a needle, the plunger configured to move relative to the syringe body, wherein the plunger comprises a plunger shaft having a helical groove along a longitudinal axis of the plunger shaft; the syringe body comprising a body portion having a proximal end and a distal end, a flange disposed at or near the proximal end, and a needle coupling portion disposed at or near the distal end; and a plunger travel sensor disposed on the flange, wherein the plunger travel sensor can comprise an opening sized and shaped to slidably engage the plunger shaft so that the plunger travel sensor rotates along the helical groove as the plunger shaft moves axially along the longitudinal axis of the plunger shaft, and wherein the plunger travel sensor can be configured to measure an axial plunger travel distance based on an amount of rotation of the plunger travel sensor. The plunger shaft can comprise a generally D-shaped transverse cross-section. The plunger travel sensor can comprise a bearing configured to rotate along the he helical groove as the plunger shaft moves axially along the longitudinal axis of the plunger shaft. The plunger travel sensor can be configured to measure the axial plunger travel distance based on an angular position of the bearing. The plunger shaft can comprise a channel running substantially parallel to the longitudinal axis. The plunger travel sensor can comprise a radially inward protrusion configured to engage the channel when the plunger shaft moves axially, the protrusion can remain stationary when the plunger shaft moves axially. The plunger travel sensor can be located on a circuit board. The circuit board can further comprise one or more additional sensors. The one or more additional sensors can comprise a position sensor, an optical sensor, a force sensor, a pressure sensor, a magnetic sensor, and/or a medication code reader. The system can further comprise a housing for the at least one circuit board. The housing can be releasably attached to the flange of the syringe body. The system can be configured to calculate a dose measurement based at least in part on the axial plunger travel distance. The system can further comprise a plunger stopper configured to apply a resistance to the plunger movement. The stopper can comprise a gear positioned at or near a path of the plunger movement. The stopper can be configured stop the plunger from moving when the system detects a predetermined dose has been delivered. The resistance can also be configured to simulate viscosity of the mediation.

An injection system of the present disclosure can comprise a syringe having a syringe body and a plunger, the syringe body configured to be coupled to a needle, the plunger configured to move axially relative to the syringe body; the syringe body comprising a body portion having a proximal end and a distal end, and a needle coupling portion disposed at or near the distal end; and a plunger travel sensor operably coupled to the plunger and/or the syringe body, the plunger travel sensor configured to measure an electrical resistance change when the plunger moves axially relative to the syringe body, the plunger travel sensor further configured to calculate a plunger travel distance based at least in part on the electrical resistance change. The plunger travel sensor can comprise a rotary sensor configured to be slidably coupled with the plunger, the plunger comprising a helical profile, the rotary sensor configured to rotate along the helical profile when the plunger moves axially relative to the syringe body, wherein the rotary sensor can be configured to determine the plunger travel distance based at least in part on an amount of rotation of the rotary sensor when the plunger moves axially relative to the syringe body. The plunger travel sensor can comprise a resistive strip disposed on the plunger and two electrical contacts disposed on the syringe body, the electrical contacts configured to be in contact with the resistive strip when the plunger moves relative to the syringe body. The system can be configured to detect a resistance increase as the plunger shaft moves distally and a resistance decrease as the plunger shaft moves proximally.

An injection system of the present disclosure can comprise a syringe having a needle, the needle comprising an optic fiber disposed within a lumen of the needle, the optic fiber terminating distally at or near a tip of the needle; the syringe further comprising a syringe body and a plunger, the plunger configured to move axially relative to the syringe body; and the syringe body comprising a body portion having a proximal end and a distal end, a flange portion at the proximal end, and a needle coupling portion disposed at or near the distal end, the syringe body further comprising a light source disposed at or near the distal end; wherein when the needle is coupled to the needle coupling portion of the syringe body, the optic fiber can be coupled to a power source so as to direct light emitted by the light source out through the tip of the needle, the power source also configured to power the light source. The optic fiber can extend proximally from a proximal end of the needle. The optic fiber can have a numerical aperture of at least about 0.37. The optic fiber can be fused with the lumen of the needle. The light source can comprise an LED. The needle can be releasably coupled with the needle coupling portion. The needle can be releasably coupled with the needle coupling portion by M3 threads. The power source can be mounted to the flange portion, the syringe body portion comprising a wire lumen, one or more lead wires extending from the power source through the wire lumen, the one or more lead wires terminating at or near the distal end of the syringe body portion. The needle can be configured to puncture a surface of a training apparatus, the training apparatus comprising an internal cavity and at least one light detector inside the internal cavity, the at least one light detector configured to detect light from the needle.

An injection system of the present disclosure can comprise a syringe having a syringe body and a plunger, the plunger configured to move relative to the syringe body, the syringe body configured to be coupled to a needle; the syringe body comprising a body portion having a proximal end and a distal end, and a needle coupling portion disposed at or near the distal end; a flange disposed at or near the proximal end of the syringe body, the flange comprising an internal compartment; at least one circuit board disposed within the internal compartment, wherein the at least one circuit board comprises one or more sensors, the one or more sensors configured to measure injection information about an injection procedure performed using the injection system; and a rechargeable power source configured to at least power the at least one circuit board. The system can further comprise a charging base. The charging base can comprise a cradle shaped to accommodate the syringe or a portion of the syringe. The flange can comprise at least one electrical contact in electrical connection with the at least one circuit board, and wherein the charging base can comprise at least one charging contact, the at least one electrical contact configured to make contact with the at least one charging contact when the syringe or a portion of the syringe is position on the charging base. The at least one charging contact can comprise at least one pogo pin.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. Corresponding numerals indicate corresponding parts.

FIG. 4C illustrates a plunger of the syringe of FIG. 4A.

FIG. 4D illustrates a transverse cross-section of the plunger of FIG. 4C.

FIG. 6 illustrates a perspective view of an SDPA housing base.

FIG. 8A illustrates an exploded view of a syringe body including a body portion and a needle-coupling portion.

FIG. 8B illustrates a cross-section of the syringe body of FIG. 8A.

FIG. 8C illustrates a bottom view of the body portion of the syringe body of FIG. 8A.

FIG. 8D illustrates a top view of the needle coupling portion of the syringe body of FIG. 8A.

FIG. 9A illustrates a top view of the injection syringe of FIG. 4A.

FIG. 9B illustrates the injection syringe of FIG. 4A with the needle removed.

FIG. 9C illustrates the needle of the syringe of FIG. 4A.

FIG. 10 illustrates schematically an example syringe with a linear resistance plunger motion sensor.

DETAILED DESCRIPTION

Aspects of the disclosure are provided with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit scope of the disclosure herein, which is instead defined by the claims following this description.

Example Injection Systems

The present disclosure provides various systems and methods of performing an injection procedure for actual medication delivery and/or injection training. Although the descriptions herein may be in the context of cosmetic facial injections, the injection systems and/or methods described herein can be configured for use in any part of the patient's body, any part of an animal's body, a training apparatus, and/or for any types of injections.

Figure 1A:
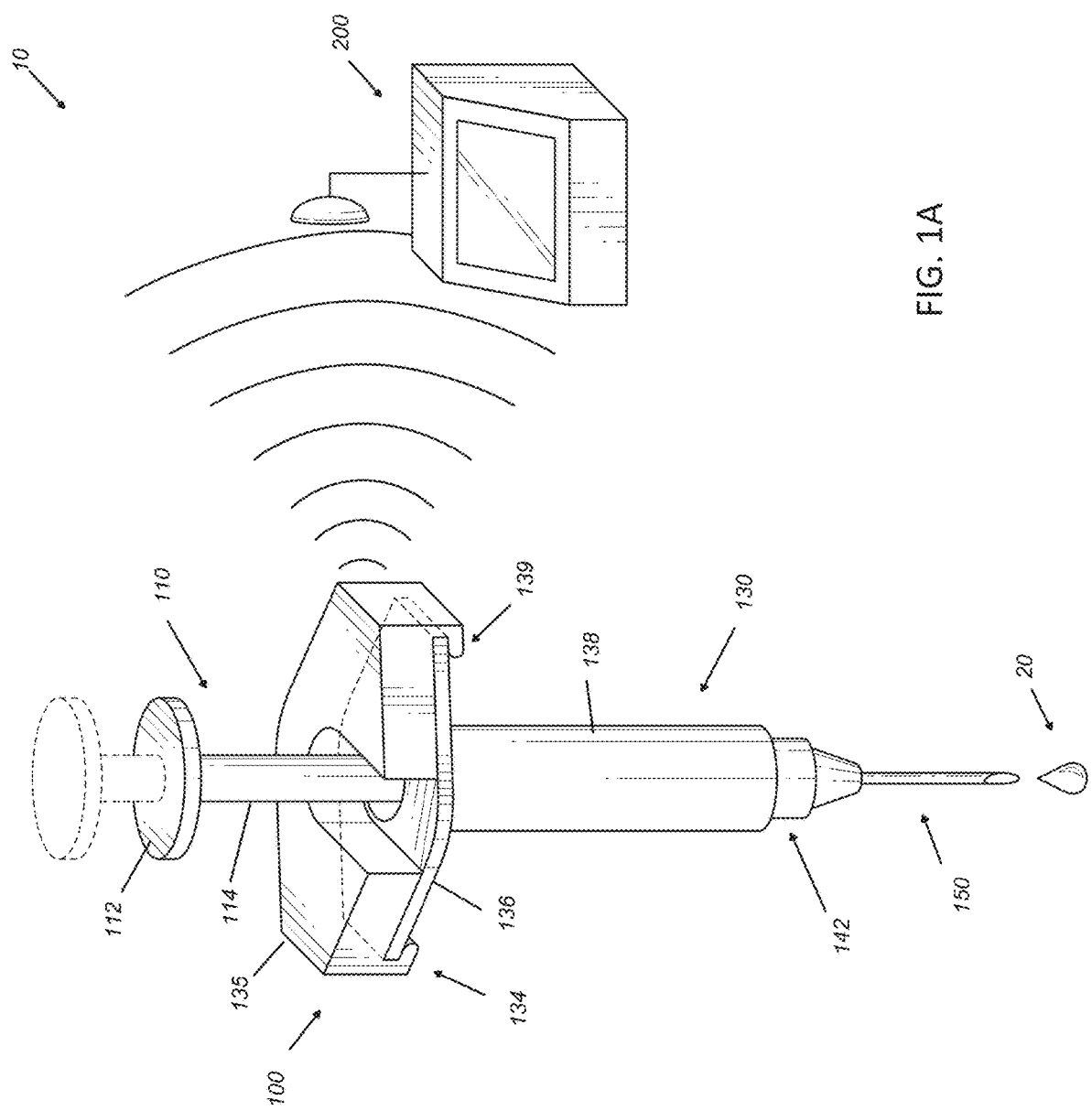
FIG. 1A illustrates schematically a perspective view of an example injection syringe and a remote receiver receiving data transmitted from the syringe.
Figure 1B:
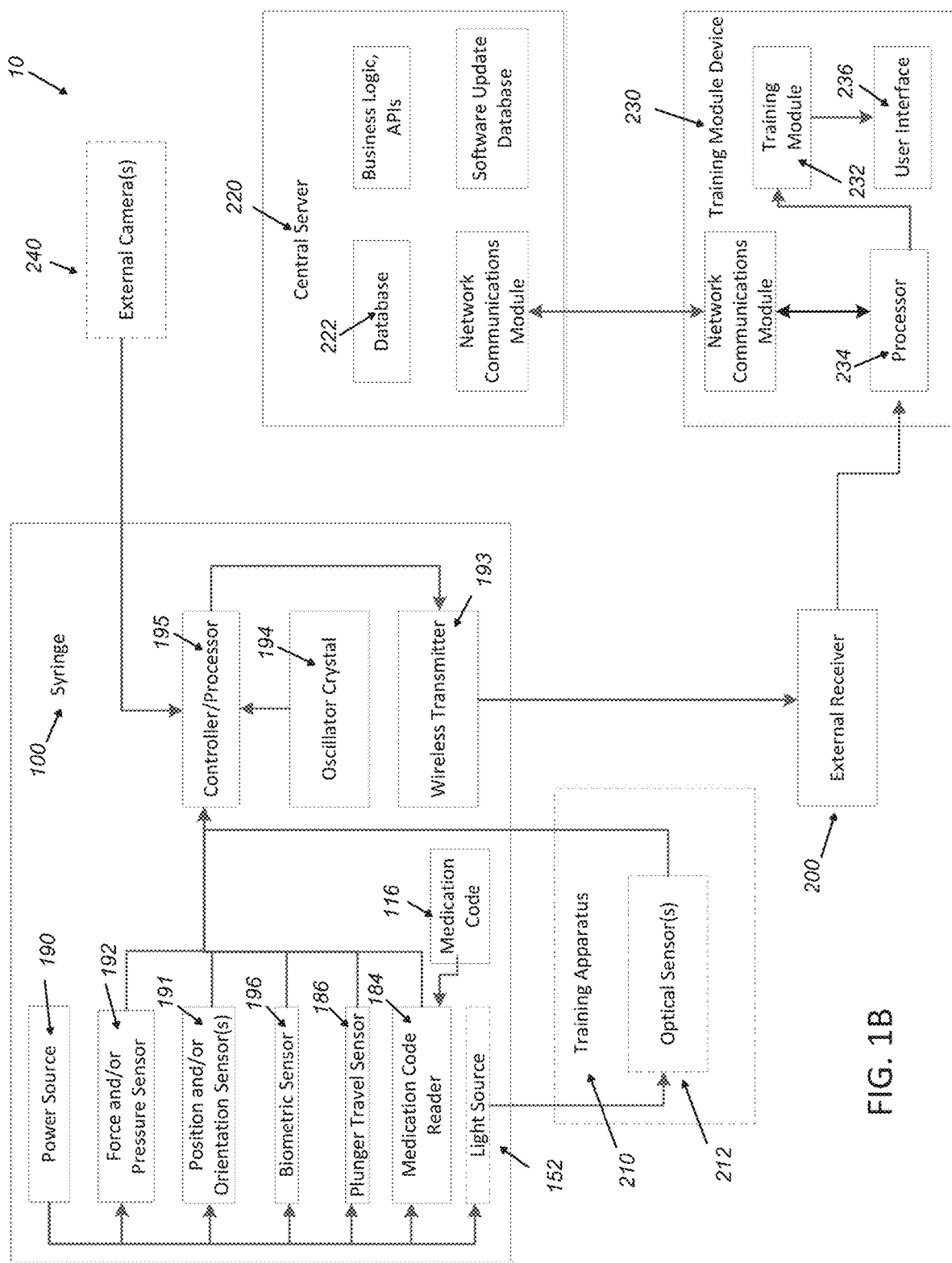
FIG. 1B illustrates schematically a system diagram of an injection system.
Figure 1C:
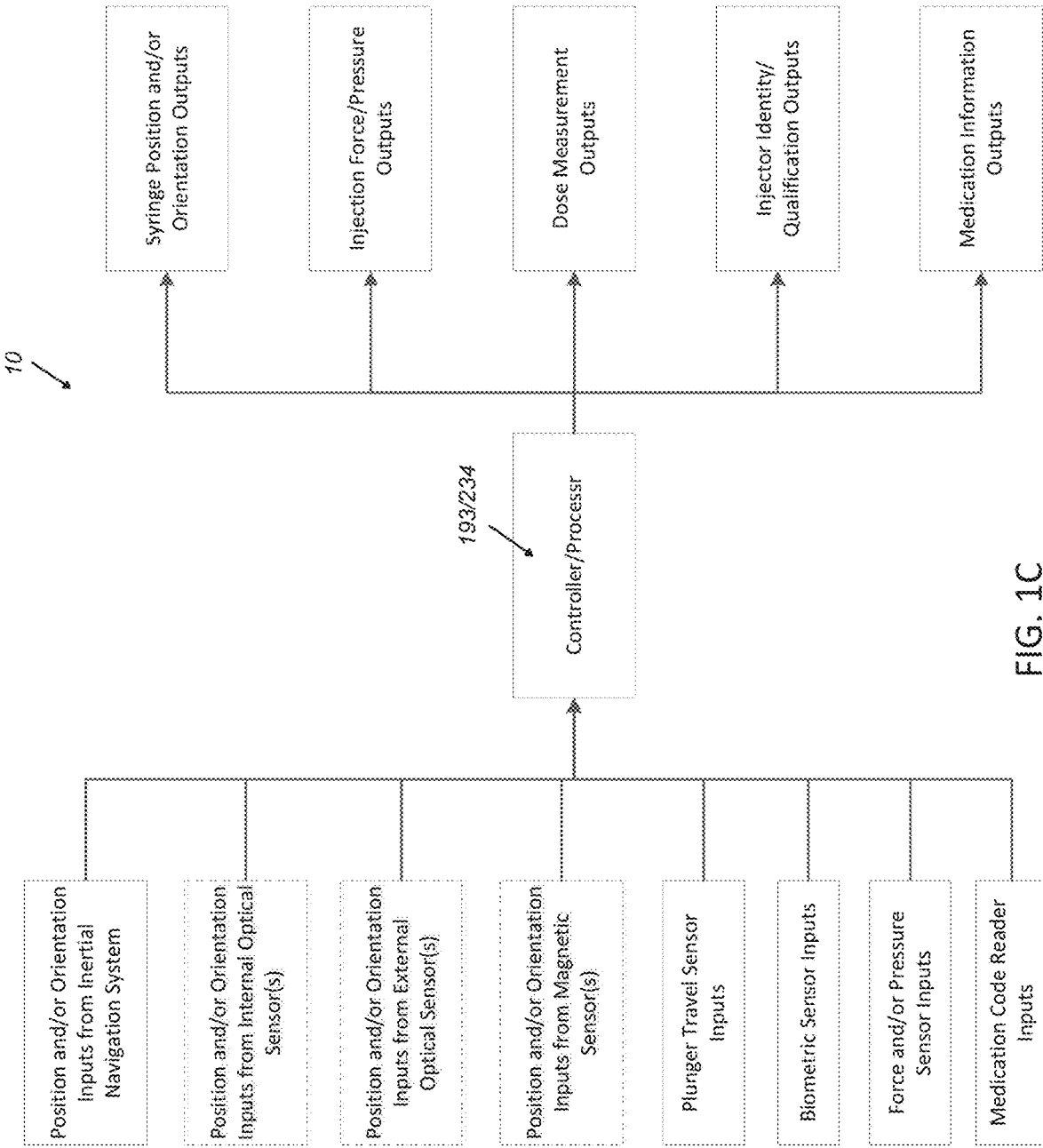
FIG. 1C illustrates schematically a block diagram of an injection system controller or processor interacting with sensor inputs and outputting injection information outputs.
Figure 2:
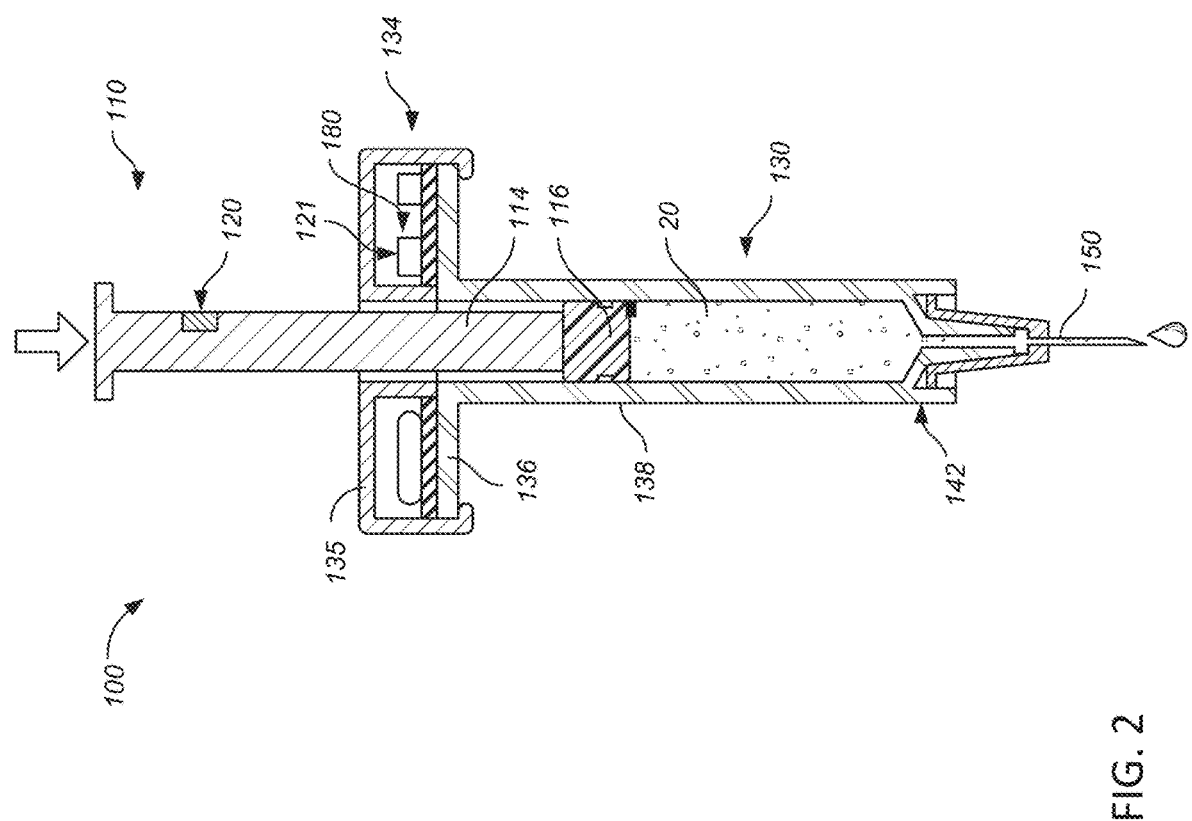
FIG. 2 illustrates schematically a cross-section of the syringe of FIG. 1A.

As shown in FIGS. 1A-2, the injection system 10 can include an injection syringe 100. The injection syringe 100 can have a plunger 110 configured to move relative to a syringe body 130. The plunger 110 can include a plunger head 112, a plunger shaft 114, and a piston 116. The syringe body 130 can include a flange portion 134, a body portion 138, and a needle coupling portion 142. The body portion 138 can have a lumen for containing an injection material, or medication 20. The syringe 100 can have a needle 150 coupled to the needle coupling portion 142 of the syringe body 130. The needle 150 can be configured to deliver the injection material or compound into an injection location on a patient and/or a training apparatus 210. Additional details of the training apparatus are described in U.S. Pat. No. 9,792,836, entitled "INJECTION TRAINING APPARATUS USING 3D POSITION SENSOR," U.S. Patent Publication No. 2015/0206456 A1, entitled "INJECTION SITE TRAINING SYSTEM," U.S. Patent Publication No. 2015/0262512 A1, entitled "AUTOMATED DETECTION OF PERFORMANCE CHARACTERISTICS IN AN INJECTION TRAINING SYSTEM," and U.S. Patent Publication No. 2017/0254636 A1, entitled "SYSTEM FOR DETERMINING A THREE-DIMENSIONAL POSITION OF A TESTING TOOL," the disclosure of each of which is incorporated herein by reference in its entirety.

The plunger 110, syringe body 130, and/or needle 150 can have one or more sensors, such as a plunger motion or travel sensor 186, a position and/or orientation sensor 191, force and/or pressure sensors 192, biometric sensor 196, medication code reader 184, and/or other types of sensors. As will be described in greater details below, the plunger motion or travel sensor 186 can measure linear movement of the syringe plunger 110 relative to the syringe body 130. The position and/or orientation sensor 191 can measure position, such as an x-y-z position, and/or orientation of the syringe. The position and/or orientation sensor 191 can be an inertial navigation system and/or a magnetic sensor. When the syringe is used for injection training, the position and/or orientation sensor 191 can additionally or alternatively include an optical sensor. The force and/or pressure sensors 192 can measure a force and/or pressure at which the medication 20 is delivered. The biometric sensor 196 can identify and/or authenticate the injector. The medication code reader 184 can scan and obtain information related to the medication in the syringe.

The plunger 110 can have one or more electrical circuitries. A biometric sensor 196, such as a fingerprint sensor, can be mounted on the plunger head 112. The biometric sensor 196 can detect and/or record the identity of a person performing the injection, and/or the identity of the user to validate that the user purchased the medication product from a manufacturer with regulatory approval, such as with FDA approval in the US, with CE marks, or the regulatory bodies in other countries. The biometric sensor 196 can be coupled to a wireless transmitter 193 for transmitting data from the biometric sensor 196 to a controller of the injection system 10. The syringe 100 can also optionally output text, audio and/or visual alerts to the patient receiving the injection, to the medication manufacturer, and/or regulatory authorities if the person performing the injection is not one qualified to perform such an injection.

Figure 3B:
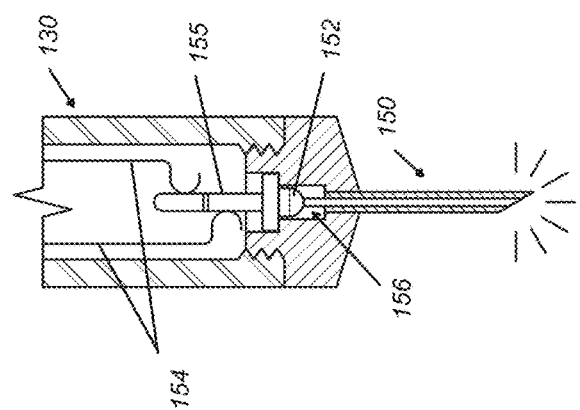
FIG. 3B illustrates schematically a cross section of a portion of the syringe at a needle end.
Figure 3A:
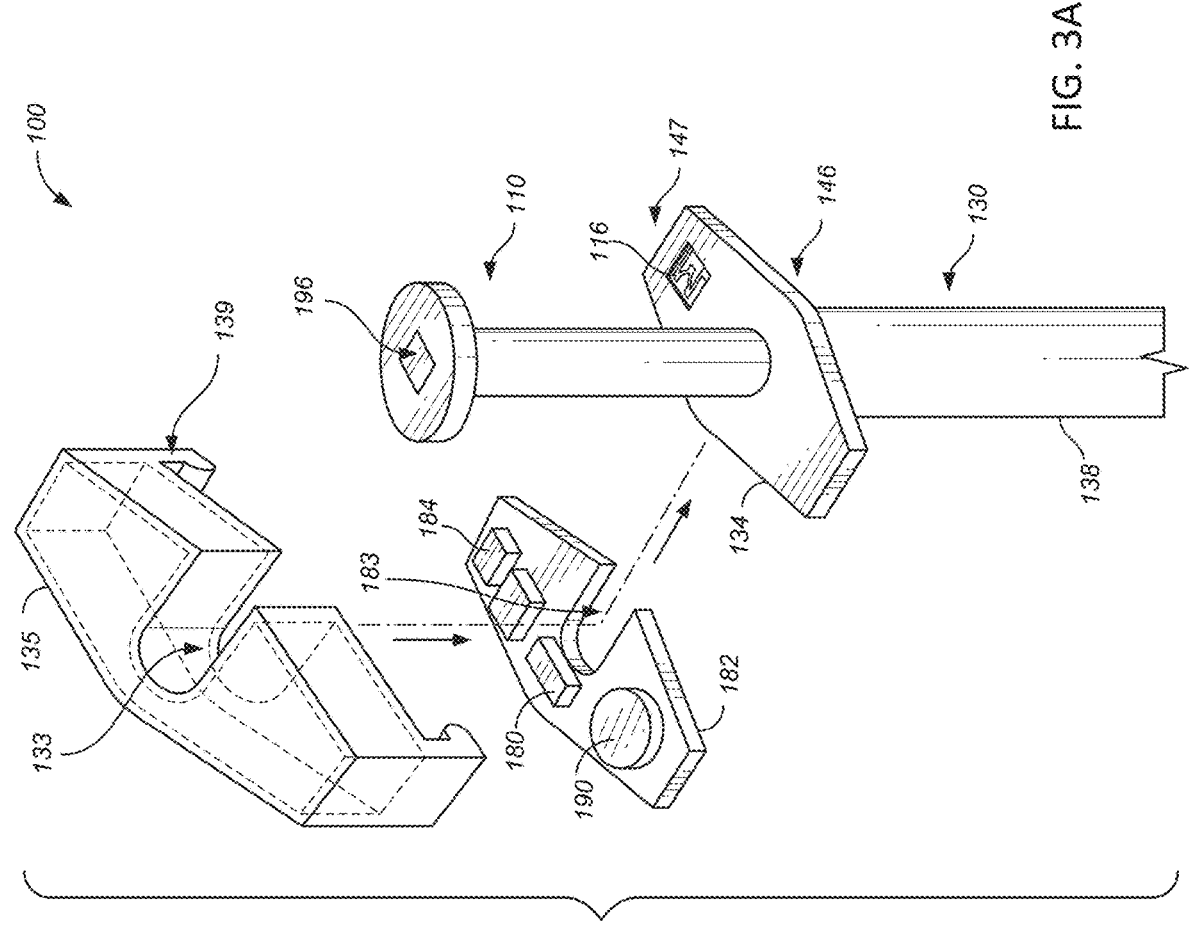
FIG. 3A illustrates schematically a partially exploded view of the syringe of FIG. 1A showing a Syringe Dose and Position Apparatus (SDPA) that can be attached to the syringe flange.

As shown in FIG. 3A, a Syringe Dose and Position Apparatus (SDPA) 180 can be mounted to the flange portion 134. The SDPA 180 can be mounted on the syringe 100 releasably or permanently. The SDPA 180 can be durable, reusable, or disposable. The flange portion 134 can have a flange base 135 and a flange cover 136. The SDPA 180 can be housed within the flange cover 136. As shown in FIGS. 2 and 3A, the flange base 135 can be integrally formed with the body portion 138 of the syringe body 130. The flange cover 136 can have a slot 139 for slidably receiving the flange base 135 to retain the SDPA 180.

The flange portion 134 can have a long side 146 and a short side 147, for example, by having generally a rectangular shape. The flange cover 135 can have a groove 133 at or near a mid-point of the long side of the flange cover 136 such that when coupled to the flange base 136, which also has a long side and a short side, the flange portion 134 can form two finger supports on diametrically opposite sides of the syringe body portion 138. The flange portion 134 can also have any other shapes and need not have two finger supports on diametrically opposite sides of the syringe body portion 138.

Figure 7:
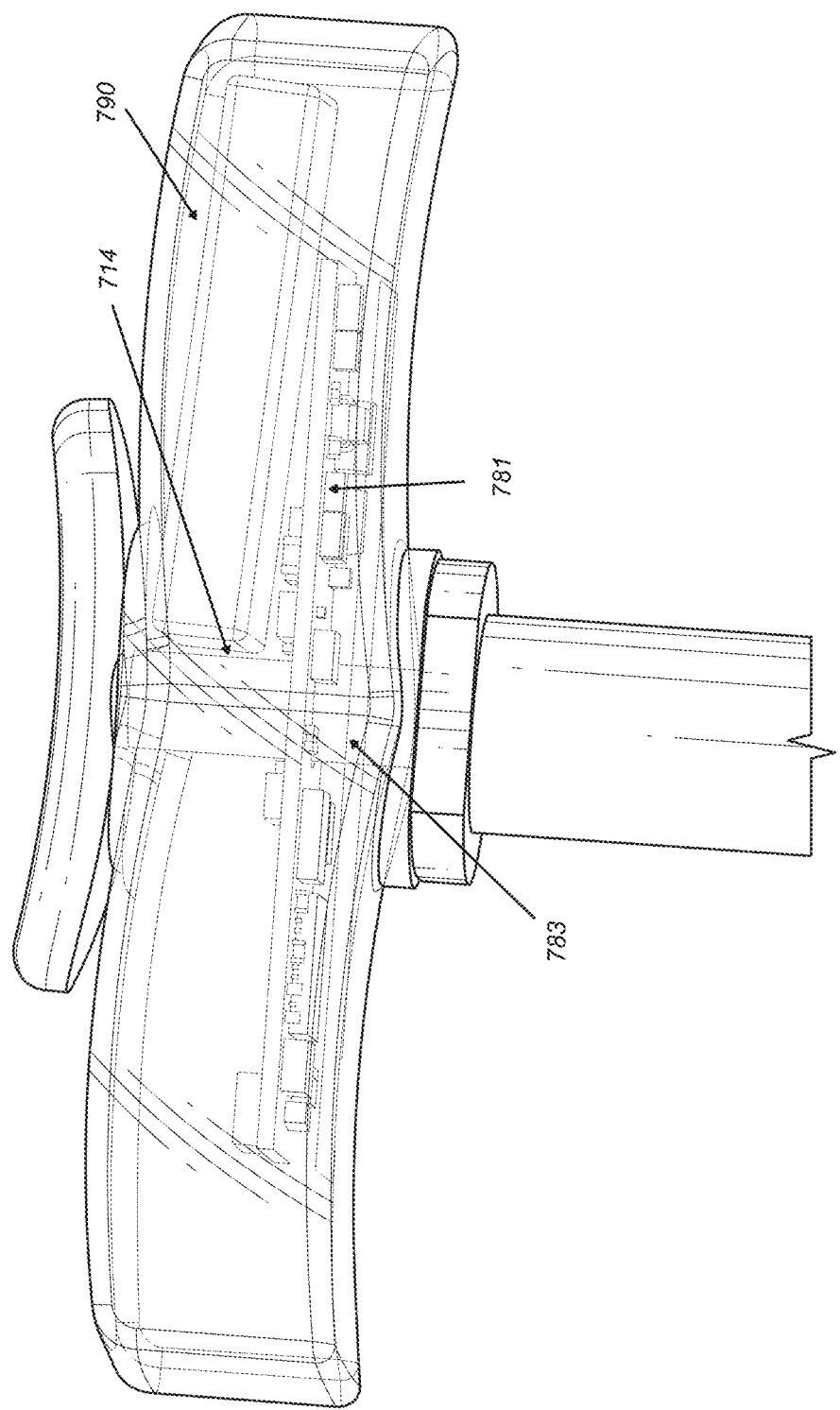
FIG. 7 illustrates a detailed view of an example syringe near the flange showing an example SDPA with a single-board configuration.

As shown in FIG. 3A, the SPDA 180 can have a printed circuit board 182. The board 182 can have a groove 183 substantially aligned with the groove 133 of the flange cover 135. Although FIG. 3A illustrates the circuit board as having circuitry components on one side of the circuit board, circuitry components can also be mounted on both side of the circuit board (such as shown in FIG. 7). The SDPA 180 can have a plurality of sensors described herein, such as an optical sensor, a contact sensor, a position and/or orientation sensor (for example, an inertial navigation system, or a three-axis accelerometer, gyroscope, and magnetometer sensor). A controller 195 of the SDPA 180 can receive inputs from the plurality of sensors. As will be described below, the sensors mounted to the SPDA 182 can be used to monitor the injection performance, including but not limited to the amount of medication delivered and/or location of delivery.

The SDPA 180 can optionally include a medication code reader 184. The flange base 114 can optionally include a medication code 116 for the medication contained in the syringe body portion 138. When the SDPA 180 is mounted to the flange portion 134, the code reader 184 can scan the code 116 for information related to the mediation that will be delivered. The controller 195 of the SDPA 180 can receive the medication information from the code reader 184. The SDPA 180 can thus also improve the knowledge of the injection procedure by monitoring and/or recording the time of delivery, the type of medication being delivered, the identity of the injector, and the like. The syringe 100 can optionally output text, audio and/or visual alerts to the patient receiving the injection, to the medication manufacturer, and/or regulatory authorities if medication information indicates that the medication is counterfeit, expired, and/or otherwise unsuitable for being delivered to the patient.

The SDPA 180 can also include the wireless transmitter 193 for transmitting the injection data to the receiver 200. The system 10 can record data about the injection procedure performed by a trainee using the injection syringe on the training apparatus or a live patient on a database 222 on a remote server 220 that is in communication with the receiver 200.

The SDPA 180 can also include a power source, such as a battery 190, for at least powering the SDPA 180 including the sensors mounted on the SDPA 180. When the injection system is used for injection training, the power source 190 can also be electrically coupled, such as via electrical wires 154 or other types of electrical conductors, with a light source 152 in the needle 150, such as shown in FIG. 3B. The electrical wires 154 can also optionally be coupled to a conductor post 155 extending from the light source 152 proximally into the lumen of the syringe body 130. The light source 152 can be an LED or any other type of light source. The light source 152 can be a low-power light emitting diode ("LED"). The low-power LED can consume less power than a LASER LED. The low-power LED can thus be powered by the power source 190 of the SDPA 180 with less complex circuitry than is required for driving a LASER LED. A smaller circuit board can be used with the low-power LED than with a LASER LED. A smaller circuit board can occupy less space on the syringe, and can promote miniaturization of the syringe.

The light source shown in FIG. 3B can be operably coupled to an optical fiber 156. The optical fiber 156 can be located near the needle 150 and extend between the light source 152 and the tip of the needle 150. The optical fiber 156 can be located within a lumen of the needle 150 and extend between the light source 152 and the tip of the needle 150. When the syringe 100 is used for injection training, the needle 150 can penetrate one or more layers of tissue-simulating materials on the training apparatus 210. The training apparatus 210 can be an anatomical model having an appearance of a patient's anatomy, such as a head, torso, limbs, and the like. The training apparatus 210 can have one or more light detectors 212, such as cameras, inside a cavity of the training apparatus 210. The light detectors 212 can be spaced apart from one another. The light detectors 212 can detect light emitting from the needle tip. A controller of the injection system 10 can be configured to determine injection data, such as a three-dimensional position, of the needle based on at least in part on data about the detected light. As will be described below, the controller can also determine the three-dimensional position of the syringe needle based on combined information from the position and/or orientation sensor and the detected light. The controller can be the controller 193 on the syringe 100 (such as the controller on the SDPA 180), or the controller 234 on the training apparatus 210, and/or on the remote server 220.

The remote server 220 and/or the controller on the SDPA 180 can also be in electrical communication with a training module 232. The training module can be loaded on a training module device 239, such as a computer, a tablet, a smartphone, or others that have a display screen. The training module 232 can receive data about the injection procedure, such as from the external receiver 200 and/or from the central server 220. The training module device 230 can have a user interface 236. The training module 232 can provide training instructions, scoring, feedback, and/or evaluation of an injection procedure, and/or certification of the injector, for example, when the injector is a trainee and has passed a test for an injection technique.

As shown in FIG. 1C, the controller and/or processor 193, 234 of the injection system 10 can receive one or more of the following inputs: position and/or orientation inputs from the inertial navigation system, position and/or orientation inputs from internal optical sensor(s), position and/or orientation inputs from external optical sensor(s) (such as external camera(s) 240 in FIG. 1B), position and/or orientation inputs from magnetic sensor(s), plunger travel sensor inputs, biometric sensor inputs, force and/or pressure sensor inputs, and/or medication code reader inputs. The injection system can provide one or more of the following outputs: syringe position and/or orientation outputs, injection force and/or pressure outputs, dose measurement outputs, injector identity and/or qualification outputs, and/or medication information outputs.

FIGS. 4A to 9C illustrate an example syringe 400. The syringe 400 can have any of features of the syringe 100. Features of the syringe 100 can be incorporated into features of the syringe 400 and features of the syringe 400 can be incorporated into features of the syringe 100.

Figure 4A:
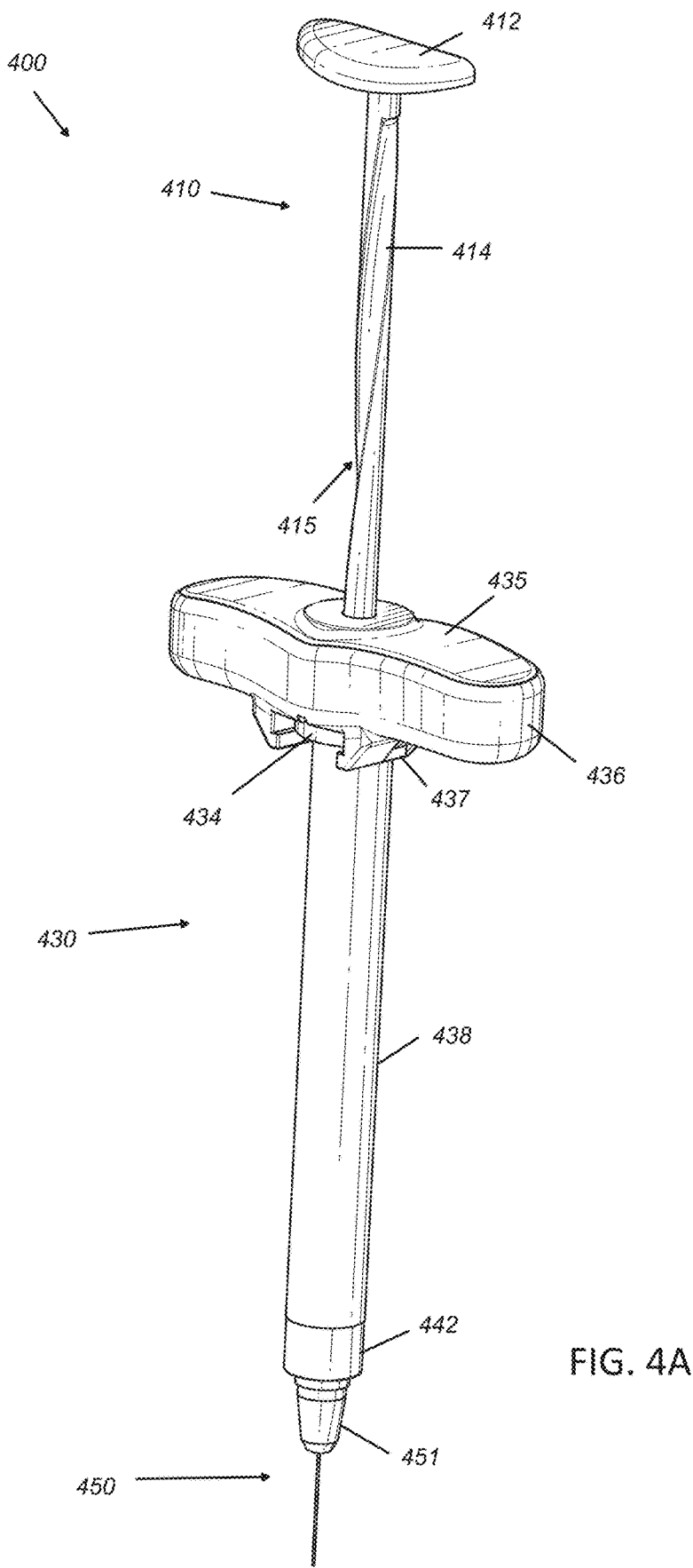
FIG. 4A illustrates an example injection syringe.

The injection syringe 400 can have a plunger 410 configured to move relative to a syringe body 430. The syringe body 430 can include a flange portion 434, a body portion 438, and a needle coupling portion 442. The flange portion 434 can protrude radially outwardly from the body portion 438 and can be of any shape. The flange portion 434 can be at a proximal end of the syringe body 430. As shown in FIG. 4A, the flange portion 434 can be integrally formed with the body portion 438. The syringe 400 can also include an SDPA 480 (shown in FIG. 4B). The SDPA 480 can be enclosed in a housing. The housing can be mounted to the flange portion 434 or anywhere on the syringe 400. The housing and the SDPA 480 can be releasably or permanently mounted to the syringe. The housing can have a cover 435 and a base 436. The cover 435 and/or the base 436 can have an internal compartment configured to receive the SDPA 500. The cover 435 and/or the base 436 can optionally have internal guide rails, posts, or the like, for securely supporting the SDPA 480 inside the housing. The housing cover 435 and base 436 can each include an opening 433 configured to slidably accommodate a plunger shaft 414.

Figure 5A:
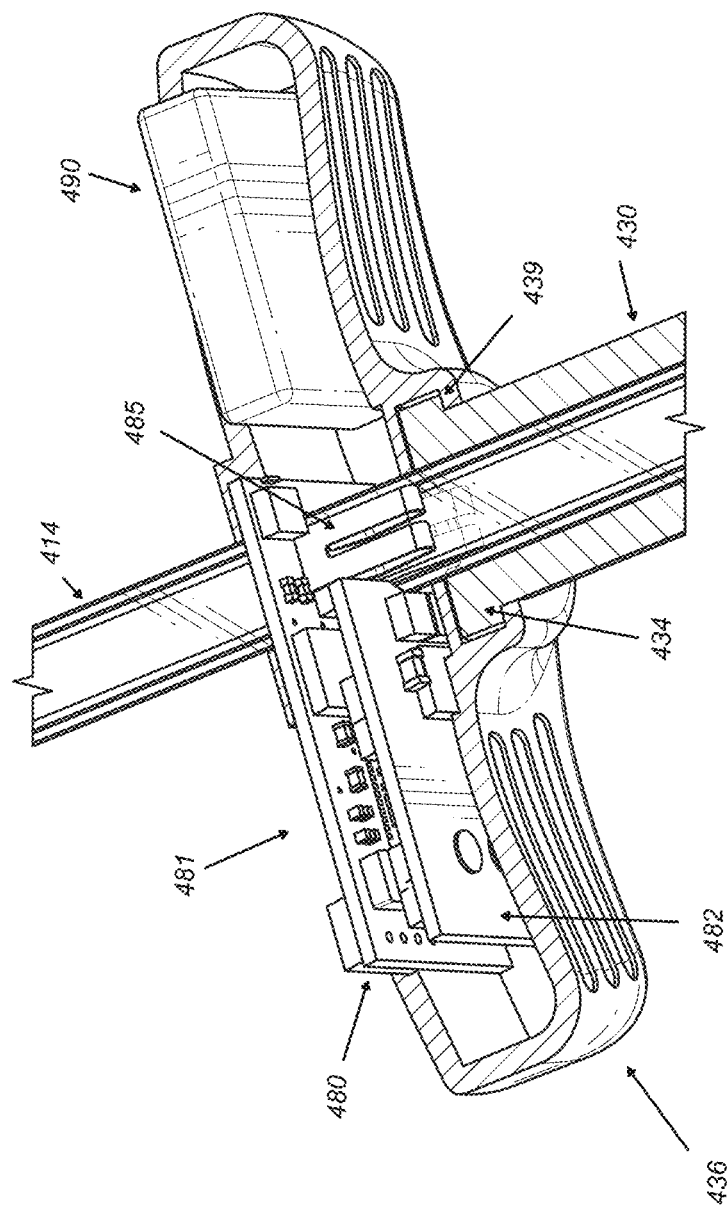
FIG. 5A illustrates a detailed view of the syringe of FIG. 4A near the flange with portions of the syringe body, the flange and the plunger removed for illustration purposes.

The SDPA housing can be coupled to the flange portion 434 of the syringe body 430. As shown in FIGS. 5A and 6, the housing can be coupled to the flange portion 434 using a clip-on feature. The clip-on feature can have a slot 439 on the SDPA housing. The slot 439 can be sized to accommodate the syringe flange portion 434. The flange portion 434 can be slidably received by the slot 439 and can optionally also secured to the housing with adhesives or other ways of securement. The flange 434 can also be secured to the housing by friction between the slot 439 and the housing. As shown in FIGS. 5A and 6, the slot 439 can be on a distal surface of the housing base 435. The slot can also be on any other location of the SDPA housing. Additionally or alternatively, the flange 434 can also be secured to the SDPA housing using securement features other than the clip-on feature, such as magnet(s), adhesives, and/or detent(s).

Figure 5B:
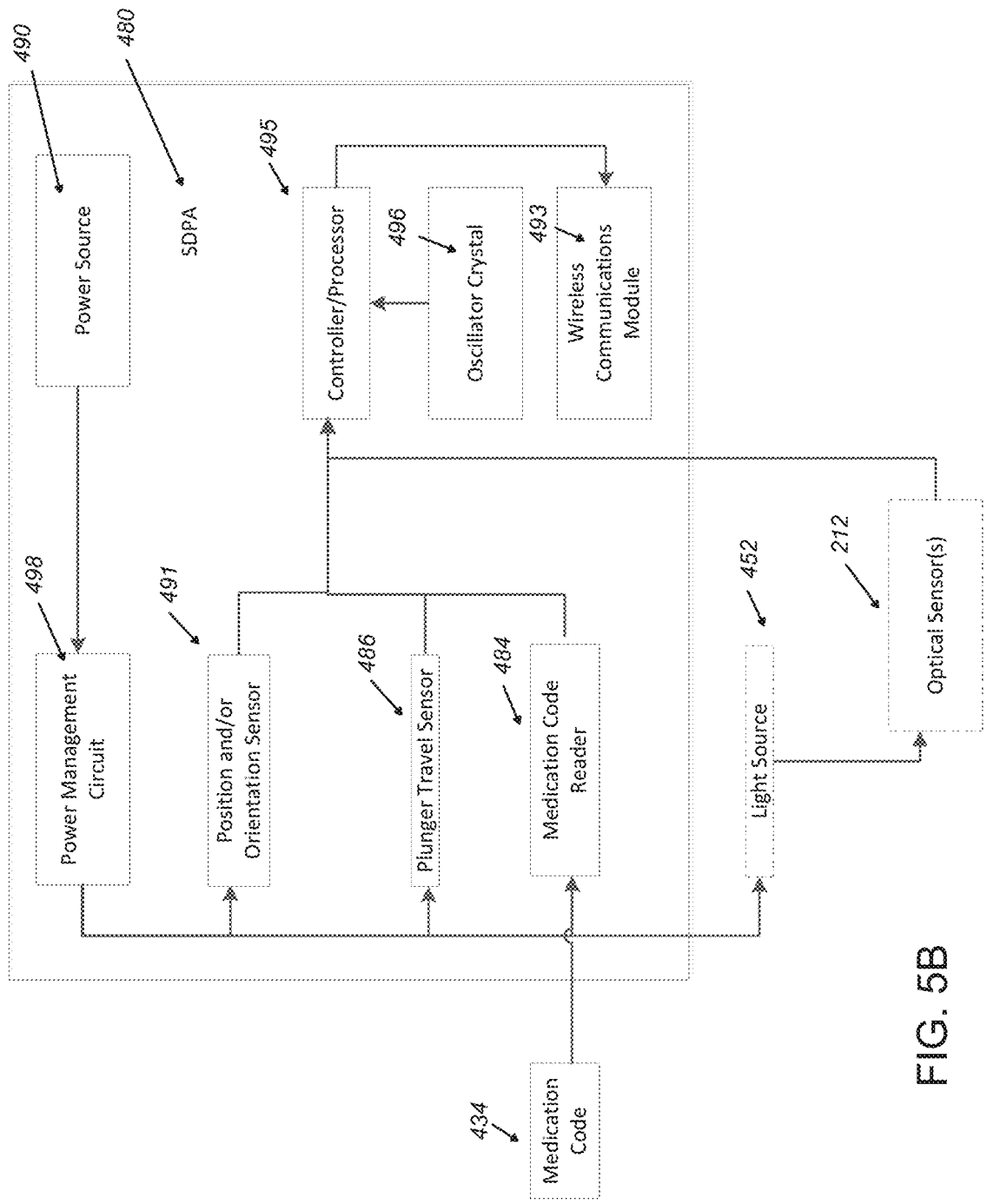
FIG. 5B illustrates schematically a block diagram of the SDPA of FIG. 4A interacting with other components of the syringe.

As shown in FIG. 5B, the SDPA 480 can have a plurality of sensors, which can be any of the sensors described herein. The SDPA 480 can have a position and/or orientation sensor 491, a plunger travel sensor 486, and/or a medication code reader 484 configured to obtain information from a medication code 416, which can be located on the flange portion 434. The SDPA 480 can also include wireless communication module 493, including a radiofrequency antenna and Bluetooth low energy, or other protocols. The SDPA 480 can also optionally include an oscillator crystal 496. The oscillator crystal 496 can function as a timer. The SDPA 480 can include a power management circuit 498. The power management circuit can be in electrical contact with a power source 490. The power source 490 can be a battery, such as a rechargeable battery. The power source 490 can also include more than one battery. The battery can have a life of about 20 mAh, about 30 mAh, about 40 mAh or more. The power source 490 can provide power to the SDPA 480 and/or its components via the power management circuit 498. The power source 490 can also optionally power a light source 452 near the needle of the syringe. The SDPA 480 can include a controller 495, such as a central processing unit. The controller 495 can receive sensor inputs from the sensors on the SDPA 480. The controller 495 can also optionally receive inputs from optical sensor(s) 212 in the training apparatus, when the syringe is used for injection training. The controller 495 can determine information related to the injection procedure based at least in part on the sensor inputs.

As shown in FIGS. 4B, 4E, 4F, and 5A, the SDPA 480 can have two PCBs 481, 482. The circuitry components and the layout thereof on first and second PCBs 481, 482 are for illustrative purposes only and can be varied. For example, the circuitry components can be on one side or both sides of the circuit board. The two PCBs 481, 482 can be at least partially stacked. The first PCB 481 can include any of the sensors described herein, for example, a position and/or orientation sensor 491, a plunger travel sensor 486, and/or a medication code reader 484 configured to obtain information from a medication code 416, which can be located on the flange portion 434. The first PCB 481 can include a controller 495, such as a central processing unit. The first PCB 481 can also include wireless communication module 493, including a radiofrequency antenna and Bluetooth low energy, or other protocols. The first PCB 481 can also optionally include an oscillator crystal 496. The oscillator crystal 496 can function as a timer. The second PCB 482 can include a power management board. The power management board can be in electrical contact with a power source 490. The power source 490 can be a battery, such as a rechargeable battery. The power source 490 can also include more than one battery. The battery can have a life of about 20 mAh, about 30 mAh, about 40 mAh or more. The first and second PCBs 481, 482 can be electrically coupled by one, two, or more flex circuits 485, or any other type of electrical conductors, such as board-to-board connectors. Although the figures illustrate the first PCB 481 stacked on top of the second PCB 482, the second PCB 482 can be stacked on top of the first PCB 481.

As the SDPA housing can form two finger supports on diametrically opposite sides of the syringe body portion 438, the stacked PCBs 481, 482 can be substantially housed within one of the finger supports, with a hole 483 on the first PCB 481 to slidably accommodate the plunger shaft 414. The power source 490 can be located in the other one of the finger supports. The PCBs 481, 482, and the power source 490 can be small enough to fit into one of the finger supports of the SDPA housing. The PCBs can have a size of about 22.9 mm×12.7 mm, or smaller. The battery can have a size of about 3 mm×11 mm×20 mm, or about 3 mm×12 mm×15 mm, or smaller. The form factors of the PCBs and any of the components on the PCBs, such as the battery and the sensors, are not limiting. The stacked PCBs can reduce a size of the SDPA 480 and/or a size of the SDPA housing.

As shown in FIGS. 5A and 6, the housing base 436 can include a distally facing concave or curved surface at each of the finger supports. The curved surface can improve comfort and/or grip of the injector's fingers when manipulating the syringe 400.

The SDPA can also have a single PCB 182, such as the SDPA 180 of the syringe 100, and as shown in FIG. 7. The sensors and/or controller circuitry can be housed in one of the finger supports and the power management board can be located in the other one of the finger supports. In FIG. 1, the power source 190 can be located on the PCB 182. In FIG. 7, the power source 790 can be stacked on top of a portion of the PCB 781, such as on top of the power management board. The PCB 781 in FIG. 7 can also include a hole 783 at or near a center of the PCB 781. The hole can be configured for slidably accommodating the plunger shaft 714. The PCB 781 in FIG. 7 can have a size of about 43.2 mm×8.9 mm, or about, 38.1 mm×11.5 mm. The hole 783 in the PCB 781 can have a diameter of about 5 mm.

Turning to FIGS. 8A-8D, the body portion 438 and the needle coupling portion 442 can be manufactured as separate components. During assembly, the body portion 438 of the syringe body 430 can be releasably or permanently coupled to the needle coupling portion 442. A distal end of the body portion 438 and a proximal end of the needle coupling portion 442 can have corresponding coupling features, such as a hexagonal socket 439 on the distal end of the body portion 438 and a hexagonal head 443 on the proximal end of the needle coupling portion 442, or any other types of coupling features.

The body portion 438 and the flange portion 434 can have a continuous or interconnected wire lumen 440. The wire lumen 440 can be formed in a wall of the flange portion 434 and the body portion 438. The wire lumen 440 can allow one or more electrical connectors, such as one or more lead wires, be extended between the power source 490 in the SDPA and the light source, such as the light source 152 in FIG. 3B. The body portion 438 and the flange portion 434 can also include more than one, such as two wire lumens for accommodating the electrical connectors. The wire lumen 440 can terminate near the distal end of the body portion

438. The body portion 438 can also include one or more radially inward protrusions 441 at or near where the wire lumen 440 ends. The protrusions 441 can support and/or secure the light source inside the body portion 438. One or more LED circuit boards can also be install at or near the distal end of the syringe body portion 438 to hold the LED that is installed in the bottom of the syringe tube. The one or more electrical connectors can connect the one or more LED circuit boards to the SDPA 480.

The needle coupling portion 442 can have a throughlumen 444. The throughlumen 444 can provide a passage for the medication and/or an optic fiber, such as the optic fiber 156 in FIG. 3B. The needle coupling portion 442 can include Luer lock connections or threads, such as M3 threads, for releasably coupling the syringe body 430 to the needle 450.

As described above, an optical fiber can be located within a lumen of the needle and extending between the light source and the tip of the needle. The optical fiber can be fused to the lumen of the needle. The optical fiber 456 can extend from a proximal end of the needle toward the light source, such as shown in FIG. 9C. The optical fiber 456 can also be bonded to a receptacle 451 that is connected to the needle 450. The receptacle 451 can releasably couple the needle 450 to the needle coupling portion 442. The receptacle 451 can include Luer lock connections or threads 453, such as M3 threads. Engagement of M3 threads on the receptacle 451 and corresponding threads 445 on the needle coupling portion 442 can improve centering of the optic fiber 456 over the light source, compared to the Luer lock connections.

The optic fiber can be a mono fiber optic cannula (for example, as manufactured by Doric Lenses). The fiber can have a core diameter of about 100 μm. The numerical aperture of the fiber can be large for improved input and output angle of the light, and/or for reducing sensitivity to lateral offsets of the fiber. The fiber can have a numerical aperture of about 0.37, or about 0.66, or larger. The fiber can have an outer diameter of about 0.4 mm. The needle can be a gauge 30 hypotube needle, which has an internal diameter of about 0.14 mm to about 0.178 mm. The needle can also have a larger internal diameter, such as about 0.5 mm, which can accommodate the fiber having an outer diameter of about 0.4 mm. The needle can have a length of about 12.7 mm.

The optical fiber can optionally have a shaved optical fiber end near a tip of the needle. The shaved optical fiber end can improve a bloom of the optical fiber end and/or provide a substantially omni-directional light. The optical fiber can also have a diffuser layer at its distal end. The diffuser layer can spread out the output light when the light exits the fiber and improve the bloom of the light. The substantially omni-directional light can have approximately equal level of intensity in substantially all the directions. The improved bloom can improve detection of the light source with a large side profile of the needle inside the training apparatus.

The syringe need not have any of the optical sensor components, such as the light source, the lead wire(s), the optic fiber, and the like. The syringe without the optical sensor can be used for delivery actual medication to patients.

Dose Measurement Examples

Figure 5C:
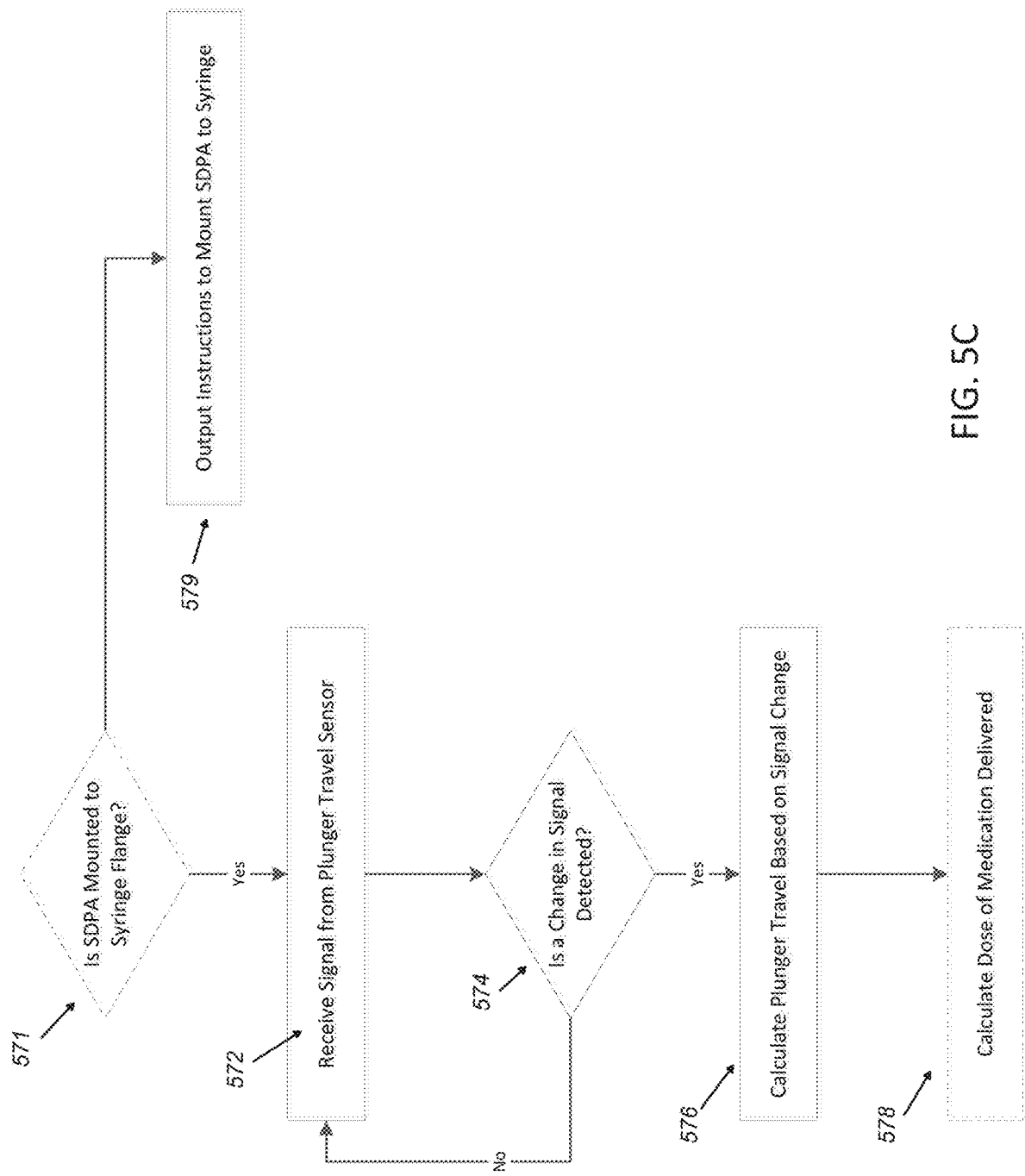
FIG. 5C illustrates schematically a flow chart of an example method of plunger travel measurement.

As described above, the SDPA can improve the knowledge of medication delivered in an actual injection procedure or a training procedure, including the amount or dose that is delivered during the injection. One way to measure dose by the controller of the SDPA or the training module is based on plunger travel measurements. An example method of plunger travel measurement is illustrated in FIG. 5C. At step 571, the controller can optionally determine whether the SDPA has been mounted to the syringe flange. For example, the controller can determine that the SDPA has been mounted to the syringe upon detection of a medication code on the flange by the medication code reader described herein. If the SDPA has not been mounted to the syringe flange, at step 579, the controller can output an instruction to a user, such as an injector or a nurse, to mount the SDPA to the syringe. If the SDPA has been mounted to the syringe flange, at step 572, the controller can receive a signal from a plunger travel sensor, which can be any of the plunger travel sensor described below. At decision step 574, the controller can determine whether a change in the signal, such a change in resistance or a change in the magnetic field, can be detected. If no change has been detected, the controller can return to the step 572. If a change in the signal has been detected, at step 576, the controller can calculate the linear movement of the plunger, or the plunger travel based at least in part on the change in the signal. At step 578, the controller can optionally calculate the volume of the medication delivered by multiplying the distance traveled by the plunger and the internal cross-sectional area of the syringe body portion.

The SDPA can measure plunger travel that does not rely on viewing graduation. The plunger travel measurements can be made using various sensors, for example, a rotary potentiometer, a linear resistance potentiometer, a magnetometer, or the like. The sensor for plunger travel measurements can be at least partially located on the SDPA. The plunger travel measurements described herein are advantageous over relying on viewing graduations on the syringe body, which can be subjective and/or less accurate. The sensor-based plunger travel measurement data can also be collected and recorded to a server without having to be manually entered, and can be combined with other types of injection data, such as the time of delivery, type of medication, location of delivery, among other types of information.

The injection system can also optionally simulate viscosity of the medication by adding resistance to the plunger. The injection system can adjust the magnitude of the resistance based on the medication information read by the code reader on the SDPA. The resistance applied to the plunger can also be large enough to cause a complete stop of plunger travel, such as plunger travel toward the distal end and/or proximal end of the syringe body. The complete stop resistance can be activated when the injection system determines that an intended amount or dose of the medication has been delivered. The stop feature can prevent overdose and/or promote injection safety.

Rotary Potentiometer

As shown in FIGS. 4A-4D, the plunger shaft 414 can be generally cylindrical. The shaft 414 can have a helical or substantially helical groove 415 along a longitudinal axis of the plunger shaft 414. As shown in FIG. 4D, the helical groove 415 can result in a transverse cross-section of the plunger shaft 414 being generally D-shaped. The helical groove 415 can rotate about 270 degree. The helical groove 415 can have a length of about 50 mm to about 100 mm, or about 76 mm per 360 degree. The plunger shaft 414 can also have a helical profile with a different linear distance per revolution.

Figure 4B:
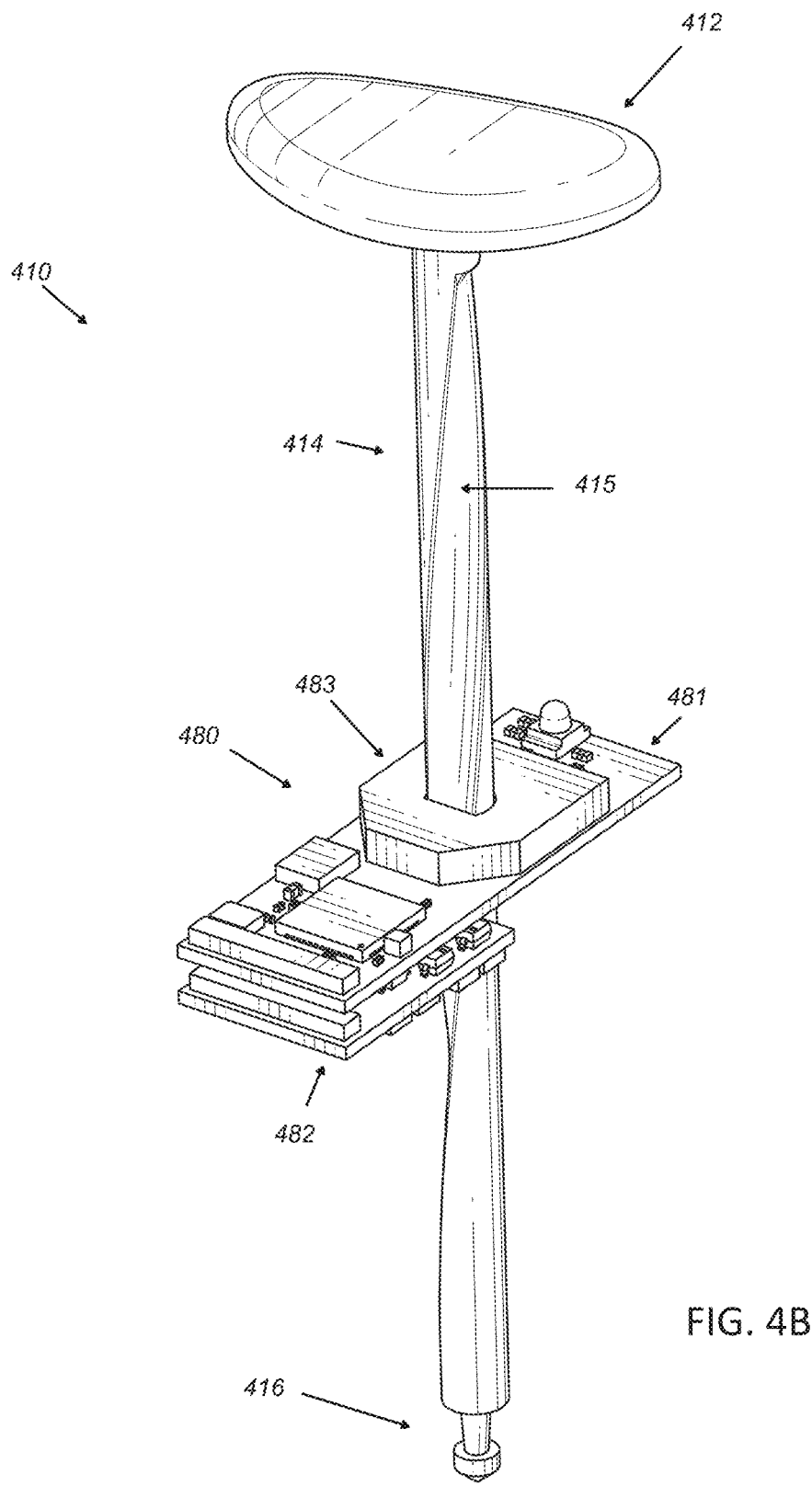
FIG. 4B illustrates the syringe of FIG. 4A with a housing removed to show the SDPA.
Figure 4F:
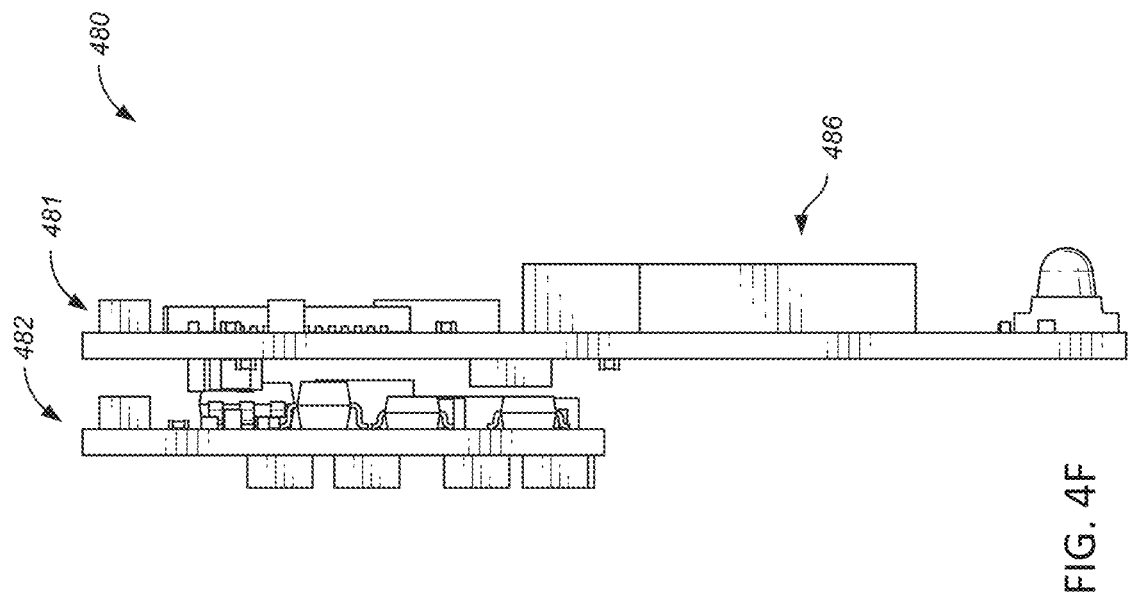
FIG. 4F illustrates a side view of the SDPA of FIG. 4E.

The SDPA 480 can include a keyed rotary sensor or potentiometer 486 (see FIG. 4B). The rotary sensor 486 can be a hollow-shaft type sensor. The rotary sensor 486 can have a stationary housing 487 and a bearing 488. The bearing 488 can have a generally D-shaped opening 489.

The opening 489 can be configured to slidably accommodate the generally D-shaped plunger shaft 414. The bearing 488 can rotate along the helical groove 415 during linear advancement of the plunger shaft 414 while permitting the housing 487 to remain stationary. When the plunger 410 is advanced distally toward the needle tip in a linear movement, for example, to deliver medication or simulate delivery of medication, the rotary sensor 486 can monitor the angular position of the bearing 488 relative to the housing 487. The rotary sensor 486 can calculate a distance of the linear movement based on the amount of rotation of the helical groove 415 measured by the rotary sensor 486. The amount of rotation of the helical groove 415, that is, the angular position of the bearing 488, can be determined based on a change of resistance of the rotary sensor 486 due to the rotation of the bearing 488.

Figure 4E:
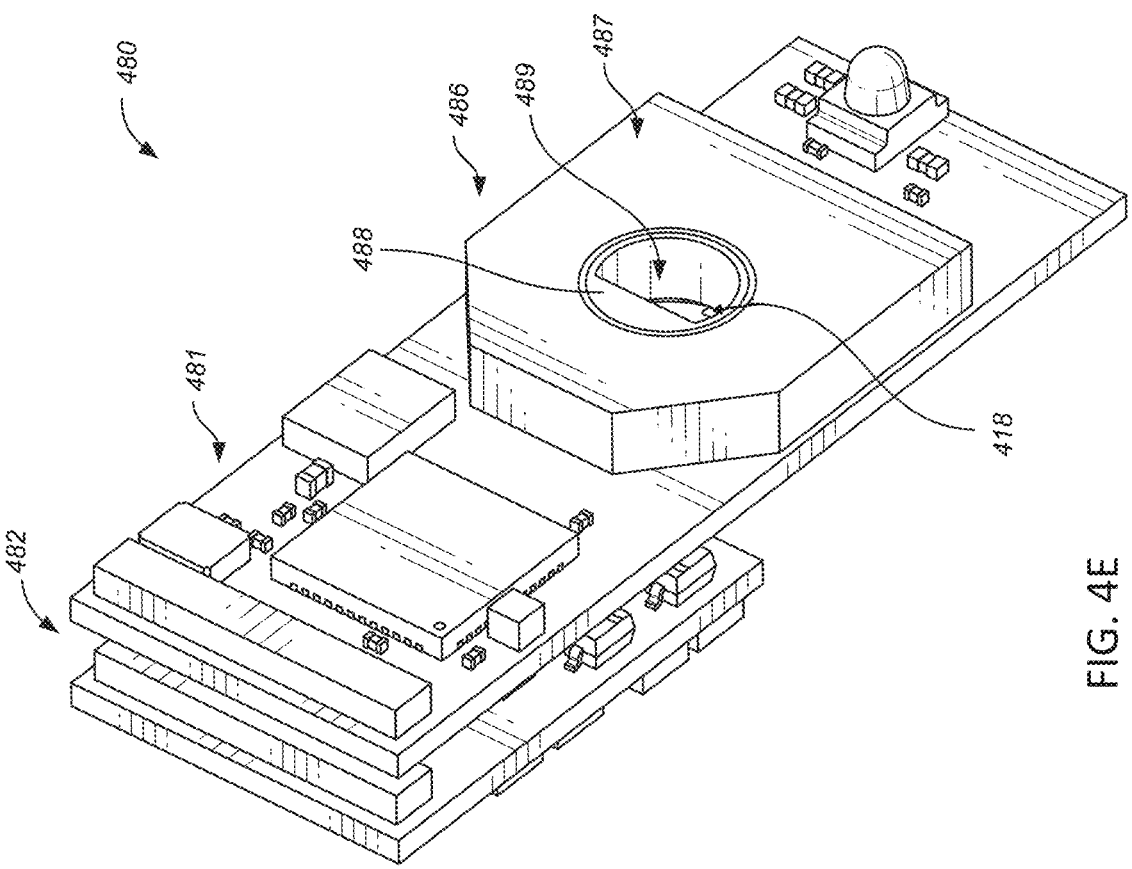
FIG. 4E illustrates a front perspective view of an example SDPA having a dual-board configuration.
Figure 4H:
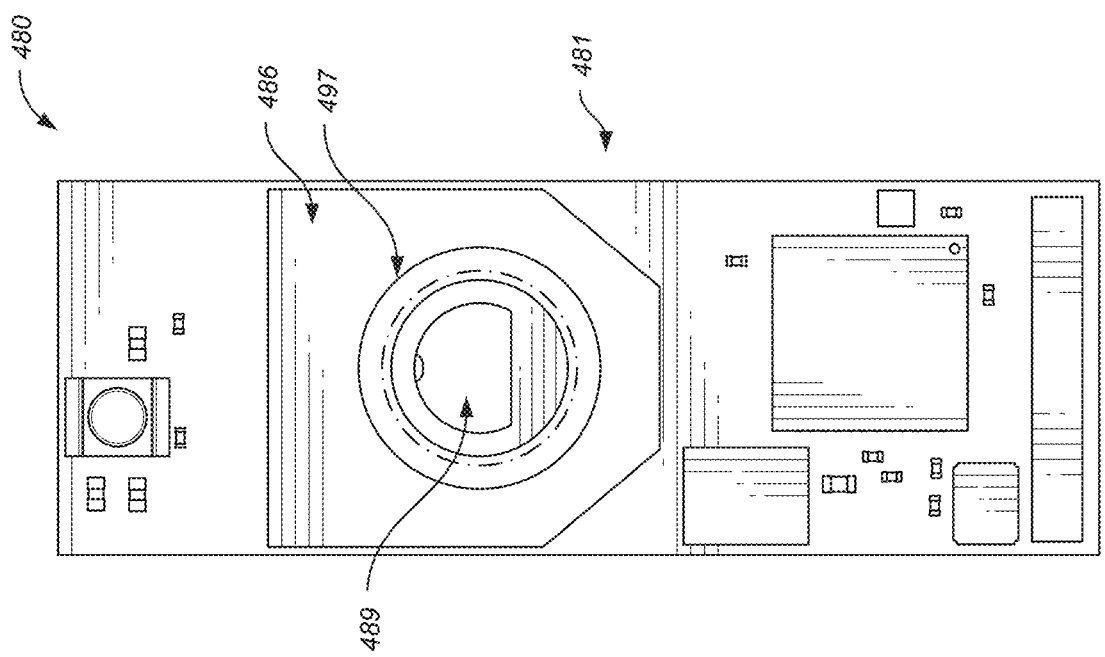
FIG. 4H illustrates a front view of the SDPA of FIG. 4A modified to include a gear.
Figure 4G:
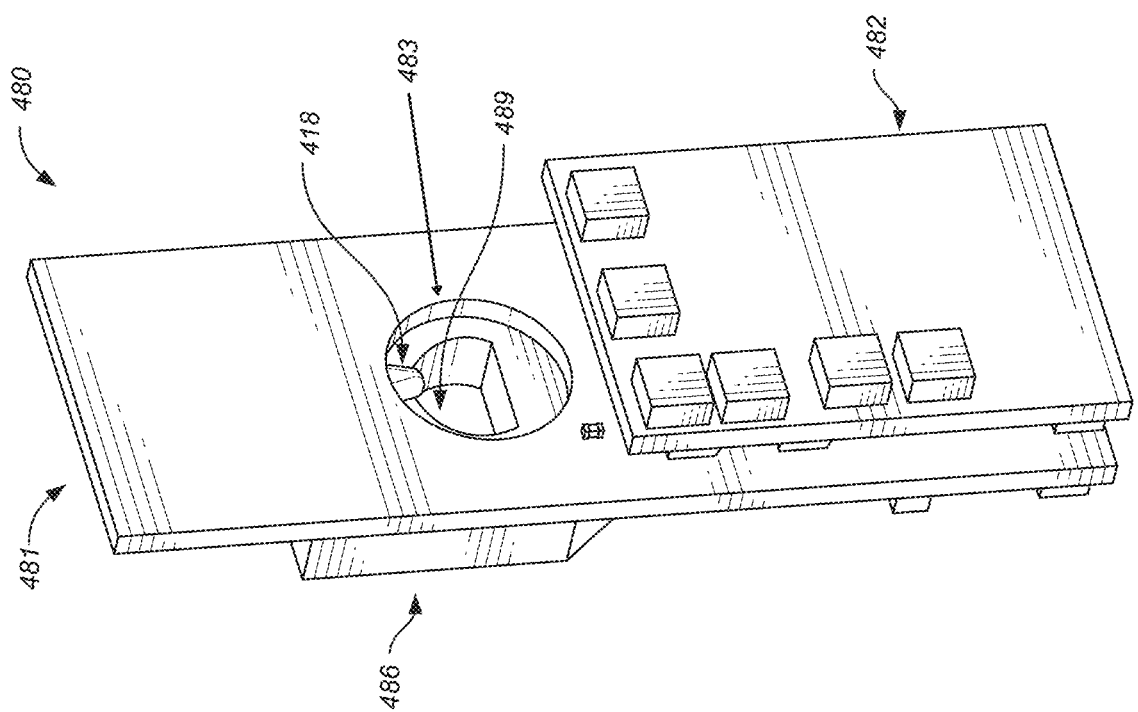
FIG. 4G illustrates a back perspective view of the SDPA of FIG. 4E.

The plunger shaft 414 can further include a substantially straight channel 417 along the longitudinal axis of the plunger shaft 414 (see FIG. 4C). The stationary housing 487 of rotary sensor 486 and/or the circuit board can have a corresponding protrusion, such as a tab that engages the channel 417. FIG. 4E illustrates the protrusion 418 on the first PCB 481 underneath the sensor housing 487. The protrusion 418 extends radially inwardly into the opening 489 of the bearing 488. The engagement between the protrusion 481 and the channel 417 can prevent the rotary sensor 486 from converting a pure rotation of the plunger 410 into a measurement of linear movement of the plunger 410. This is because when a force is applied to try to rotate the plunger 410 without axially moving the plunger 410, the engagement between the protrusion 481 and the channel 417 can prevent rotation of the plunger 410 and/or the bearing 488. However, when the plunger 410 is moved axially, the engagement between the protrusion 481 and the channel 417 forces the bearing 488 to rotate along the helical profile formed by the helical groove 415. The engagement forces the rotary sensor 486 to rotate only by linear translation of the plunger 410.

The rotary sensor 486 can also optionally include a gear 497 (see FIG. 4H) on a proximal surface of the sensor 486. The gear 497 can also be keyed to the plunger 410 with the helical profile and can rotate as the plunger 410 moves axially. The gear 497 can optionally add resistance to the plunger travel. The gear 497 can be configured to vary the resistance added to the plunger travel based on the medication information read by the code reader on the SDPA. The gear 497 can be configured to vary the resistance to the plunger travel by varying the amount of friction required to turn the gear.

Linear Resistance Potentiometer

A resistance change directly corresponding to the linear movement of the plunger can also be measured. The syringe plunger can include a resistance strip extending generally parallel to the longitudinal axis of the plunger shaft. The resistance strip can have a conductive paint (for example, carbon- or graphite-based paint, copper-based paint, silver-based paint, or any other conductive compound(s)). The conductive paint can provide electrical resistance when a strip of the conductive paint is connected to an electrical circuit.

FIG. 10 schematically illustrates an example syringe 1000 with a linear resistance-based plunger position detecting feature. The syringe 1000 can have any of features of the syringe 100, 400. Features of the syringe 100, 400 can be incorporated into features of the syringe 1000 and features of the syringe 1000 can be incorporated into features of the syringe 100, 400.

As shown in FIG. 10, the linear resistance-based plunger position detecting feature can include a resistance strip 1015 and a pair of electrical contacts 1037. The plunger 1010 can have a thumb portion 1012 on a proximal end of the plunger 1010 and a shaft portion 1014 extending from the thumb portion 1012 to a distal end of the plunger 1010. The shaft portion 1014 can be generally cylindrical. The conductive or resistance strip 1015 can start on a first radial side of the shaft portion 1014 at or near the thumb portion 1012. The resistance strip 1015 can extend generally along the longitudinal axis of the plunger shaft portion 1014 to the distal end of the plunger 1010, continue across (for example, diametrically across) a distal surface of the shaft portion 1014, and extend back toward the thumb portion 1012 along the longitudinal axis on a second radial side, generally opposite the first radial side, of the shaft portion 1014.

As shown in FIG. 10, the syringe body 1030 can have a flange 1034 at or near a proximal end of the syringe body 1030. The flange 1034 can support or enclose two springy or spring-loaded contacts 1037 (such as conductive wires or conductive strips). The contacts 1037 can be located generally diametrically opposite each other and can extend radially slight over the wall of the syringe body and into the syringe lumen. The contacts can be electrically coupled to the SDPA 1080. The flange 134 can further include a power source 1090 located diametrically opposite the SDPA 1080.

When the shaft portion 1014 of the plunger 1010 is inserted distally into the syringe body 1030 end and translates relative to the syringe body 1030, each of the contacts 1037 can make contact, such as firm contact, with the resistance strip 1015 on the first or second radial side. Contacts established between the resistance strip 1015 and the contacts 1037 can complete an electrical circuit. A portion of the resistance strip 1015 connecting the two contacts 1037 can provide resistance in the circuit. As indicated by the arrow in FIG. 10, a length of the resistance strip 1015 that connects the two contacts 1037 in forming an electrical circuit can vary as the plunger 1010 moves axially relative to the syringe 1030. When the plunger 1010 moves proximally relative to the syringe body 1030 and away from the needle 1050, the portion of resistance strip 1015 connecting the contacts 1037 can decrease in length. The resistance measured by the circuit can decrease. When the plunger 1010 moves distally relative to the syringe body 1030 and toward the needle 1050, the portion of resistance strip 1015 connecting the contacts 1037 can increase in length. The resistance measured by the circuit can increase.

The one or more processors or controllers on the syringe 1000, such as on the SDPA described above, can be configured to monitor the resistance readings between the contacts 1037. The one or more processors can be configured to determine the position of the plunger 1010 relative to the syringe body 1030 based at least in part on the resistance readings. The processors can compare the resistance readings to a look-up table, compute the plunger travel using an equation, or others.

The electronics for detecting resistance changes and that are on or embedded in the flange, such as on the SDPA, can be smaller than commercially available off-the-shelf electronics, such as off-the-shelf linear encoders.

Magnetic Sensor on Plunger

The SDPA can also measure the plunger travel using a magnetic sensor 120 (see FIG. 2). The plunger can include a magnetic chip. The magnetic chip can have a permanent magnet. The magnetic chip can be located at any location on the plunger. The SDPA can include a magnetic field sensor 121. The magnetic field sensor can detect changes in the magnetic field of the magnetic chip as the plunger is moved linearly relative to the syringe body. The changes in the magnetic field can be used to measure the plunger travel.

The one or more processors or controllers on the syringe 1000, such as on the SDPA described above, can be configured to monitor the magnetic field readings. The one or more processors can be configured to determine the position of the plunger 1010 relative to the syringe body 1030 based at least in part on the magnetic field readings. The processors can compare the magnetic field readings to a look-up table, compute the plunger travel using an equation, or others.

Position and/or Orientation Detection

The one or more position and/or orientation sensors, such as a magnetometer, a gyroscope, an altimeter, and/or an accelerometer, can provide data related to the position of the syringe to the controller of the injection system, such as the controller on the SDPA. The injection system can determine a three-dimensional position of the syringe and/or an attitude of the syringe based at least in part on the data from the one or more position and/or orientation sensors. The attitude can provide orientation information of the syringe in a three-dimensional space in addition to the x-y-z position of the syringe. The orientation, or attitude, information can include, for example, an angle at which the syringe, more specifically, the syringe needle, is titled. When the injection system includes the optical sensor described herein, the camera(s) inside the training apparatus can also provide data related to the position of the needle tip. The controller of the injection system can fuse the data from the position sensors and the camera(s) to improve accuracy in determining the x-y-z position of the syringe.

Together, all the position data can be combined to provide determinations of the position and attitude of the syringe when the needle punctures the apparatus material. Due to the give from the training apparatus when the needle punctures the apparatus, estimates of the attitude of the syringe can provide improved accuracy in determining an angle of insertion of the needle. The training apparatus material can adhere to the needle when the needle is pulled out of the training apparatus. The tugging can block the light source in the needle tip for one or more of the light detectors inside the training apparatus. Data from the accelerometer of the position sensor (for example, short-term data from the accelerometer) can be combined with data from other light detectors that can detect the light source. The combined data can provide an estimate of readings on the light detector with the blocked light source. By combining all the information together to correct estimates, the processor can be configured to predict errors before they happen in live patients.

Processing raw data from the position sensor and/or camera(s) can include estimating the position and/or attitude of the syringe at a high frequency (such as in the magnitude of thousands of Hertz or tens of thousands of Hertz). Correcting the estimated position and attitude of the syringe at a high frequency can reduce drift and improve accuracy of the estimates. Processing raw data on the controller of the injection system, such as the controller on the SDPA, can allow the controller to update the estimated positon and/or attitude readings, combine all the raw data from different sensors, and/or correct error at a higher frequency. This can also improve overall accuracy of the determination of the position and/or attitude of the syringe.

Magnetic Syringe Tracking Sensor

In addition to or alternative to the optical sensor described herein, a magnetic sensor can be used for tracking the syringe and/or provide information related to a position (for example, three-dimensional position) of the syringe.

Figure 11A:
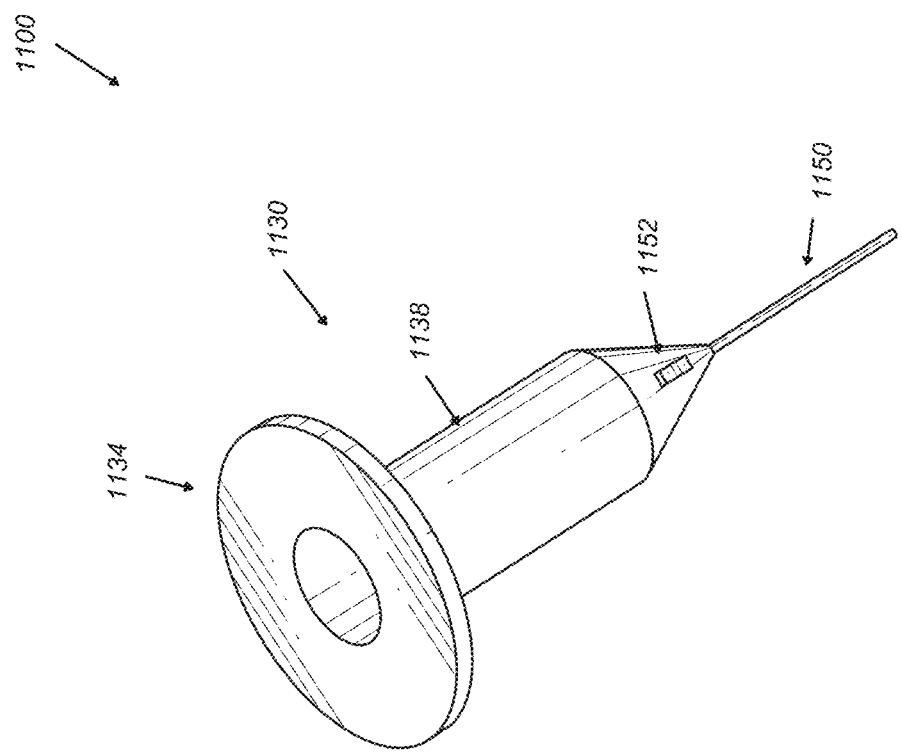
FIG. 11A illustrates schematically an example syringe with a magnetic syringe tracking sensor.

FIG. 11A illustrates schematically a syringe 1100 having a magnetic sensor. The syringe 1100 can have any of features of the syringe 100, 400, 1000. Features of the syringe 100, 400, 1000 can be incorporated into features of the syringe 1100 and features of the syringe 1100 can be incorporated into features of the syringe 100, 400, 1000.

The magnetic sensor can include a magnet and a magnetic field sensor, or magnetometer. A magnetic chip 1152 can be located on the syringe body 1130 near the needle 1150, for example, on or near a distal end of the syringe body 1130. A position of the magnetic chip 1152 can be determined by an external magnetic field sensor and provided to the controller of the injection system. The external magnetic field sensor can have a predetermined physical locational relationship with a physical area of interest, for example, the training apparatus or a live patient. Information of the position of the magnetic chip 1152 can be configured to provide tracking of movements of the syringe 1100 (for example, in a three-dimensional space) relative to the magnetic field sensor.

A second magnet chip can also be positioned at a different location on the syringe. For example, the second magnetic sensor can be positioned on the syringe body near the flange 1134 or closer to the flange 1134 than the magnetic chip 1152 shown in FIG. 11. The controller can use positional data of the two magnetic chips to determine an attitude of the syringe.

The magnetic chip can be more compact than the optical sensor. A needle of a smaller cross-sectional diameter (higher gauge number, such as a gauge 30 needle) can be used with the magnetic chip than a needle configured for accommodating the optical sensor inside the needle. To detect the light source from the needle, one or more light detectors are required inside the training apparatus. It can be difficult to fit the plurality of light detectors inside the training apparatus. The magnetic chip(s) can be used without additional detectors internal to the training apparatus. The magnetic field detector can be located external to the training apparatus and/or the syringe. A magnetic chip can thus be used to provide positional information about the needle inside both a live patient and a training apparatus, whereas a light source near the needle tip may not be able to provide positional information about the needle inside the patient.

The magnetic chips(s) can replace or be used in conjunction with an optical sensor in the needle. The syringe can include both the magnetic chip(s) and the optical sensor. Data from the magnetic chip(s) can be configured to overlay the three-dimensional data obtained from internal sensors in the syringe and/or the training apparatus, such as the light source in the needle tip captured by light detectors inside the training apparatus and/or the position sensors. The combination of data can be configured for building a neural network enabling deep leaning of the controller and/or the remote server of the injection system from the combination of data.

External Camera(s)

The injection system can optionally include one or more cameras 240 (see FIG. 1B), for example, depth cameras, located outside the training apparatus or external to the live patient to record an injection procedure. The external camera can be the Microsoft HoloLens worn by a user. Data from the HoloLens can be sent to a processor configured to process the data at a rate sufficient for tracking the syringe during the injection procedure, and/or to a neural network.

The external cameras can provide computer vision, which can include acquiring, processing, analyzing and/or understanding digital images taken by the external cameras. The external cameras can recognize a location of the training apparatus or the live patient in a three-dimensional space and/or certain locations on the training apparatus or the live patient, such as facial recognition. Data from the one or more external cameras can be configured to overlay the three-dimensional data obtained from the sensors in the syringe and/or the training apparatus, such as the light detection features and/or the position sensors, and/or data obtained from the magnetic sensor(s). The combination of data can be configured for building a neural network enabling deep learning of the processor. The data recorded by the external cameras can also be used as ground truth reference data for the three-dimensional data based on the sensors in the syringe and/or the training apparatus.

The external cameras can be used to record data of an injection procedure performed on a live patient. The external cameras can be used with a head band, and/or glasses, such as described in U.S. Patent Publication No. 2017/0178540 A1, filed on Dec. 22, 2016 and entitled "INJECTION TRAINING WITH MODELED BEHAVIOR," which is incorporated by referenced herein in its entirety, or a helmet fixture described below, which can mark anatomical landmarks and/or injection target locations. A scanner device, such as described in U.S. Patent Publication No. 2017/0245943 A1, filed on Feb. 27, 2017 and entitled "COSMETIC AND THERAPEUTIC INJECTION SAFETY SYSTEMS, METHODS, AND DEVICES," which is incorporated by referenced herein in its entirety, can be configured to determine locations of arteries, veins, and/or nerves underneath the patient's skin. The head band, glasses, helmet, and/or scanner device can be used in combination with the external cameras to provide computer vision.

Figure 11B:
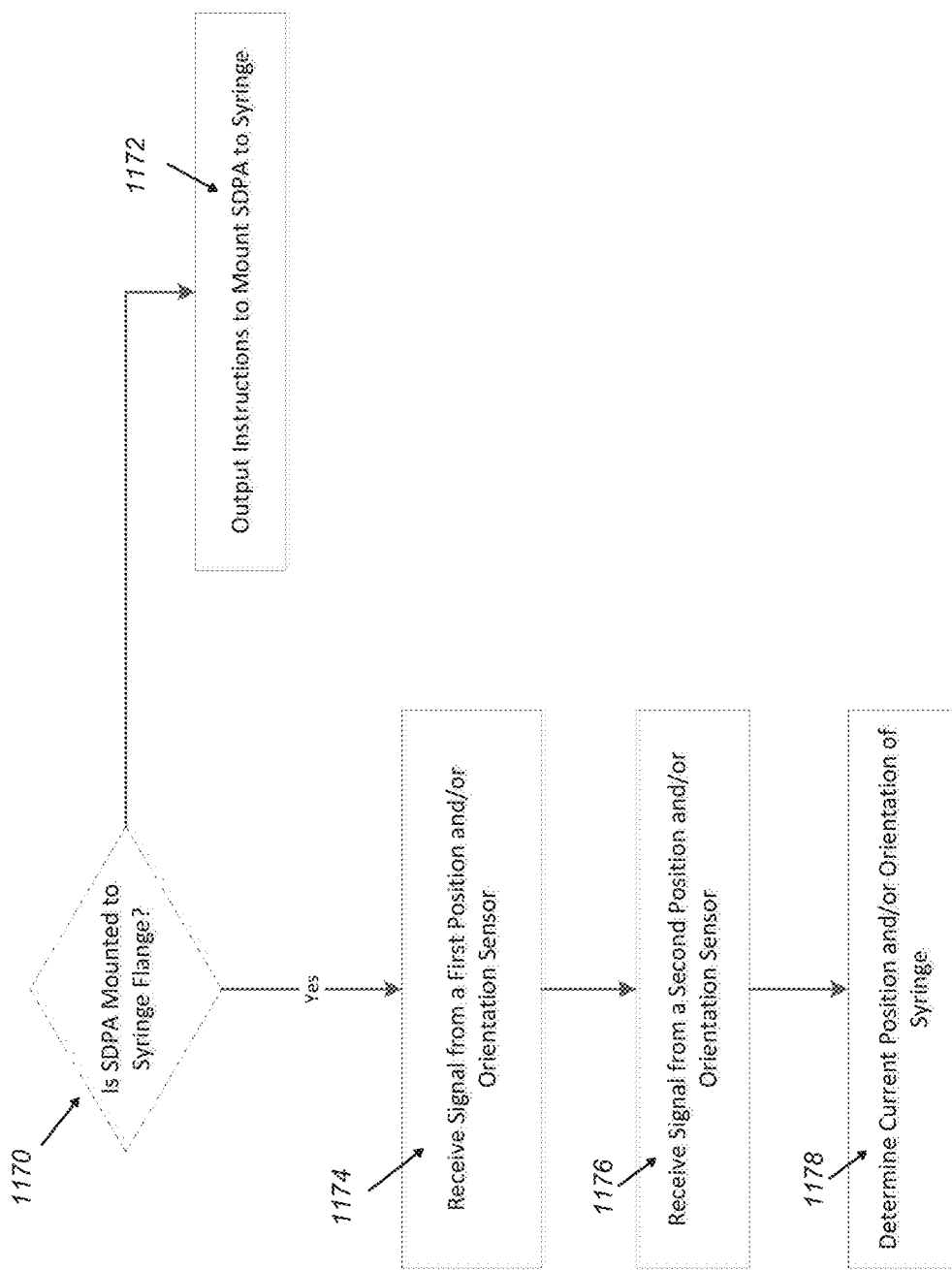
FIG. 11B illustrates schematically a flow chart of an example method of syringe position and/or orientation determination.

FIG. 11B illustrates an example flow chart for a method of determining the syringe position and/or orientation. At step 1170, the controller can optionally determine whether the SDPA is mounted to the syringe flange. For example, the controller can determine that the SDPA has been mounted to the syringe upon detection of a medication code on the flange by the medication code reader described herein. If the SDPA has not been mounted to the syringe flange, at step 1172, the controller can output an instruction to a user, such as an injector or a nurse, to mount the SDPA to the syringe. If the SDPA has been mounted to the syringe flange, at step 1174, the controller can receive a signal from a first position and/or orientation sensor. At step 1176, the controller can receive a signal from a second position and/or orientation sensor. The first and/or second position and/or orientation sensor can include an inertial navigation system, an internal optical sensor including the light source in the syringe and one or more camera(s) inside the training apparatus, an external optical sensor such as one or more externa cameras, and/or one or more magnetic sensors. At step 1178, the controller can determine the current position and/or orientation of the syringe based at least in part on the signal from the first or second sensor, or a combination of the signals from the first and second signals.

Needle-In-Artery Detection

The injection system can include warning features when a needle tip penetrates and/or is inside an artery. Injecting certain materials into an artery, such as filler materials in cosmetic facial injections, therapeutic injections, and/or orthopedic procedures (such as a knee surgery), can occlude the artery. Some materials can be used to bulk up facial features for an extended period and can have high viscosity to reduce the chance of migration and prolong the effective life of the materials. The viscosity of some materials can be higher than the blood (such as the arterial blood). When injected into the artery, the materials can block the blood flow in the artery. Occluding the artery can be harmful to the patient, leading to blindness, tissue death, and/or other negative consequences.

A pressure applied on the plunger and the plunger travel can be monitored, using methods as described herein, to reduce the risk of a needle tip inside an artery. The flow of injection material(s) from the needle tip can be attenuated based on an arterial blood pressure of the patient when the tip penetrates the arterial wall. The injection system can be configured to control the fluid pressure at the needle tip such that the flow from the needle tip can be stopped if the tip is immersed in an environment at an elevated pressure.

Figure 12A:
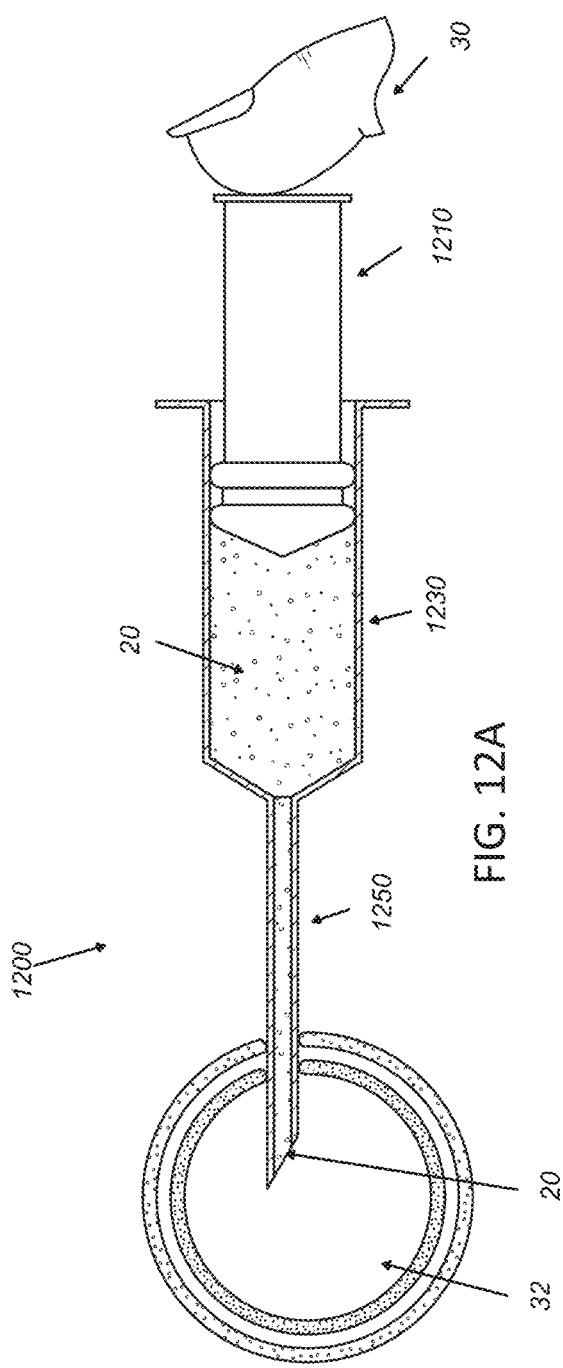
FIG. 12A illustrates schematically an example syringe with needle-in-blood-vessel detection features.

As shown in FIG. 12A, if the needle 1250 is inside an artery 32, the tip of the needle 1250 can be surrounded by a blood flow at an arterial pressure. A diastolic blood pressure can be about 60 to about 80 mm Hg for a healthy adult patient. A systolic blood pressure can be about 80 to about 120 mm Hg for a healthy adult patient. Injection target locations in the patient's body can have a lower pressure than the lowest arterial pressure, such as the diastolic pressure of the patient.

In order for the injection material(s) 20 to flow from the syringe body 1230, through the needle 1250, into the tissue, the pressure of the material(s) 20 exiting the needle 1250 needs to be higher than an ambient pressure adjacent to but external to the needle tip. If the ambient pressure is equal to or greater than the injection material(s) pressure, the flow of injection material(s) 20 from the needle 1250 to the surrounding can stop. The flow can also reverse in direction in some situations.

The pressure of the material(s) exiting the needle 1250 can be substantially the same as a pressure applied by an injector 30 on the plunger 1210. The pressure can be a static pressure. The pressure applied on the plunger 1210 can be measured by a variety of methods. For example, the pressure can be measured by a pressure sensor. The pressure applied on the plunger 1210 can also be calculated from a force on the plunger 1210 measured by a force sensor. The force sensor can be located on the thumb portion of the plunger 1210 or elsewhere on the syringe 1200. The pressure of the injection material(s) 20 inside the syringe body 1230 can be equal to the force on the plunger 1210 divided by a surface area of the thumb portion of the plunger 1210.

Figure 12B:
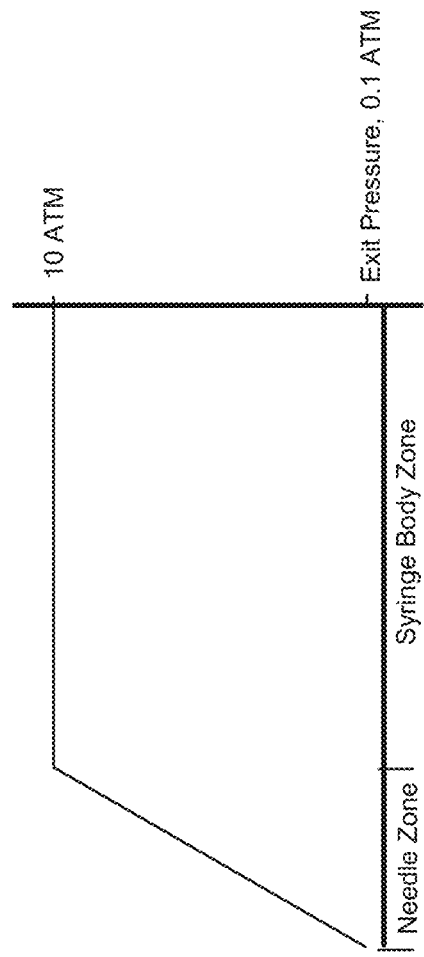
FIG. 12B illustrates schematically a pressure drop profile for a flow of medication exiting a syringe into body tissues.

As the injection material(s) 20 flow(s) through the needle 1250, the pressure of the injection material(s) 20 drops. FIG. 12B illustrates schematically a pressure profile for a flow of medication exiting a syringe into flesh and calculation of a pressure applied to injection material(s) inside a syringe body. A small needle bore, a long needle, and/or a fast flow of the injection material(s) can lead to more pressure drop than a large needle bore, a short needle, and/or a slow flow of the injection material(s). The force applied to the plunger can typically be from about zero to about 89 N. The surface area of the thumb portion can be about 77.4 mm square. The pressure of the injection material(s) can typically be about 1.1 MPa or about 11 atmospheres.

The injection system can have a needle-in-artery detection feature by applying a pressure significantly lower than a typical pressure applied to the plunger (for example, at about 1.1 MPa or about 11 atmospheres). The system can monitor the needle tip pressure, or instruct the user to provide a pressure on the plunger, such that the pressure is less than the lowest arterial blood pressure of the patient (such as the diastolic blood pressure). The controller can monitor travel of the plunger, using methods such as described herein, when the low pressure is applied.

Figure 12C:
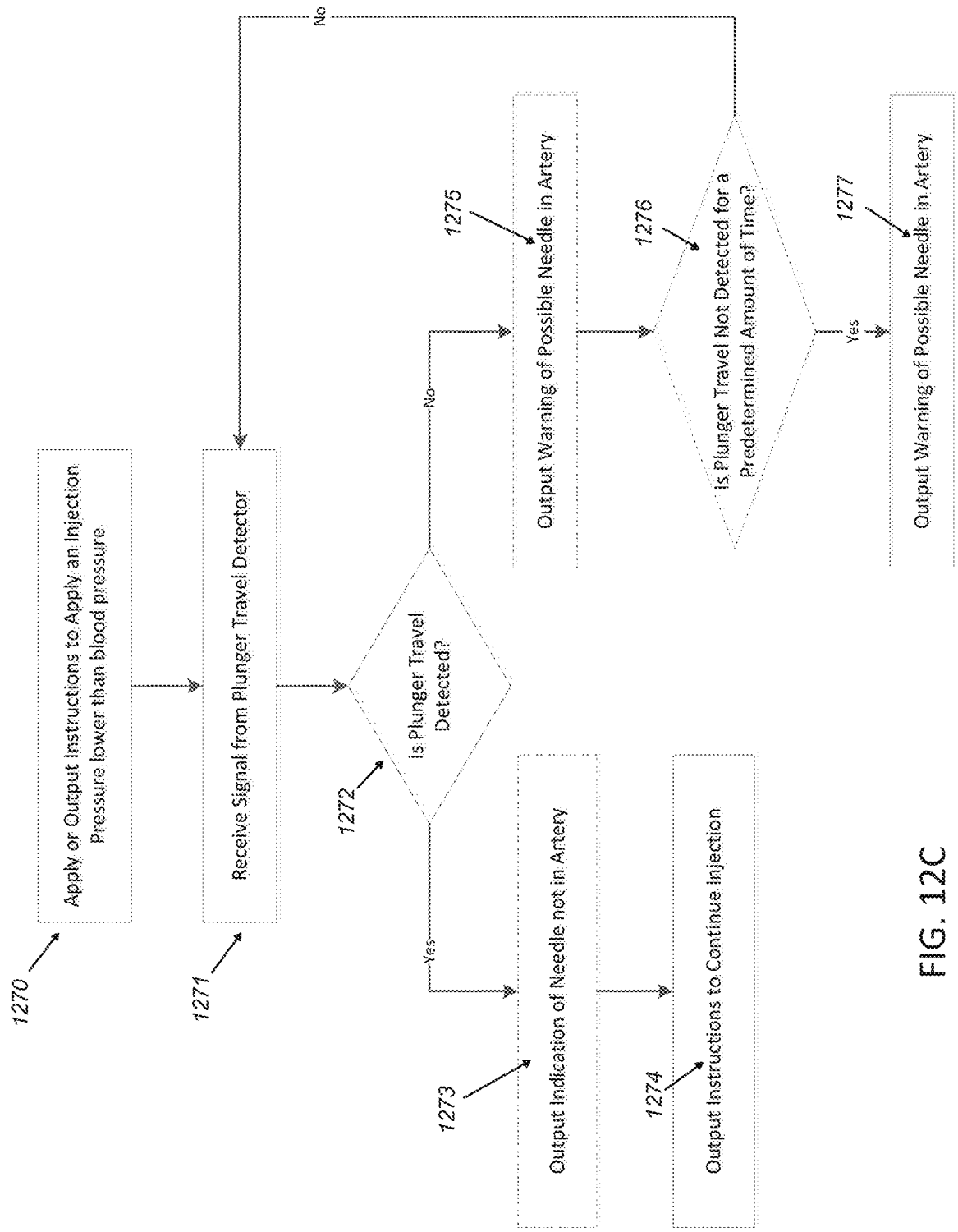
FIG. 12C illustrates schematically a flow chart of an example method of detecting needle in artery.

By adjusting a force or pressure (such as a static force or pressure) applied to the plunger and monitoring the travel of the plunger, the pressure of the injection material(s) at the needle tip can be controlled. FIG. 12 illustrates an example process for detecting whether the needle has penetrated and/or is in the artery. The process described herein can then be followed by a conventional injection procedure with a nominal medication injection volume and injection rates. In the flow chart shown in FIG. 12C, at step 1270, the controller can control the needle tip pressure and/or instruct the user to apply a needle tip pressure that is lower than a predetermined blood pressure. The predetermined blood pressure can be the lowest arterial blood pressure of a patient. By controlling the needle tip pressure such that it is less than the lowest arterial blood pressure of the patient (such as the diastolic blood pressure), the flow of injection material(s) from needle tip into the artery can be stopped. The injection material(s) can be prevented from entering into the artery and the risk of arterial blockage due to the injection material(s) can be reduced and/or avoided.

At step 1271, the controller can receive signals from the plunger travel sensor as described herein. At decision step 1272, the controller can determine whether the plunger has been advanced distally relative to the syringe body as described above. If a plunger travel is detected, at step 1273, the controller can optionally output an indication that the needle is likely not in an artery. At step 1274, the controller can output an instruction for the injector to continue with the injection. If a plunger travel is not detected, at step 1275, the controller can optionally output an indication that the needle tip is inside a high pressure environment, which may or may not be an artery. At decision step 1276, the controller can optionally determine whether no distal plunger travel is detected for a certain duration and/or when the plunger travels proximally away from the needle. If the plunger has not moved distally for the predetermined amount of time and/or if the plunger has moved proximally, at step 1277, the controller can output a warning that the needle is inside an artery. If distal plunger travel is detected within the predetermined amount of time, the controller can return to step 1271.

The injection system can also have indicator features for informing the patient and/or the injector whether the needle tip is inside an artery. The indicator features can be on the syringe, on a display device, and/or elsewhere in a room in which the injection procedure is performed. The indicator features can have a plurality of colored lights. The display device can run an application or software to display the last injection site (such as on the patient's face) so that the injector can go in to the last injection site promptly to search for occlusion(s). The indicator features can also include instructions to the injector to use a solvent or any other product to remove the occlusion. The solvent can comprise hyaluronidase, such as Hylenex or Vitrase. When the pressure applied to the plunger is at or slightly lower than the lowest arterial pressure of the patient, the system can switch on a green light when the plunger travel is detected (for example, for a certain duration) and/or when the plunger travel speed exceeds a predetermined threshold value. The green light can indicate that the needle is not inside an artery. The system can switch on a yellow light if no travel of the plunger is detected. No plunger travel detection can indicate that the needle tip is inside a high pressure environment, which may or may not be an artery. The system can switch on a red light if no plunger travel is detected for a certain duration and/or when the plunger travels proximally away from the needle. The red light can indicate that the needle is inside an artery. The system can optionally switch on the red light without showing a yellow light. The system can also instruct the trainee or injector to push the needle further to completely go through the artery and/or to pull back the needle to move to a new location. Different color schemes can be used to provide warning to the user. Audio signals can also be used as the indicators, or lights, audio signals, and/or haptic feedback features can be used as a combination of indicators.

Charging Base

Figure 13:
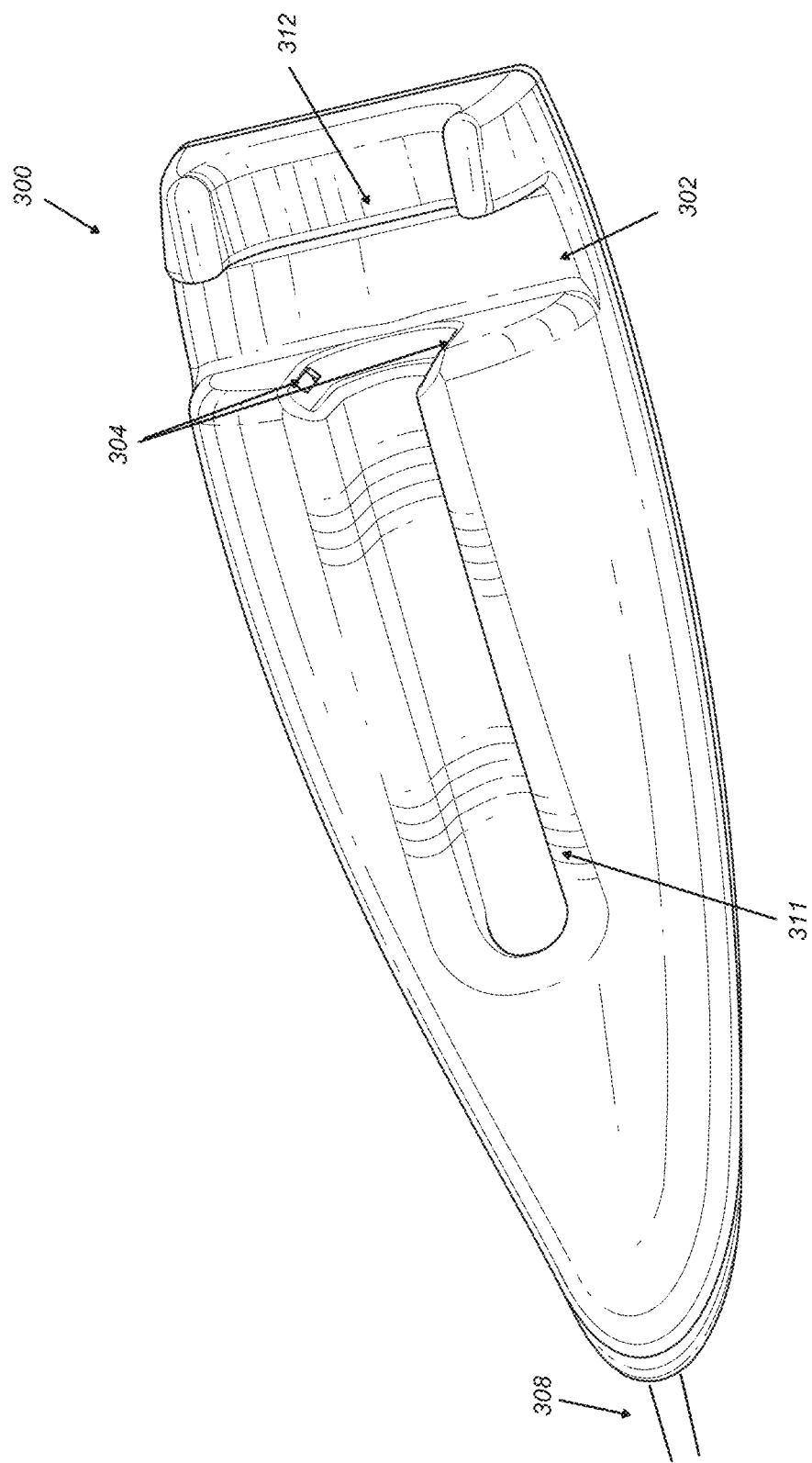
FIG. 13 illustrates an example syringe charging base.
Figure 14:
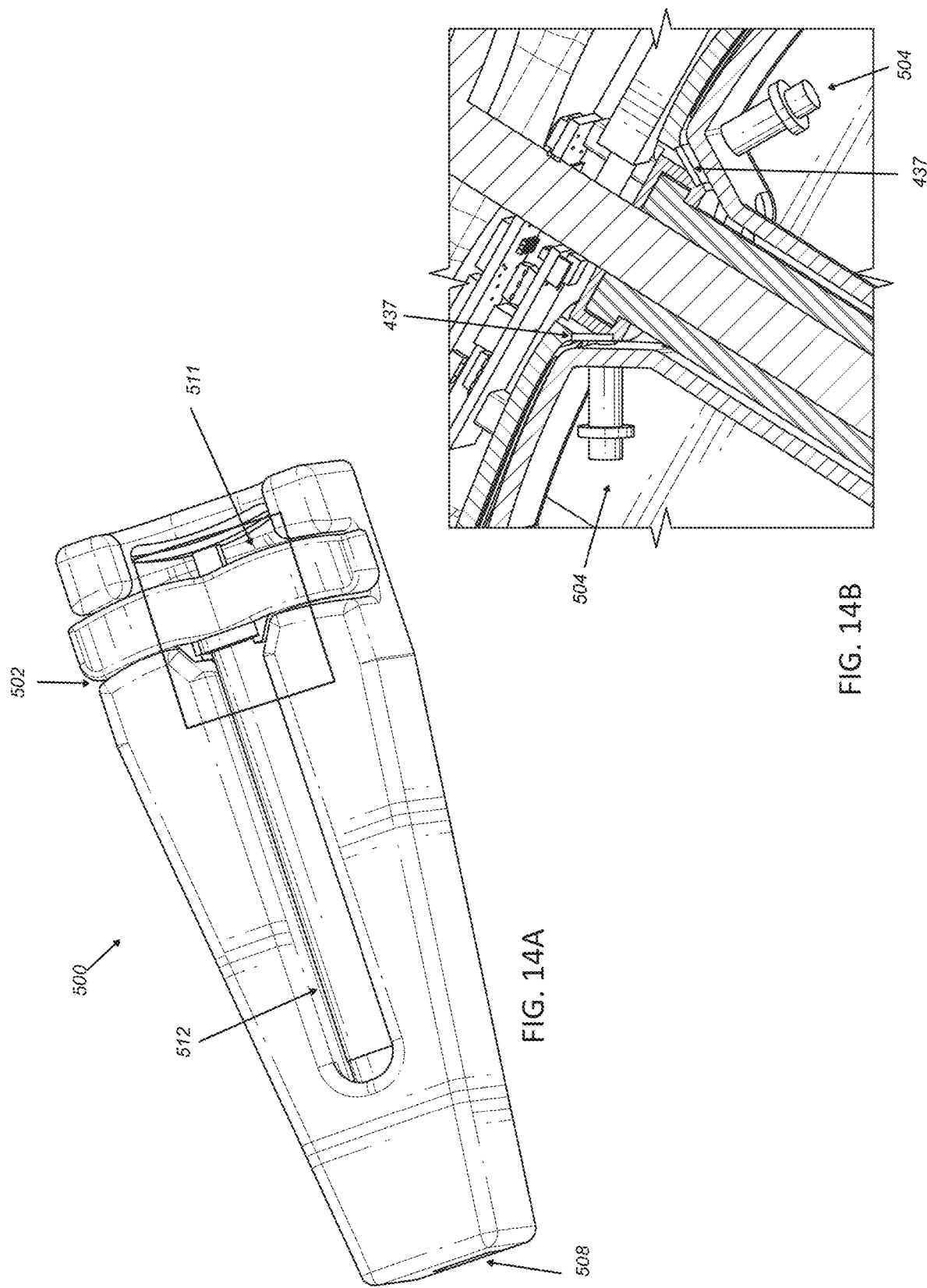
FIG. 14A illustrates another example syringe charging base loaded with a syringe.
FIG. 14B illustrates a detailed view of charging features of the charging base and the syringe flange.

The injection system can include a charging station for recharging the power source, such as a rechargeable battery, on the SDPA. FIG. 13 illustrates an example charging station 300. FIG. 14A illustrates another example charging station 500 with a slightly different outer shape. The charging station 300, 500 can include a generally T-shaped cradle 302, 502 shaped for receiving the syringe body, which can be any of the syringe bodies described herein. A short side 312, 512 of the cradle 302, 502 can accommodate the flange of the syringe body, including the SDPA described herein. A long side 311, 511 of the cradle 302, 502 can accommodate the body portion of the syringe. One or more electrical contacts 304, 504, such as pogo pins, can be positioned in the cradle 302, 502. As shown in FIGS. 13 and 14A-B, the electrical contacts 304, 504 can each be located at a juncture of the short and long sides of the cradle 302, 502. The electrical contacts 304, 504 can come into contact with electrical pads on the flange base, such as the pads 437 in FIGS. 4A and 9B. The electrical contacts can be located on another portion of the charging base. The electrical pad can be located on another part of the syringe.

As shown in FIG. 14B, the electrical contacts 504 can each have a pogo pin 506 extending into the charging station 500. When the pogo pins 504 make contact with the electrical pads 437, the pogo pins 504 can connect the SDPA of the syringe to a charging circuit so as to charge the power source in the syringe. The charging station 300 in FIG. 13 can have a charging circuit configured to be connected to an external power source via a power cord 308. The charging station 500 in FIGS. 14A-B can have a charging circuit configured to be connected to an external power source via a USB port 508.

Home Cradle

Figure 15:
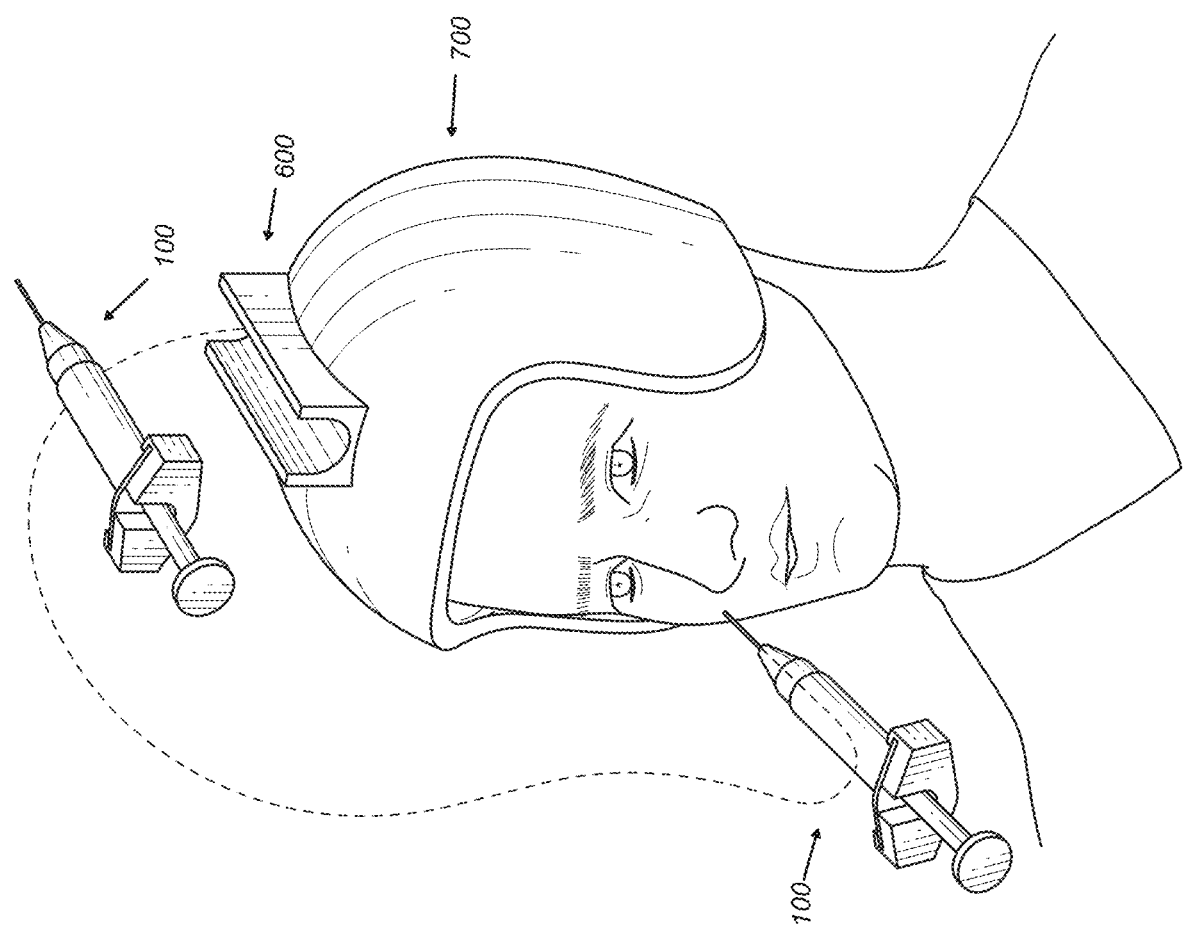
FIG. 15 illustrates schematically an example syringe cradle with a syringe.

The injection system can include a home cradle for providing an initial position for the syringe. FIG. 15 illustrates an example home cradle 600. The cradle 600 can be configured to support any of the syringes described above, such as the syringe 100. The cradle 600 can be attached releasably or permanently to a helmet fixture 700. The helmet fixture 700 can also be a headband or any other fixture that can be releasably attached to the injection location. The helmet fixture 700 can be worn by a live patient or the training apparatus. The helmet fixture can also be any other type of fixture that can be secured to the live patient or the training apparatus.

When the helmet fixture 700 is worn on the patient's head or the training apparatus, a position of the syringe held by the home cradle 600 can be taken to provide the initial position of the syringe. The position and/or location of the syringe 100 after the syringe 100 has been removed from the cradle 600 can be determined using the position sensor on the SDPA, the light detectors inside the training apparatus, and/or other sensors described herein. Terminology Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "applying a pressure" include "instructing application of a pressure."

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An injection system, the system comprising:
    a syringe having a needle, the needle comprising an optic fiber disposed within a lumen of the needle, the optic fiber terminating distally at or near a tip of the needle;
    the syringe further comprising a syringe body and a plunger, the plunger configured to move axially relative to the syringe body; and
    the syringe body comprising a body portion having a proximal end and a distal end, a flange portion at the proximal end, and a needle coupling portion disposed at or near the distal end, the syringe body further comprising a light source disposed at or near the distal end;
    wherein when the needle is coupled to the needle coupling portion of the syringe body, the optic fiber is coupled to a power source so as to direct light emitted by the light source out through the tip of the needle, the power source also configured to power the light source, and
    wherein the power source is mounted to the flange portion, the syringe body portion comprising a wire lumen, one or more lead wires extending from the power source through the wire lumen, the one or more lead wires terminating at or near the distal end of the syringe body portion.

2. The injection system of claim 1, wherein the optic fiber extends proximally from a proximal end of the needle.

3. The injection system of claim 1, wherein the optic fiber is fused with the lumen of the needle.

4. The injection system of claim 1, wherein the needle is releasably coupled with the needle coupling portion by M3 threads.

5. The injection system of claim 1, wherein the flange portion comprises a flange housing that includes an internal compartment.

6. The injection system of claim 5, wherein the flange portion further comprises at least one circuit board mounted within the internal compartment.

7. The injection system of claim 6, wherein the at least one circuit board comprises one or more sensors configured to measure injection information about an injection procedure performed using the injection system.

8. The injection system of claim 7, wherein the one or more sensors comprise a plunger travel sensor, a force sensor, a pressure sensor, and/or a medication code reader.

9. The injection system of claim 7, wherein the injection information comprises one or more of:
    time of injection;
    type of medication;
    authenticity of medication;
    injection dose;
    identity of user of the system; and/or
    location of injection.

10. The injection system of claim 5, wherein the flange portion further comprises a flange base and a flange cover, wherein the flange base and flange cover are configured to be assembled to form the internal compartment.

11. The injection system of claim 10, wherein the flange base is an integral part of the syringe body, the flange cover comprising one or more slots configured to slidably accommodate the flange base.

12. The injection system of claim 10, wherein the flange base comprises a slot, the slot configured to slidably accommodate the flange cover.

13. The injection system of claim 12, wherein the slot is on a distal surface of the flange base.

14. The injection system of claim 1, wherein the flange portion further comprises an opening sized to accommodate the plunger of the syringe.

* * * * *